(12) United States Patent
Gertner

(10) Patent No.: US 7,832,407 B2
(45) Date of Patent: Nov. 16, 2010

(54) OBESITY TREATMENT SYSTEMS

(75) Inventor: Michael Gertner, 520 Laurel St., Menlo Park, CA (US) 94025

(73) Assignee: Michael Gertner, Menlo Park, CA (US)

( * ) Notice: Subject to any disclaimer, the term of this patent is extended or adjusted under 35 U.S.C. 154(b) by 1376 days.

(21) Appl. No.: 11/295,281

(22) Filed: Dec. 6, 2005

(65) Prior Publication Data

US 2006/0089571 A1    Apr. 27, 2006

Related U.S. Application Data

(63) Continuation-in-part of application No. PCT/US2005/033683, filed on Sep. 19, 2005, and a continuation-in-part of application No. 11/153,791, filed on Jun. 15, 2005, which is a continuation-in-part of application No. 11/148,519, filed on Jun. 9, 2005, said application No. 11/148,519 is a continuation-in-part of application No. 11/125,547, filed on May 10, 2005, now Pat. No. 7,670,279, said application No. 11/153,791 is a continuation-in-part of application No. 11/125,547, which is a continuation-in-part of application No. PCT/US2005/009322, filed on Mar. 19, 2005, which is a continuation-in-part of application No. 10/974,248, filed on Oct. 27, 2004, now Pat. No. 7,255,675.

(60) Provisional application No. 60/556,004, filed on Mar. 23, 2004, provisional application No. 60/584,219, filed on Jul. 1, 2004, provisional application No. 60/603,944, filed on Aug. 23, 2004.

(51) Int. Cl.
*A61B 19/00* (2006.01)

(52) U.S. Cl. .................................................. 128/898

(58) Field of Classification Search ............... 604/8, 604/9; 600/29–32, 37; 606/191, 192, 196
See application file for complete search history.

(56) References Cited

U.S. PATENT DOCUMENTS

| | | | | |
|---|---|---|---|---|
| 4,696,288 A | * | 9/1987 | Kuzmak et al. | 128/898 |
| 5,188,104 A | * | 2/1993 | Wernicke et al. | 607/40 |
| 5,496,311 A | * | 3/1996 | Abele et al. | 606/28 |
| 2003/0093117 A1 | * | 5/2003 | Saadat | 606/221 |
| 2005/0222638 A1 | * | 10/2005 | Foley et al. | 607/40 |

FOREIGN PATENT DOCUMENTS

WO  WO 2005007232 A1 *  1/2005  ................ 600/37

* cited by examiner

*Primary Examiner*—Samuel G Gilbert
(74) *Attorney, Agent, or Firm*—Michael Gertner

(57) ABSTRACT

In some embodiments, methods to sense parameters associated with restriction procedures and/or devices are disclosed. In some embodiments, the parameters are sensed directly from the region of the procedure and/or device and in other embodiments, associated neural pathways are sensed. Methods for further optimization of the obesity treatment regimens are also disclosed.

20 Claims, 48 Drawing Sheets

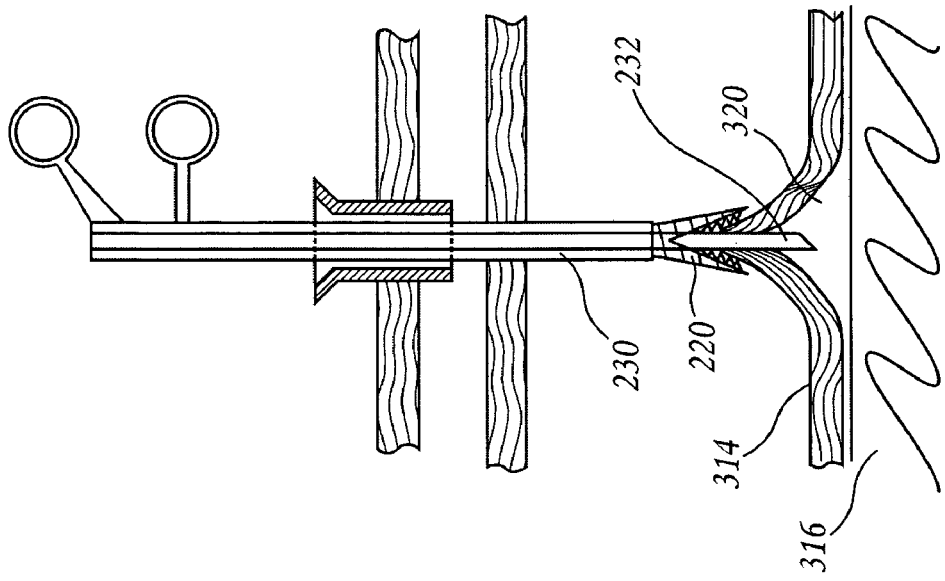
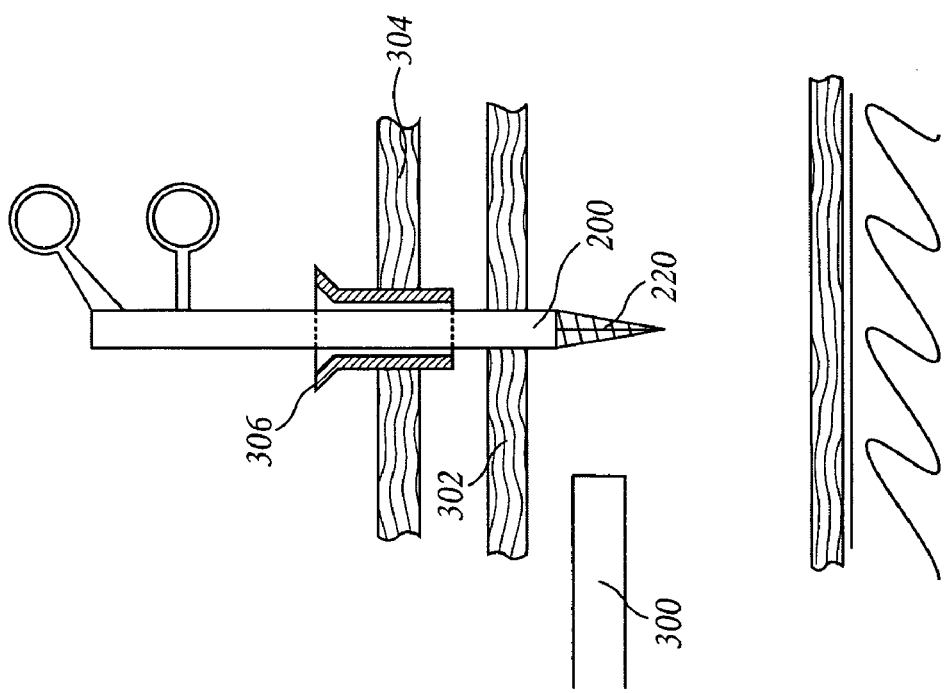

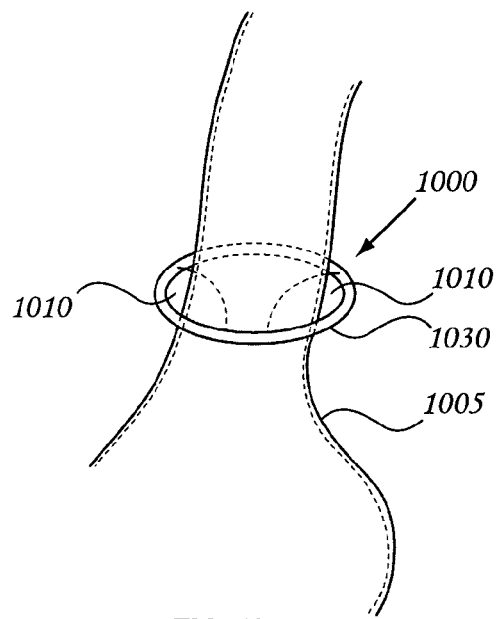
FIG. 18A
FIG. 18B
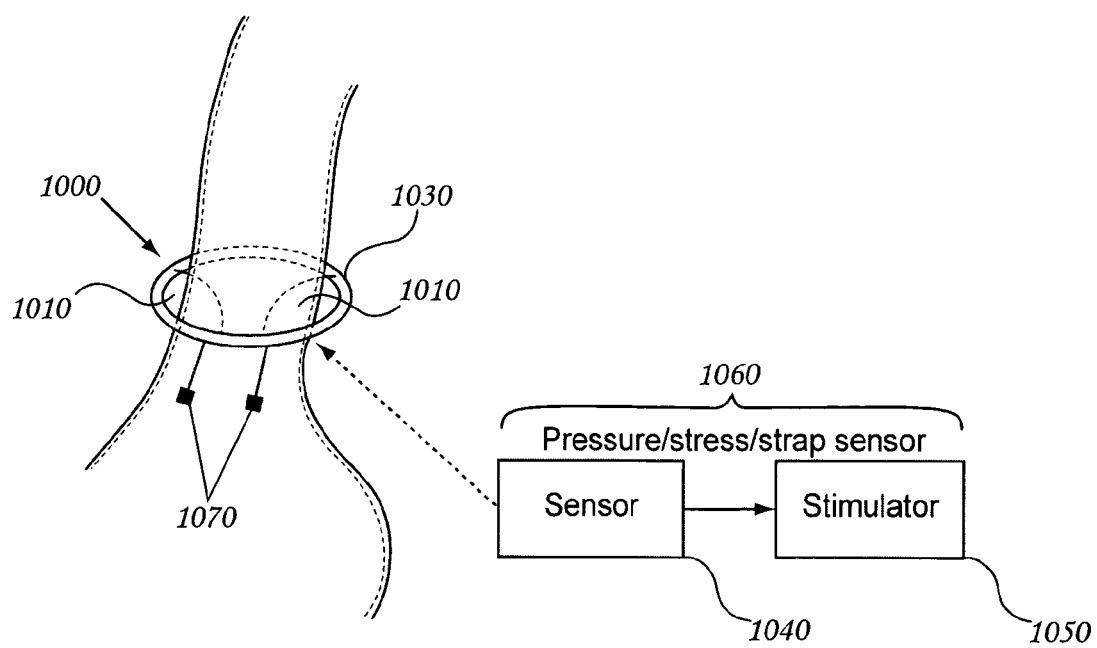
FIG. 18C

OBESITY TREATMENT SYSTEMS

RELATED APPLICATIONS

The present application is a continuation-in-part of International Patent Application PCT/US2005/033683 filed Sep. 19, 2005 which is a continuation-in-part of U.S. Non-Provisional patent application Ser. No. 11/148,519 entitled "Methods and Devices for Percutaneous, Non-Laparoscopic Treatment of Obesity," filed on Jun. 9, 2005 by Michael Gertner, MD, and is also a continuation-in-part of U.S. Non-Provisional patent application Ser. No. 11/153,791 entitled "Methods and Devices for the Surgical Creation of Satiety and Biofeedback Pathways," filed on Jun. 15, 2005, both of which are continuation-in-parts of U.S. Non-Provisional patent application Ser. No. 11/125,547 by Michael Gertner, M.D., entitled "Percutaneous Gastroplasty" filed May 10, 2005, now U.S. Pat. No. 7,670,279 which is a continuation-in-part of International Patent Application No. PCT/US05/09322 by Michael Gertner, M.D., filed Mar. 19, 2005, designating the United States, entitled "DEVICE AND METHODS TO TREAT A PATIENT," which is a continuation-in-part of U.S. Non-Provisional patent application Ser. No. 10/974,248 by Michael Gertner, M.D. filed Oct. 27, 2004, now U.S. Pat. No. 7,255,675 entitled "DEVICES AND METHODS TO TREAT A PATIENT," which claims priority to U.S. Provisional Patent Application Ser. No. 60/556,004 filed Mar. 23, 2004 by Michael Gertner, M.D., entitled "BARIATRIC DEVICES AND IMPLANTATION METHODS," to U.S. Provisional Patent Application Ser. No. 60/584,219 filed Jul. 1, 2004 by Michael Gertner, M.D., entitled "DEVICES AND METHODS FOR PERCUTANEOUS GASTROPLASTY," to U.S. Provisional Patent Application Ser. No. 60/603,944 filed Aug. 23, 2004 by Michael Gertner, M.D., entitled "DEVICES AND METHODS TO TREAT MORBID OBESITY," all of which are herein incorporated by reference in their entirety.

BACKGROUND OF THE INVENTION

1. Field of the Invention

The present invention relates to devices, methods and apparatus to treat obesity. Implantable devices, methods to implant implantable devices, and surgical devices to enable the implantation of the implantable devices in, around, or near the walls of organs or vessels are disclosed, including devices to appose the walls of the stomach. Feedback systems are also disclosed which enable multimodality therapy such as gastric restriction in combination with electrical stimulation of the stomach, sensing of feeding parameters, and/or other efferent or afferent neural pathways in a patient.

2. Description of the Related Art

Obesity is a public health problem of extreme national and international importance. There are an estimated 60 million obese adults and 2 million obese adolescents in the United States as of 2004. By some estimates, there are 1 billion obese individuals worldwide. Indeed, to highlight the worldwide importance of the disease, a recent report estimated that over there are over 60 million obese individuals in China, a 10-fold increase since 2000. Obesity affects the life quality and productivity of those effected and leads to long-term health related complications such as diabetes and heart disease. Some researchers estimate that if the obesity epidemic is not brought under control, it could quickly overwhelm societal resources.

To date, surgery is the only proven method for inducing substantial weight loss. The mechanism behind the success of surgery is, in many cases, not known because obesity is such a complex, multifactorial disease. Some researchers propose that surgery does no more than provide biofeedback for appetite retraining. Other researchers maintain that surgery alters the physiology of the patient such that satiety is induced earlier or fewer nutrients are absorbed. Nonetheless, the consensus among most obesity researchers is that at the current time, long-term weight loss is only possible by surgical means and that the success of surgery is due to a multifactorial set of changes.

Over the past four decades, there have been numerous surgical procedures and devices developed to treat those who suffer from morbid obesity. In general, there are two physiologic components of all past and current procedures: malabsorption and mechanical restriction/volume reduction. Newer methods and devices include stimulation devices such as neurostimulators and muscle stimulators. In general, these devices will require further research and development before they will be used to treat obese patients as a single therapy.

Many of the procedures performed in the past have proven to be impractical, dangerous, and/or detrimental to patient health and are now of historical importance only. One example of a failed procedure was the jejuno-ileo bypass in which a malabsorptive state was created through the bypass of a large portion of the intestine through the creation of a surgical anastomosis between the jejunum and the ileum. While patients initially lost a great deal of weight, liver failure or liver damage occurred in over one-third of the patients, necessitating reversal of the surgical procedures.

One of the first restrictive type surgical procedures was the so-called "stomach stapling" operation in which a row of horizontal staples was placed across the upper stomach and then several staples were removed from the staple line to create an opening, the "os," for a small amount of food, but not too much food. This procedure was mostly restrictive, leading to an early feeling of satiety. This surgery was abandoned because 70%-80% of patients had inadequate weight loss due to staple line dehiscence (i.e. the staples pulled through the stomach wall). A procedure to stabilize the staple line was performed by Smith et. al. (Lindsay B. Smith; Modification of the Gastric Partitioning Operation For Morbid Obesity. Am. J. Surgery 142, December 1981) in which the staple line was buttressed in the region where the staples were removed using teflon pledgets with sutures passing through the middle of the pledgets. The purpose of the pledgets was to buttress the suture and distribute the load across the suture to the pledget, thereby preventing the suture from pulling through the stomach and therefore stabilizing the os. The outcomes showed that the suture buttress was unequivocally able to prevent the suture from tearing through the stomach wall; indeed, over 90% of the patients showed excellent weight loss at 18 months.

The Roux-en-Y (The Roux) bypass operation has become the most commonly performed surgical procedure to treat the morbidly obese in the United States. It combines a small degree of malabsorption with a 90% reduction in the volume of the stomach. In the United States, 150,000 Roux procedures were performed in the year 2004. This number is expected to rise to 500,000 procedures by 2007. The procedure actually has been performed since the late 1970's but has evolved substantially over the past three decades into a relatively safe and effective procedure; indeed, the long-term data are very good. The advent of laparoscopic surgery and hence the laparoscopic Roux-en-Y bypass in combination with excellent follow-up results from the open (and laparoscopic) procedure are reasons for the proliferation of the Roux procedure.

Despite the efficacy of the Roux procedure and the recent laparoscopic improvements, it remains a highly invasive procedure with substantial morbidity, including a 1-2% surgical mortality, a 20-30% incidence of pulmonary morbidity such as pneumonia, pulmonary embolism, etc., and a 1-4% chance of leak at the anastomotic site which can result in a spectrum of consequences ranging from an extended hospital stay to death. Furthermore, it is not a good option for adolescents in whom the long-term consequences of malabsorption are not known. In addition, many patients resist such an irreversible, life altering procedure.

The Roux procedure requires general anesthesia and muscle paralysis which, in the morbidly obese population, is not of small consequence. There is also a substantial rate of anastomotic stricture which results in severe lifestyle changes for patients. As an example, many patients are forced to vomit after meals. Furthermore, although minor when compared to previous malabsorptive (e.g. jejuno-ileal bypass) procedures, the malabsorption created by the Roux-en-Y procedure can dramatically affect the quality of life of patients who undergo the procedure; for example, they may experience gas bloating, symptoms of the dumping syndrome, and/or dysphasia. In addition, these patients can experience very early fullness such that they are forced to vomit following meals.

Recently, minimally invasive procedures and devices which create a feeling of early satiety have been introduced into the marketplace in an attempt to address some of the issues above. The LAP-BAND™ is a band which encircles the stomach at the region of the fundus-cardia junction; it is a restrictive procedure similar to stomach stapling. It requires general anesthesia, a pneumoperitoneum, muscle paralysis, and extensive dissection of the stomach at the level the gastroesophageal junction. It also requires continual adjustment of the band, or restriction portion of the device. Although less invasive than the Roux procedure and potentially reversible, the LAP-BAND™ is nonetheless quite invasive. It also does not reduce the volume of the stomach by any great extent and some patients report a feeling of hunger much of the time. Furthermore, once implanted, the Lap-Band™, although it is adjustable by percutaneous means, is in fact very difficult to adjust and many iterative adjustments are required before it is made right.

Long-term clinical follow-up reveals that the banding procedure results in many complications. In a recently published article (Camerini et. al. Thirteen Years of Follow-up in Patients with Adjustable Silicone Gastric Banding for Obesity: Weight Loss and Constant Rate of Late Specific Complications. Obesity Surgery, 14, 1343-1348), the authors reported a 60% prevalence of late band removal secondary to complications such as erosion, slippage of the band, infection, or lack of effectiveness. Nonetheless, the LAP-BAND™ as a procedure is becoming very popular across the world as it is a less invasive and reversible procedure. The weight loss in long-term trials is considered adequate by some and inadequate by many; across various studies, the average weight loss is approximately 40% of excess body weight which is well below the weight loss in the Roux, VBG, and duodenal switch procedures (see below).

Other procedures which have been tried in the past and which offer varying degrees of weight loss include several variations of the original "gastroplasty" procedures. These procedures represent an evolution of the so-called "stomach stapling" procedure discussed above. These procedures were attempted prior to and concomitant with the evolution of the Roux-en-Y. They became popular (despite despite offering less weight loss than the Roux) because of their substantially less invasive nature and possible reversibility.

One such example is called the vertical banded gastroplasty, or VBG, which again, involves the creation of a restricting "os" for food. In the VBG, the border of the "os" is the lesser curvature of the stomach which is less apt to dilate than the fundus region of the stomach. Furthermore, the procedure completely excludes the fundus which is thought to easily dilate and in fact, is physiologically "programmed" to dilate during meals . . . so-called "receptive relaxation." Dilation of the fundus as a result of continued overeating is a major reason for failure of the Lap-Band and in some cases the Roux procedure and the development of the VBG was intended to improve upon these outcomes. One issue with the VBG is that, as practiced today, it is not reversible, nor is it adjustable, and it is difficult to perform laparoscopically. As in the horizontal gastroplasty, the VBG utilizes standard staplers which, as in the horizontal gastroplasty, are unreliable when applied to the stomach. In the case of the VBG, the row of staples runs parallel to the lesser curvature of the stomach. An important reason for recurrent weight gain in the VBG is in fact recannulation of the staple line, leading to a so-called gastro-gastric fistula.

A recent, prospective, randomized trial, compared the VBG to the adjustable banding procedure and found that the VBG was overwhelmingly superior to the banding procedure (Morino et. al. Laparoscopic Adjustable Silicone Gastric Banding Versus Vertical Banded Gastroplasty in Morbidly Obese Patients. Annals of Surgery. Vol. 238 (6) pps. 835-842). Twenty five percent of the patients in the banding group returned to the operating room whereas there were no returns to the operating room in the gastroplasty group. The degree of weight loss was close to 60% of excess body weight after three years in the gastroplasty group and closer to 40% of excess body weight in the banding group. Although in this study, the VBG was successfully performed laparoscopically, the laparoscopic VBG procedure is in fact, difficult to perform, because the procedure is not standardized and a "tool box" does not exist for the surgeon to carry out the procedure; furthermore, the procedure is not a reversible one and relies on the inherently unreliable stapler systems.

A recent meta-analysis and systematic review (Buchwald et. al. Bariatric Surgery: A Systematic Review and Meta-analysis; JAMA vol. 292, no 14. pps 1724-1737) indicated that vertical gastroplasty (avg. excess weight loss of 68.2%) is superior to adjustable banding (avg excess weight loss of 47.5%) and gastric bypass (avg excess weight loss of 61.6%).

The Magenstrasse and Mill (M&M) procedure is an evolving gastroplasty technique wherein the greater curvature of the stomach is separated (stapled and cut) from the path of food, leaving a tube of stomach, the Magenstrasse, or "street of the stomach," which is comprised of the lesser curvature. This procedure is similar to the VBG except that the longitudinal staple line of the stomach extends further along the lesser curvature and into the antrum. The theory behind leaving the antral "mill" is that it will continue to serve its normal function of mixing, grinding, retropulsion, and well-orchestrated expulsion of chyme into the duodenum. An authoritative study on the operation is incorporated herein by reference (Johnston et. al. The Magenstrasse and Mill Operation for Morbid Obesity; Obesity Surgery 13, 10-16).

In summary, the vertical gastroplasty procedure appears to be superior to the banding procedure. However, the vertical gastroplasty procedure is not easily performed laparoscopically and furthermore, it is not easily reversible. Therefore, a need exists to standardize the vertical banded gastroplasty and create a safer procedure which is also easy to perform, is durable, and is reversible.

The intragastric balloon is not a new concept. The intragastric balloon is meant to displace volume within the stomach such that a smaller volume of food leads to an earlier feeling of satiety. Currently, intragastric balloons on the market are not fixed to the stomach and consequently, can lead to complications such as obstruction and mucosal erosion. To avoid these complications, the balloons are removed after a maximum of six months. In a prospective, non-randomized, unblinded study (Sallet et. al. Brazilian Multicenter Study of the Intragastric Balloon; Obesity Surgery, 14, 991-998), the average excess weight loss was 48.3% after 1 year. However, the incidence of nausea and vomiting was 40% and epigastric pain was 20%; balloon impaction occurred in 0.6% of patients. A balloon which is fixed to the wall of the stomach could potentially improve the intragastric balloon device and allow longer-term implantation.

More recently, there has been an effort to develop even less invasive devices and procedures which do not involve incisions at all. For the most part, these procedures are performed from within the stomach with an endoscope and by a physician with a high degree of endoscopic skill. For example, U.S. Pat. No. 6,558,400 describes methods and devices to create partitions in the stomach. Anchors or staplers applied through an endoscope from within the stomach are used to accomplish the partitions. Similarly, U.S. Patent Application Publication No. 2004/0122456 describes another set of methods and devices to reduce the volume of the stomach. Expandable anchors are deployed both on the anterior and posterior wall of the stomach using an endoscope. Flexible sutures are brought out of the patient's mouth and the sutures are crimped together within the stomach in order to bring the walls of the stomach closer together. The final configuration has a discontinuous connector positioned between the anterior and posterior anchors. U.S. Pat. No. 6,773,440 describes a device which is advanced through an endoscope and grasps or applies suction to a fold of mucosa to apply anchors through the mucosal and serosal layers of the stomach.

Endoscopic procedures to manipulate the stomach can be time consuming because of the technical difficulty of the endoscopy; they also require a large endoscope through which many instruments need to be placed for these complex procedures. Due to the large size of the endoscope, patients typically will require general anesthesia, which limits the "non-invasive" aspects of the procedure. Furthermore, the procedures require advanced endoscopic skill which would need to be acquired by most endoscopic practitioners outside of academic institutions. Such skill adaptation can take a significant amount of time, which will limit adoption of the procedure by the physician community. A further issue is that there is a limitation on the size of the anchors and devices which can be placed in the stomach because the endoscope has a maximum permissible size.

Percutaneous Endoscopic Gastrostomy (PEG) refers to a procedure in which a gastrocutaneous tract is created using a percutaneous procedure (see below for definition). A recent update of the procedure can be found on the Society of American Gastrointestinal Endoscopic Surgeons (SAGES) website, and is incorporated herein by reference. Briefly, the procedure involves insufflation of the stomach with and under visualization with an endoscope. A small incision is made in the skin and a needle is advanced into the stomach (the stomach sits just under the abdominal wall when insufflated) under endoscopic visualization. A feeding tube is then placed over the needle to create a gastrocutaneous tract with the feeding tube inside the tract with the needle subsequently removed. The feeding tube is secured with an external bolster to creates a tubular tract from outside the patient through the skin of the abdominal wall and residing inside the stomach. Over the ensuing weeks, a permanent tract evolves between the stomach mucosa and epithelium of the skin, after which, the bolster can be removed without consequence. When the feeding tube is to be removed, the gastrocutaneous tract will close on its own as food will preferentially be delivered antegrade (the path of least resistance) to the duodenum, thereby allowing the tract to heal.

SUMMARY OF THE INVENTION

In one embodiment, a gastric restriction system comprising at least one stomach restricting structure is adapted to be implanted in a patient and a sensor which can receive a signal from the stomach restricting structure and which is adapted to be implanted in a patient. The gastric restriction system further comprises a signal generator which receives at least one input signal from the sensor and generates a least one output signal. The gastric restriction system can also comprise a power source. In some embodiments, the gastric restriction system contains a stomach restricting structure which is a band characterized by a diameter. In additional embodiments, the diameter of the stomach restricting system is further adapted to be adjustable when an electrical current is passed the stomach restricting structure. The gastric restriction system can further comprise a stomach restricting structure which comprises an electrically activated material. The gastric restriction system in some embodiments may also comprise a stomach restricting structure which further comprises a thermally responsive material. In some embodiments, the gastric restriction system comprises a thermally responsive material made from a nickel-titanium alloy. The gastric restriction system in further embodiments comprises an electrically activated material comprising electromagnets. In other embodiments, the gastric restriction system further comprises an adjustable gain control which modulates at least one input signal and at least one output signal from the signal generator. In other embodiments, the gastric restriction system further comprises an adjustable gain control which is remotely adjustable. The gastric restriction system in some embodiments comprises at least one stomach restricting structure with one or more transgastric fastening assemblies comprising at least one or more connectors. The gastric restriction system can also comprise at least one or more connectors which are comprised of an electrically activated material.

In another embodiment, a gastric restriction system comprises one or more connectors which are further comprised of a nickel-titanium alloy adapted to decrease in length when a current is passed through the one or more connectors.

In another embodiment, a gastric restriction system comprises a band wherein the band further comprises an electrically activated material. The band further comprises a balloon. In some other embodiments, the balloon further comprises an electrically activated material which in some embodiments is an is a magnetorheologic fluid. In some embodiments, a gastric restriction system further comprises a sensor adapted to detect a physiologic variable. The physiologic variable can be a pressure wave in the esophagus, a pressure wave in the esophagus, a strain placed on the stomach restricting structure, or a stress placed on the stomach restricting structure. In another embodiment, the sensor of the gastric restriction system is adapted to detect movement between various points on the stomach restricting structure. In other embodiments, the gastric restriction system can further comprise a sensor which is adapted to detect food passage and send a signal to the signal generator; the signal generator is adapted to process an input signal and deliver an output signal to at least one stomach restricting structure wherein the output signal is sufficient to increase or decrease the degree of restriction to the flow of food.

In another embodiment, the gastric restriction system further comprises at least one output from a signal generator which communicates with one of: a patient afferent pathway, a patient efferent pathway, a device end-effector pathway, and a patient end-effector pathway. The gastric restriction system can further comprise one or more gain controls which modulate said at least one input signal and said at least one output signal and which is further adapted to be implanted in a patient. In further embodiments, the gastric restriction system further comprises one or more gain controls which are remotely adjustable.

In another embodiment, a gastric restriction device is described which comprises: an expanding structure with a sizing and a shape configured to embrace an internal organ or organ region; an activating port in physical contact with the expanding structure; and an abdominal wall attachment structure. This embodiment can further comprise an activating port which is in physical contact with the expanding structure and an abdominal wall attachment structure. The gastric restriction device can further comprise an electrically activateable element attached to the expanding structure. The gastric restricting structure can further comprise an abdominal wall attachment structure which is a transgastric fastening assembly with one or more anchors and at least one connector and which is adapted for attachment to the abdominal wall. In some embodiments of the gastric restricting structure, the at least one connector and the activating port are part of the same structure. In some embodiments, the gastric restriction device embraces the proximal portion of the stomach, the sizing is between 0.5 cm and 5 cm, and the shape is configured to at least partially surround the proximal portion of the stomach. In further embodiments, the expanding structure of the gastric restriction device further comprises a fixation construct adapted to fix the expanding structure to the proximal portion of the stomach. The fixation construct can be a mechanical construct. The fixation construct can further be adapted to penetrate the serosa but not the mucosa of the internal organ. In some embodiments, the mechanical construct is a connector and anchor structure and in some embodiments the construct further comprises an electrode adapted to stimulate the stomach. In further embodiments, the expanding structure is a balloon and in further embodiments, the balloon is filled with a magnetorheologic material. The expanding structure in some embodiments can further be activated and in some embodiments the expanding structure can comprise a shape memory alloy and in some embodiments, the shape memory alloy is nickel-titanium alloy.

In another embodiment, a gastric restriction device comprises a connector and an anchor adapted to interface with the anterior wall of the stomach and attach to the connector; the restriction device further comprises a posterior anchor attached to the connector and adapted to interface with the posterior wall of the stomach. One or more of the connector, anterior fastener, and posterior fastener is adapted to transmit an electrical current to a region of the stomach. The gastric restriction device further comprises a controller which communicates with one or more of the connector, the anterior anchor, and the posterior anchor. The connector, the anterior anchor, or the posterior anchor of the gastric restriction device can further be adapted to receive a signal from a sensor based control system. In further embodiments, the anterior anchor, the posterior anchor, or the connector of the gastric restriction device is adapted to transmit an electrical current to more than one regions of the stomach through more than one electrical pathway. In some embodiments, the gastric restriction device comprises more than one electrical pathway which is physically connected to the gastric restriction device. In further embodiments, the gastric restriction device is further adapted so that some of the electrical pathways communicate with the gastric restriction device through a wireless communication system. In other embodiments, the gastric restriction system further comprises a power source and/or a controller. In still further embodiments, the gastric restriction device comprises a controller adapted to communicate with an implanted sensor.

In another embodiment, the anterior anchor, the posterior anchor or the connector has one or more components which is biodegradable. The transgastric fastening assembly is further adapted to create a gastric restriction in a patient for a period less than 5 years.

The transgastric fastening assembly can further comprise a signal generator. In some embodiments, the fastening assembly creates a stomach restriction which is reversible upon receiving an electrical signal.

In another embodiment, a transgastric anchor assembly comprising at least one anterior anchor, at least one connector defined by a length and a material and at least one posterior anchor wherein the at least one posterior anchor is adapted to link to one or more anterior anchors through one or more connectors. In some embodiments, the transgastric anchor assembly comprises at least one posterior anchor with a length between 1 cm and 20 cm. The transgastric anchor assembly is further adapted to link to one or more posterior anchors through one or more connectors. In some embodiments, the anterior anchor has a length between 0.5 cm and 20 cm. In further embodiments, the lengths of the one or more connectors is adjustable.

In some embodiments, the transgastric anchor assembly comprises a posterior anchor which is comprised of a combination of a hydrophilic and a hydrophobic material.

In another embodiment, a gastric restriction system comprises at least one stomach restricting structure adapted to be implanted in a patient and a sensor which communicates with the at least one stomach restricting structure and which (the sensor) is adapted to be implanted in a patient. The gastric restriction system can further comprise at least one stomach restricting structure which is adapted to transmit an electrical current to a patient afferent pathway. The patient afferent pathway can be the vagus nerve. In some embodiments, the gastric restriction system transmits an electrical current to the patient afferent pathway as a response to a signal provided by the sensor. In further embodiments, the gastric restriction system is further adapted to transmit an electrical current directly to the muscles of the stomach. In some embodiments, the gastric restriction system is a restricting band. In another embodiment, the stomach restricting structure is a transgastric fastening assembly. In some embodiments, the sensor is configured to sense patient feeding and the transmission to the stomach is sufficient to induce a feeling of satiety. In other embodiments, the transmission is sufficient to induce a sensation of nausea and/or vomiting. The sensor of the gastric restriction system can further be configured to sense patient feeding and said transmission can be adapted to induce a sensation of nausea and/or vomiting. In other embodiments, the sensor is configured to sense a strain on at least one stomach restricting structure and the gastric restriction system is further adapted for communication with the muscles of the stomach or the afferent fibers of the vagus nerve.

In another embodiment, a gastric restriction device comprises a transgastric anchor assembly comprising an anterior anchor, a posterior anchor, and a connector, one or more of which is further adapted to conduct an electrical current. The device can further be adapted for implantation in a patient. The gastric restriction device can further comprise a device afferent pathway. In some embodiments, the gastric restriction device can further comprise a device afferent pathway or a device end-effector pathway. In additional, or in alternative embodiments, the gastric restriction device can further comprise a device efferent pathway. In some embodiments, device efferent pathway changes a state of the device itself (device end-effector pathway). In other embodiments, the device-efferent pathway further transmits a signal to a patient afferent pathway which in some embodiments, is the vagus nerve, and in other embodiments, is a retroperitoneal structure. The device efferent pathway of the gastric restriction device can also communicate with a patient afferent pathway which in some embodiments is a cutaneous pathway. The controller of the gastric restriction device can be programmed to send an electrical signal to the anterior and posterior anchors simultaneously or in a pattern where either the anterior or posterior anchor is activated at any one time.

In some embodiments, gastric restriction system further comprises a device afferent pathway which in some embodiments can be a sensor adapted for communication with a controller. The sensor can be a strain gauge which detects tension resulting from a force pushing apart the posterior and anterior anchors. The sensor can be an induction coil which senses movement between the anterior and posterior fasteners. The gastric restriction device can also comprise a device end-effector pathway adapted to receive input from the controller. The end-effector can be an electrically responsive material, or it can be a nickel-titanium alloy such as nitinol. The device end-effector pathway can respond to an electrical signal generated as a result of patient feeding or food flowing through the restriction device and the nickel-titanium material can be activated to change the degree of gastric restriction.

The gastric restriction device can further contain one or more gain controls and in some cases, the controls can communicate with a device external to the patient through a wireless pathway.

In some embodiments, the gastric restriction device further comprises one or more gain controls which dictate the response of the device end-effector pathways to the controller output. In some embodiments, the gain controls are adjustable with a wireless transmitter from a region external to a patient.

In another embodiment, a gastric restriction system comprising an adjustable stomach restricting band which is adapted to be implanted in a patient, a physiologic sensor which communicates with the adjustable stomach constricting band and is adapted to be implanted in a patient, and a controller which receives an output signal from the sensor and generates its own output signal. The gastric restriction system can further comprise a power source which communicates with the adjustable stomach restricting band and is adapted to be implanted in a patient. The stomach restricting band can further comprise a device efferent pathway. The stomach restricting band can further be adapted to change its diameter when an electrical current is passed through the stomach constricting band. In some embodiments, the adjustable stomach restricting band comprises an electrically activateable material, or in some embodiments, a shape memory material, or in some embodiments, a nickel-titanium alloy. The gastric restriction system can further comprise an adjustable gain control which connects between the input and output signal. In some embodiments, the sensor senses patient feeding and in some embodiments, the sensor senses stress placed upon the restriction system. In some embodiments, the output signal from the gastric restriction system device stimulates one or more device end-effector pathways, a patient afferent pathway, a patient end-effector pathway, and a device efferent pathway. In some embodiments, the restricting band is further adapted to conduct electricity and in some embodiments, the restricting band can directly interface with the muscle of the stomach.

BRIEF DESCRIPTION OF THE DRAWINGS

FIG. 6A illustrates the first step in one embodiment of a method of reducing the volume of the stomach. Shown is a side sectional view of a patient's abdomen with the instrument of FIG. 4 inserted into the patient's abdomen through a laparoscopic port.

FIG. 6B illustrates the next step in one embodiment of a method of reducing the volume of the stomach. Shown is a side sectional view of a patient's abdomen with the instrument of FIG. 4 grasping the posterior wall of the stomach and a needle being inserted into the potential space of the lesser peritoneal sac.

FIG. 18a-d depicts various configurations of constricting bands with various sensor configurations.

DETAILED DESCRIPTION OF THE PREFERRED EMBODIMENT

Anatomy of the Stomach

Figure 1A:
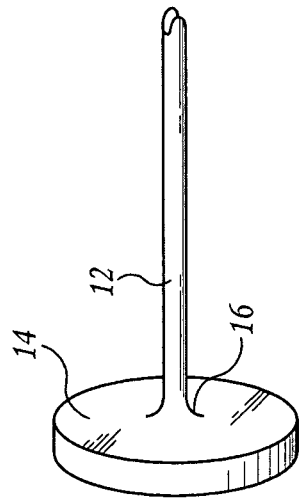
FIGS. 1A-1E are perspective views of embodiments of the posterior anchor and connector.

The region behind the stomach is referred to as the lesser peritoneal sac. It is a potential space between the retroperitoneum and the posterior wall of the stomach. The proximal limit of the lesser sac is the cardia of the stomach and the distal limit is the pylorus of the stomach; the superior limit is the liver and the inferior limit is the inferior border of the stomach. To the left of the midline, the posterior wall of the stomach is generally free from the peritoneal surface of the lesser sac and to the right of the midline, the posterior wall of the stomach is more adherent to the peritoneum of the lesser sac although the adherence is generally loose and the adhesions can be broken up rather easily with gentle dissection.

The stomach is comprised of several layers. The inner layer is the mucosa. The next layer is the submucosa followed by the outer muscular layers. Surrounding the muscular layers is the serosal layer. This layer is important with regard to implants and healing because it is the adhesive layer of the stomach; that is, it is the layer which, when breached, heals with scar tissue formation. Implants adhering to this layer are less likely, or not likely, to migrate into the stomach whereas implants only placed in the mucosal or submucosal layers will migrate. Reference to "stomach wall" or "wall of the stomach" as used herein include the entire thickness of the stomach, including the mucosa, submucosa, muscular layers, and serosa. The "anterior wall of the stomach" is the portion of the stomach closest to the muscular abdominal wall and the "posterior wall of the stomach" is the part of the stomach closest to the retroperitoneum.

"Transgastric fastening assembly" or "fastening system" refers to a permanent or semi-permanent implant and comprises at least one posterior anchor, at least one anterior anchor, and a connector to couple the posterior and anterior anchors. "Fastener" and "anchor" have their ordinary meaning and are used interchangeably in this disclosure. The "connector" can refer to any means of connection including but not limited to a material connection, an electromagnetic or magnetic connection, or a chemical connection. As used herein, a "connector" is a coupler or linker used to materially connect the anterior and posterior anchors. As used herein, the "posterior anchor" is the anchor in a preferred embodiment which is adjacent to the posterior wall of the stomach when deployed. The "anterior anchor" is the anchor in a preferred embodiment which is approximated to the anterior wall of the stomach when deployed.

As used herein and when referring to portions of a surgical instrument, "proximal" refers to the end of the instrument which is closest to the surgeon when the instrument is used for its intended purpose, and "distal" refers to the end of the instrument which is closest to the patient and when the instrument is used for its intended purpose. When used to refer to the gastrointestinal tract, "proximal" is toward the mouth and "distal" is toward the anus.

"Laparoscopic procedure" broadly refers to procedures which require pneumoperitoneum and general anesthesia. "Percutaneous procedure" broadly refers to surgeries which do not require general anesthesia or pneumoperitoneum. These broad terms are mutually exclusive for the purposes of the ensuing invention because the respective procedures require different levels of patient preparation and peri-operative treatments and therefore define specific embodiments. Similarly, endoscopic procedure refers to procedures that are performed entirely with an endoscope. In some descriptions, the terminology "percutaneous means" is used which generically refers to placing a surgical instrument through the skin of a patient and using the surgical instrument to accomplish a surgical task; in this more generic case, "percutaneous means" can be used with or without laparoscopic means and in laparoscopic procedures. Similarly, "laparoscopic means" generically refers to procedures performed under the guidance of an internal camera placed through the abdominal wall (that is, percutaneous means); in this more generic sense, laparoscopy can be used with or without percutaneous methodology though in most cases percutaneous means are a requirement for laparoscopic procedure. Similarly, endoscopic means refers to procedures involving some level of endoscopic visualization but is not completed with the endoscope alone whereas "endoscopic procedure" refers to a procedure performed entirely through an endoscope. "Surgery," "surgical procedure," and "surgically created" have their ordinary meaning and with regard to the inventions herein, is all-encompassing, and refers to laparoscopic surgery, open surgery, endoscopic surgery, and percutaneous surgery.

"Patient afferent pathway" refers to a pathway which transmits a signal to the sensorium of a patient; for example, the vagus nerve carries afferent fibers to the hypothalamus and pain centers of the brain. "Patient end-effector pathway refers to a pathway which directly effects a result in an end-organ; for example, stimulation of contraction in the stomach. Patient efferent and end-effector pathways can overlap and therefore, the terms should not be considered mutually exclusive; for example, stimulation of the stomach likely stimulates some nerve fibers that travel to the sensorium and stimulation of the vagus nerve likely stimulates the stomach. "Device afferent pathway" refers to a pathway which transmits a sensory signal to a restriction device; for example, a sensor which senses food intake transmits its signal to the restriction device through a device afferent pathway. "Device efferent pathway" refers to a pathway which transmits a signal from a restriction device to a separate structure (e.g. a device end-effector pathway described below) or device (e.g. patient afferent pathway, a patient end-effector pathway, or a device end-effector pathway). A "device end-effector pathway" is a signal that directly effects a device state; for example, the connector of a transgastric assembly is shortened or the diameter of a restriction band undergoes a change in its diameter size.

"Exogenous gastric feedback loop" or "exogenous satiety pathway" refer to implantable systems which enhance the biologic pathways which already exist in a patient (the endogenous feedback systems). For example, the VBG and the Lap-Band™ both "tell" the patient that he/she is "full," and consequently to stop eating. That is, they induce a feeling of satiety (through dilation of the stomach proximal to the device) earlier than would otherwise be felt by the patient (this is an example of an endogenous satiety pathway). Exogenous or enhancement of these pathways refers to embodiments in which the satiety signal can be controlled and/or enhanced. For example, a sensor can be place on a restriction device and then a pathway, such as vagal nerve stimulation, can be activated in response to feedback from the sensor; therefore, satiety is induced at an earlier stage than if the endogenous feedback systems (stomach dilation) were relied upon.

"Gastric volume reducing devices, procedures and systems" and "gastric restriction devices, procedures and systems" have their ordinary meanings and overlap in meaning when the walls of the stomach are brought closer together. In these cases, all volume reducing procedures and restriction procedures which bring the walls of the stomach closer together necessarily overlap in meaning. "Gastric restriction devices" refer generally to any devices which restrict the stomach in some way. Included (but not limited to) are devices such as transgastric fastening assemblies, laparoscopic bands (e.g. the Lap-Band™), and intragastric balloons.

"Constricting bands" or "restricting bands" have their ordinary meaning and also refer to gastric restriction devices which surround the proximal region of the stomach. The constricting bands cause weight loss by restricting the food intake of the patient. In many cases, the restricting bands are adjustable balloons which are adjustable percutaneously by way of a port implanted at the time of surgery. These bands rely on the patient to inform the surgeon about eating habits and discomfort which may limit their utility because the patient can "cheat" themselves. Furthermore, the monthly or so follow up visits are potentially too infrequent to be useful. "Gastric restriction system" refers broadly to the restricting devices including both adjustable bands and devices such as transgastric fastening assemblies.

Transgastric Fastening Assembly

Figure 1C:
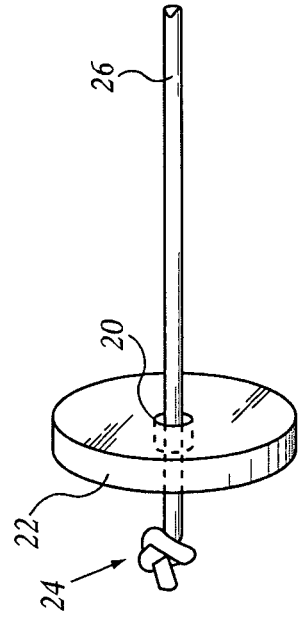
Figure 1E:
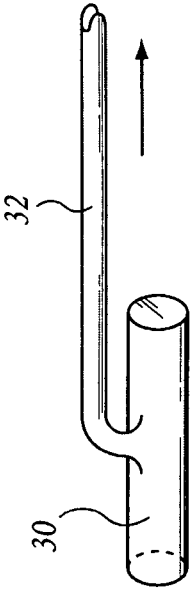
Figure 1B:
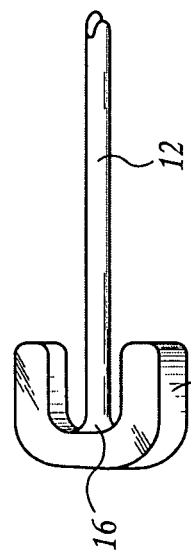

Referring to FIGS. 1A and 1B, one embodiment of the posterior anchor 14 and connector 12 are shown in a deployed configuration (FIG. 1A), and reduced profile configuration (FIG. 1B). The connector 12 is preferably made of a flexible, biocompatible polymer, but it can be made from various kinds of suitable biocompatible materials known to those of skill in the art including metals, such as titanium and platinum, metal alloys, such as stainless steel, nickel-titanium, and cobalt-chromium, man-made polymers, such as polyurethane, silicone elastomers, polyglycolic acid, polylactic acid, poly (c-caprolactone), polyvinylidene fluoride (PVDF), PTFE, FEP, polypropylene, or natural fibers such as silk; bioartificial materials include allogenic and xenogenic collagen based products. These materials can be used singly or in combination (when the connector has two distinct components as opposed to one). For example, one portion of the connector may be bioabsorbable and another portion of the connector may be permanent; or, one part of the connector may be a sensor or active component, and the other part a coating. The connector can be continuous or discontinuous. The connector 12 can vary in thickness, shape, and rigidity. For example, in the embodiment shown in FIG. 1A, the connector 12 is substantially rod-shaped, with a circular cross-section, and is flexible. Those of skill in the art will recognize that the cross-section of the connector can be any of a number of shapes, such as square, hexagonal, oval, etc. In other embodiments, the connector 12 is thin and flexible, such as a surgical suture, and in still others it is rigid. The connector can have a thickness ranging from 100 microns (e.g. suture) to several millimeters depending on the application. Although a single connector is depicted as being attached to the posterior anchor, those skilled in the art will recognize that more than one, or several connectors can be connected to the anchor at different points on the anchor or as a combination attached to one point on the anchor (e.g. a bundle). In some embodiments, the connector is made from a thermoresponsive material such as a thermoresponsive polymer or metal such as shape memory alloy (e.g. nickel-titanium alloy). In other embodiments, the connector is composed of at least one material which conducts an electrical current through from the anterior anchor to the posterior anchor or from the posterior anchor to the anterior anchor.

In a preferred embodiment, the posterior anchor 14 is made from a biocompatible, radio-opaque, or magneto-opaque semi-rigid polymer; it can also be made from various kinds of suitable materials known to those of skill in the art including metals, metal alloys, plastics, natural materials or combinations thereof as discussed above in relation to the connector 12. In some embodiments, the anchor is made from a conductive material and in other embodiments the anchor is made from a combination of conducting, non-conducting, and/or semi-conducting materials. The posterior anchor 14 can be solid, or alternatively, can be porous, mesh-like, lattice-like, or umbrella-like. In some embodiments, the anchor contains a potential space on the inside which can be expanded by a fluid (e.g. gas or liquid). In a preferred embodiment, the posterior anchor is porous or has a porous mesh attached to it to encourage fibrous ingrowth such that it becomes permanently attached to the stomach or intestinal wall. Coatings can be added to the anchor to encourage tissue ingrowth; of course, such coatings do not limit the ability for the interior of the anchor to be a potential space for expansion by a fluid. In other embodiments, the posterior anchor is solid and/or treated to discourage tissue ingrowth (e.g. with a silicone coating). In other embodiments, the posterior anchor has a xenograft or allograft material attached to the anchor. In a preferred embodiment, the posterior anchor 14 is disc-shaped, but those of skill in the art will recognize that other embodiments are possible, such as those shown in FIGS. 1C and 1D, or disclosed in U.S. Patent Application Publication No. 2004/0122456 which is herein incorporated by reference; note particularly the description of anchor structures. The posterior anchor, in other embodiments, can be rectangular or diamond shaped. The posterior anchor can also be bioabsorbable in whole or in part in some embodiments. The largest dimension of the posterior anchor can range from less than 1 mm to about 15 cm depending on the application and the manner in which it is implanted (see below). In the case where the posterior anchor is a disc shape, the diameter is considered the largest dimension.

In the embodiment shown in FIGS. 1A and 1B, the connector 12 is fastened to the posterior anchor 14 at an attachment point 16 which is preferably a permanent, e.g. welded or molded, connection. Such a weld or connection can comprise, for example, a thermoformed polymer, a metallic weld, or a molded or other integral structure. In a preferred embodiment, a biocompatible thermoformed polymer is used because of its flexibility and ability to yield to the continuous motion of the stomach. More preferably, the connector and posterior anchor are produced as a single, continuous structure (e.g. through an injection molding process).

Other suitable means of fastening the connector to the posterior anchor are also contemplated and do not necessarily result in a connector and posterior anchor becoming permanently attached. For example, in one embodiment shown in FIG. 1C, one end of the connector is passed through a hole 20 near the center of the posterior anchor 22, and a stop 24, such as a knot or enlarged molded region, is formed on the end of the connector to prevent its passage back through the hole in the posterior anchor. In this embodiment, the posterior anchor 22 can be free to move along the length of the connector 26, but is prevented from being removed from one end of the connector by the stop 24.

In the embodiment shown in FIGS. 1A and 1B, the posterior anchor 14 preferably has a deployed configuration (FIG. 1A), and a reduced profile configuration (FIG. 1B). The posterior anchor 14 can be deformed to a folded configuration wherein its profile is reduced to facilitate insertion of the anchor through a laparoscopic port or through the walls of the stomach or other tissue as described in more detail below. In one embodiment, the posterior anchor 14 is made of a semi-flexible material having shape memory, so that once the anchor is deployed within the patient, it will return to its original shape shown in FIG. 1A, preventing it from being easily pulled back through the tissue. Preferably, the posterior anchor is inflatable in place of, or in addition to, having shape memory, which allows for a much larger deployed profile relative to its undeployed profile (see below). In some embodiments, the shape memory is activated by passing a current through the material. In some embodiments, the posterior anchor contains an intrinsic magnetic, ferromagnetic, electromagnetic, piezoelectric, paramagnetic, magnetorheologic, or other electrically or thermally adjustable material and can apply a force to another part or portion of the anchor assembly. In some embodiments, the posterior anchor contains electrodes placed at the surface of the material such that they integrate with the organ they contact (e.g the stomach).

Figure 1D:
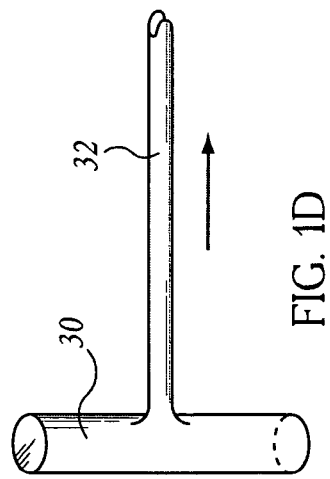

FIGS. 1D and 1E show an alternative embodiment of the posterior anchor 30 and connector 32 in a deployed configuration (FIG. 1D) and a reduced profile configuration (FIG. 1E). In this embodiment, the posterior anchor 30 is elongated, having major and minor dimensions, and preferably having a rod or bar shape. By aligning the connector 32 substantially parallel to the posterior anchor 30, its profile is reduced to facilitate insertion of the anchor through the walls of the stomach or other tissue. When the anchor leaves its surrounding sheath (see below), tension on the connector 32 in the direction of the arrow in FIG. 1E will urge the posterior anchor 30 into a substantially perpendicular orientation relative to the connector 32, as shown in FIG. 1D, preventing it from easily being pulled back through the tissue. The connection between the posterior anchor 30 and the connector 32 can be hinged. Alternatively, the connector 32 can be made of a semi-rigid material which is permanently connected or welded to the posterior anchor 30. If the connector is deformed to a bent position, shown in FIG. 1E, it will return to its original straight shape shown in FIG. 1D once the anchor is deployed within the patient, preventing the posterior anchor from easily being pulled back through the tissue. This anchor 30 can be inflatable as well, which allows for a much larger deployed profile relative to its undeployed profile.

Figure 1F:
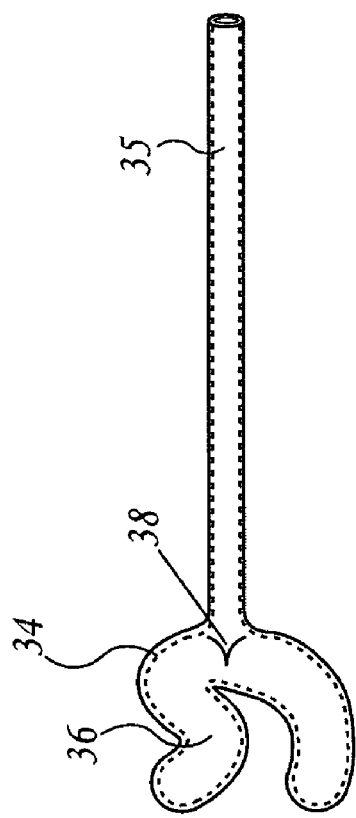
FIGS. 1F and 1G are side views of an inflatable embodiment of posterior anchor and connector.
Figure 1G:
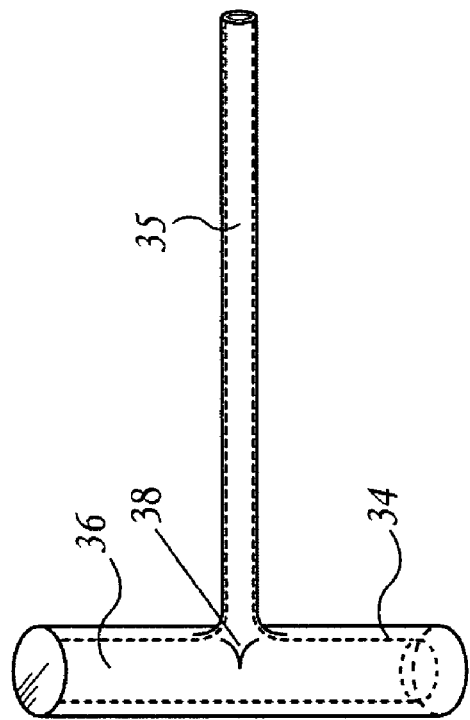

In a preferred embodiment, shown in FIGS. 1F and 1G, the posterior anchor is inflatable. The anchor has an inflatable disc-shaped body 34 which is readily deformable when in its reduced profile (e.g., uninflated) configuration as shown in FIG. 1F. In the preferred embodiment, the posterior anchor body 34 is disc-shaped, but those of skill in the art will recognize that other embodiments are possible, such as those shown in FIGS. 1C and 1D, or in which the inflatable anchors are square shaped, rectangular, or amorphous, or have a shape disclosed in U.S. Patent Application Publication No. 2004/0122456 which is herein incorporated by reference; note particularly the description of anchor structures. The body can be inflated with a substance delivered through a hollow connector 35. When the interior space 36 of the anchor body is inflated, the anchor assumes its deployed configuration shown in FIG. 1G. Once the body is inflated, it can become substantially less compliant yet remain soft and pliable. The anchor can be inflated from its reduced profile to its deployed profile. The size of the reduced profile can be less than 1 cm or less than 5 mm and the size of the deployed profile can range from 1 cm to greater than 5 cm or greater than 10 cm.

The inflatable posterior anchor can have a valve 38 located between the anchor body 34 and the connector 35. Alternatively, the valve is located in the portion of the connector located outside the patient, the valve (e.g. stopcock type valve) being controlled by the operator until the anterior anchor is placed (see below). In this alternative embodiment, the filling substance is trapped in the posterior anchor after the anterior anchor is deployed and the connector is cut and sealed, preferably flush with the anterior anchor (see below). The filling substance can be a gas, liquid, or material which changes phase with time (i.e. it may harden, cure, polymerize, or become a gel with time). Other materials such as magnetorheologic fluids (for example, magnetic particles immersed in an oil) can be used as well and such fluids would interface with the electrical systems described below. Preferably, the surface of the posterior anchor adjacent to the posterior wall of the stomach has a mesh fixed to it to encourage tissue ingrowth. In some embodiments, part or all of the anchor material is comprised of a biodegradable material.

In some embodiments, the anchor assembly and in particular the posterior anchor and connector combination are used for "extragastric volume reduction" of a region of the stomach (see below for more detail). In this embodiment, the posterior anchor can be adapted to be an extragastric restriction device and the anterior anchor-connector system is used for fixation of the device to the abdominal wall. In this embodiment, it may be desirable for the extragastric restriction device to have a shape that conforms to an area of the stomach such as the GE junction. The connector can serve as a conduit to fill the extragastric balloon and can further be equipped with a valve to fill the extragastric balloon and prevent leaking of its contents. The transverse width of the GE junction is typically 0.5 cm to 10 cm in almost the entire population and 1 cm to 5 cm in the majority of the population. The extragastric balloon should be shaped such that it can surround 180-270 degrees of the GE junction or from 90 degrees to 360 degrees. In some embodiments, the balloon can completely surround the GE junction and in these embodiments, the balloon can be continuous or discontinuous.

Figure 1J:
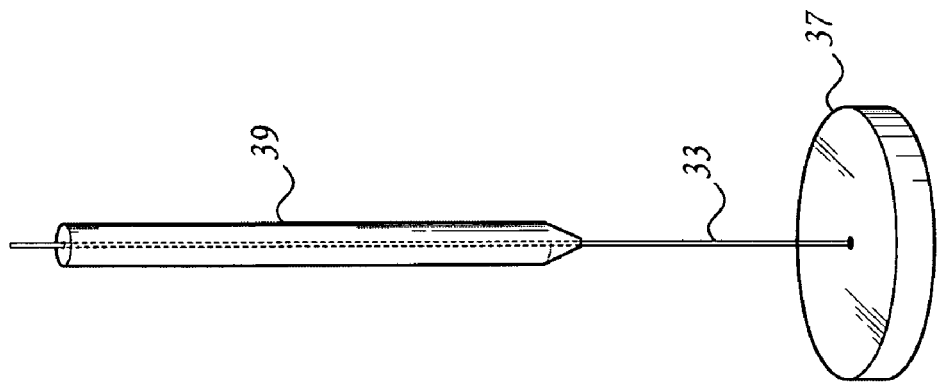
FIGS. 1H, 1I, and 1J are views of suture-connector—posterior anchor combinations in which the connector is separable from the posterior anchor.
Figure 1I:
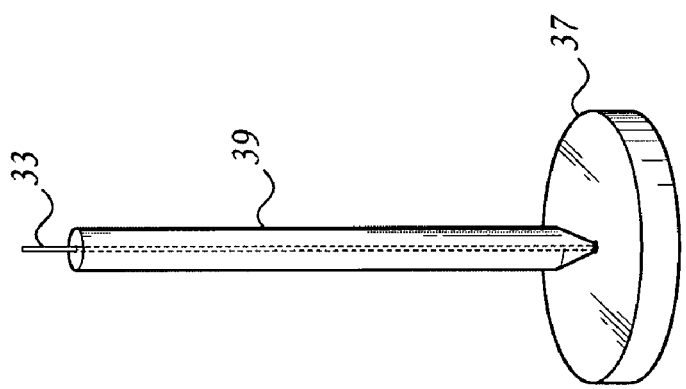
Figure 1H:
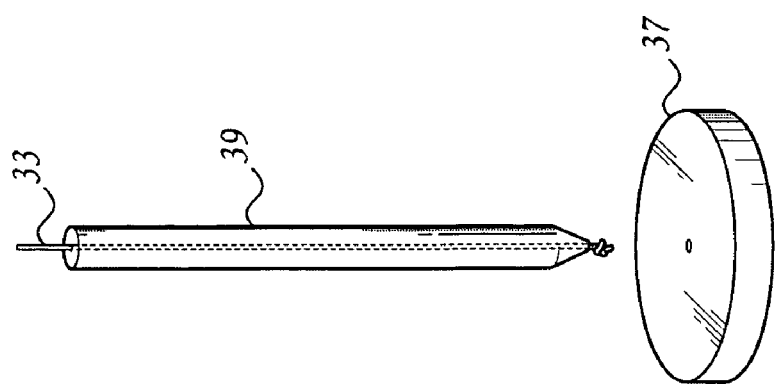

FIG. 1H depicts another embodiment of posterior anchor of the current invention. The posterior anchor 37 and the connector 39 are separable in this embodiment. In one embodiment, the first connector has an inner diameter with a second connector (e.g. a suture) traveling through its lumen. A second connector 33 is disposed within the first connector 39. The second connector 33 can be one or more sutures for example. This fastening assembly would be used in a laparoscopic procedure where the connector 39 would be placed through an organ before engaging the posterior anchor 37. In some embodiments, the posterior anchor can be as large as the width of the organ (e.g. 8-10 cm in the case when the organ is the stomach). In some embodiments, the anchor 37 can be as small as 5 mm or 1 cm. The anchor 37 can also be adapted to accommodate several connectors (FIGS. 15c-d) rather than one connector at a time. The first connector 39 is adapted to engage the posterior anchor 37 after passing through tissue (e.g. the stomach). After contact between the outer connector 39 and the posterior anchor 37, the outer connector 39 is removed, leaving the inner connector 33 (e.g. the suture or sutures) attached to the posterior anchor 37 (FIG. 1J). The connection of the suture to the posterior anchor is accomplished by any mechanical means well known to those skilled in the art.

Figure 1K:
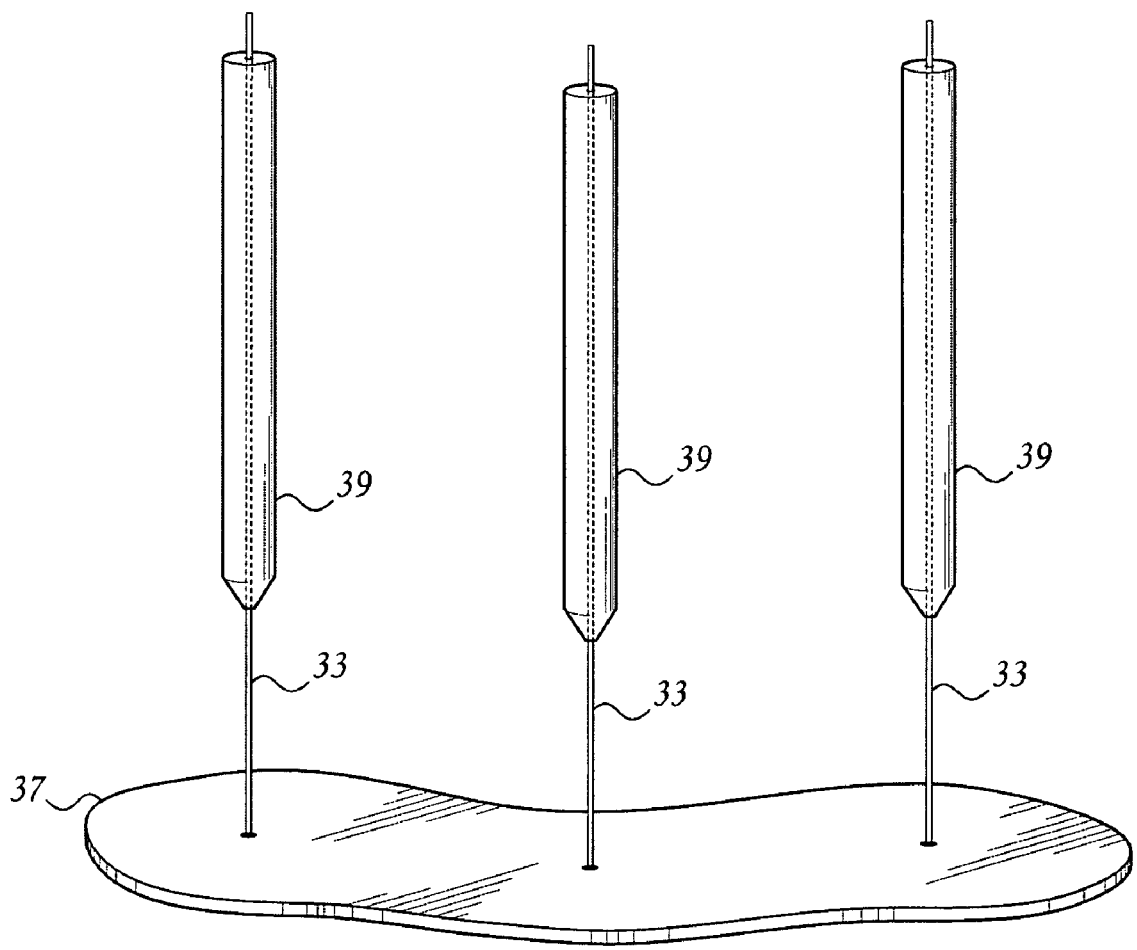
FIG. 1K is a depiction of the continuous form of a posterior anchor.
Figure 1L:
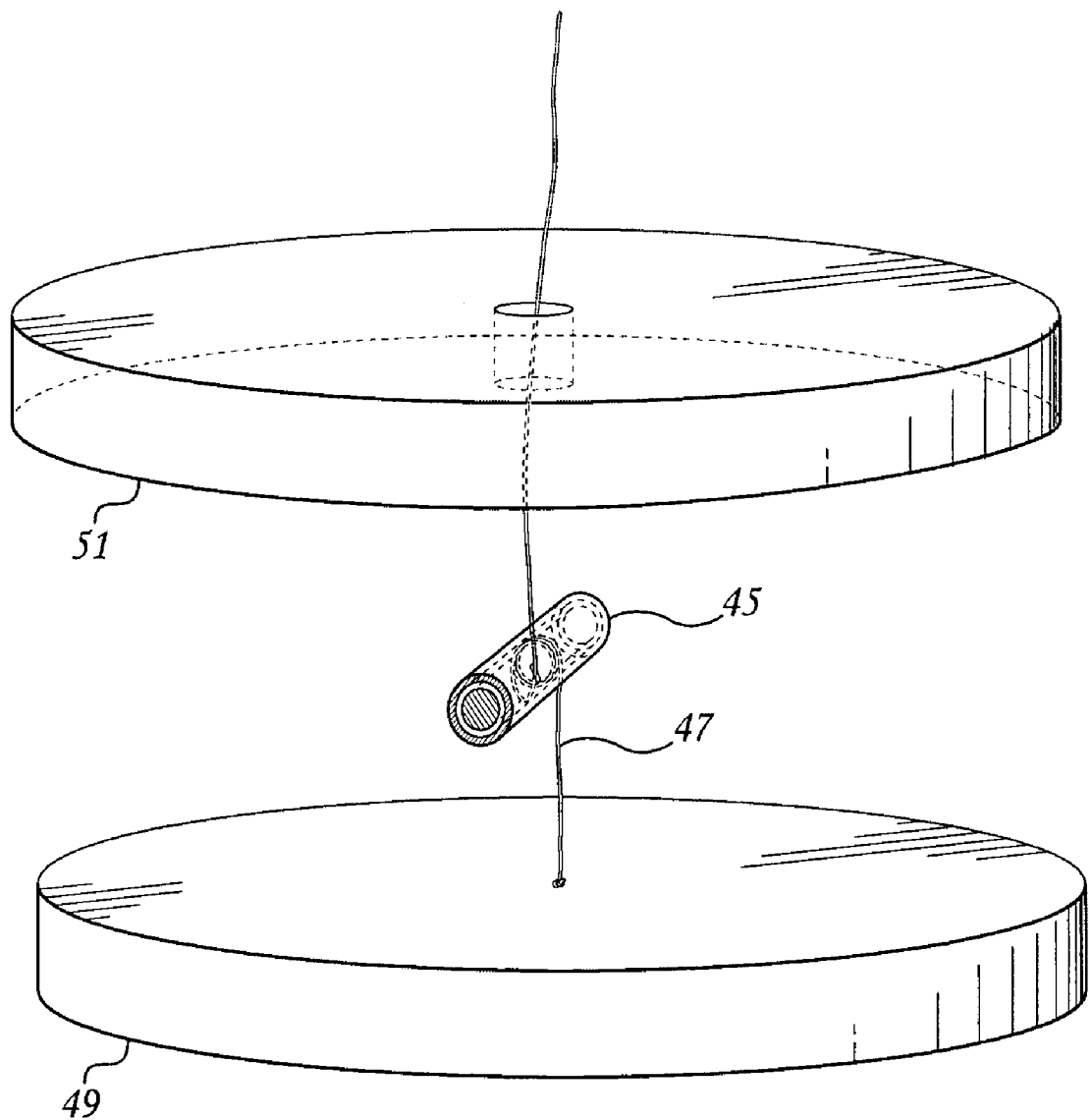
FIG. 1L is a view of a connector-anchor combination in which the length between two anchors is adjustable.

FIG. 1L depicts another embodiment of the current invention in which the connectors 47 in this embodiment are configured so that their length or lengths is/are adjustable. In an example of this embodiment shown in FIG. 1L, the connector is split (e.g. two sutures are used). The housing 45 is attached to one half of the connector 47 and this half of the connector is attached to the posterior anchor 49. Within housing 45, the connector 47 can be shortened (and the tension between the two anchors increased) by turning inner cylinder 48 which changes the distance (and the tension on the connector) between the two anchors 49, 51. In another embodiment, a solenoid based motor system can adjust the pulley and change the length of the connector 47. Such adjustment can be done with an endoscope or can be done automatically with a wireless based transmitting system; in this embodiment, the implanted anchor assembly will have an integral source of power and a controller system. The adjustment can be done after (e.g. days, months, years) implantation of the fastening system within an organ such as the stomach.

Although FIGS. 1a-l depict a single connector contacting the posterior anchor, those skilled in the art will recognize that more than one connector can be used to contact the posterior anchor. The more than one connector can be placed in any arrangement along the posterior anchor (e.g. in a row, in a pattern along the perimeter, or concentrated in the center).

The more than one connector can be bundled and attached in one place on a second anchor or in multiple points on a second anchor.

Other methods of introducing adjustability of the transgastric anchor assembly exist as well and are useful in some embodiments. For example, the suture can be produced from a material such as nickel-titanium alloy, the tension of which can be adjusted with an electrical current or other means of introducing a temperature increase in the alloy. In some embodiments below, the tension of the nickel-titanium alloy can be adjusted depending on an input parameter such as for example, the output from a sensor integral to a gastric restriction device (see below for more detail). In another embodiment, a nickel-titanium alloy is a novel component of a restricting band such as the Lap-Band™ (sec below) or an extragastric restriction device which does not completely surround the stomach. In some embodiments, both a transgastric assembly and a restricting band are implanted in the patient and in some embodiments, the transgastric fastening assembly has an adjustable nitinol connector and in other embodiments, the restricting band has a nitinol ring which is adjustable via electrical means. In some embodiments both the transgastric anchor and the restricting band both have adjustable nitinol components.

In any of the embodiments above, the connector can serve as a sensor to detect the tension imposed on it by the two fasteners moving in opposite directions. In embodiments where the connector serves as a sensor, the connector can be composed of one or more different materials. One of the materials can be a sensor or sensing material and the other serves as a material for mechanical strength. As discussed below, the connector (sensor) can serve as the afferent (device afferent) limb of a feedback loop. The efferent (device efferent) pathway of the feedback loop can be an electrical lead, which communicates with, and stimulates a pathway such as the vagus nerve (patient afferent pathway), a sympathetic pathway such as the celiac plexus, or a device efferent pathway which (for example) can adjust the degree of gastric volume reduction or restriction. When some or all of these efferent (neural and mechanical) pathways are stimulated, a feeling of satiety can be created and controlled in a patient. Such pathways may decrease or eliminate problems with constricting band and stapled gastroplasties because they offer solutions to decrease the amount of pressure applied by the devices to the stomach until the pressure is needed (when the patient is eating for example). Such methods and devices can potentially decrease the problems with erosion and reflux. Furthermore, the adjustment of the device can be taken out of the hands of the patient and controlled by the device and the surgeon. Furthermore, battery power can be conserved by apply electrical stimulation only when the patient is eating.

In an embodiment, the connector (or part of the connector) can take the form of a strain gauge in which a potential is generated which is proportional to the tension (stress) applied to it. The strain measurement in the connector can be transmitted wirelessly or through a wired connection to an effector limb (patient or device efferent pathway) of the circuit or to an external receiver. In other embodiments, the strain measurement is transmitted through a wired circuit (e.g. from the strain gauge directly to the efferent pathway of the feedback loop). In some embodiments, the efferent effector pathway is stimulation of the stomach wall surrounding the fasteners or the stomach wall in a place some distance away from the transgastric fastener assembly such as the peri-pyloric region. Stimulation of a patient end-effector (e.g. the stomach) pathway can be transmitted through the fastener itself or through a separately attached electrode.

In an alternative embodiment, the efferent limb of the feedback loop is an electrical lead which communicates with a cutaneous stimulator to negatively enforce excessive feeding behavior. In this embodiment, feedback to the patient is not necessarily a satiety signal but a cutaneous feedback signal which alerts the patient to an overfeeding state.

The algorithm between the afferent and efferent pathway can be a simple one in which the efferent pathway has an on or off status depending on the level of stimulation from the afferent pathway. Alternatively, the relationship between the afferent and efferent pathways is non-linear. For example, as the strain increases, the efferent signal increases two- three- or fold. If the strain increases further, the efferent signal can increase in an exponential manner (for example, eight to ten-fold). Other patterns are possible as well and these patterns can be programmed into the controller or signal generator and represent the algorithmic aspects of the stimulation system. Nevertheless, the relationship between inputs and outputs of the system can be programmed from a location external to the devices and system (e.g. the surface of the patient or a remote location such as a physician's office).

Figure 2A:
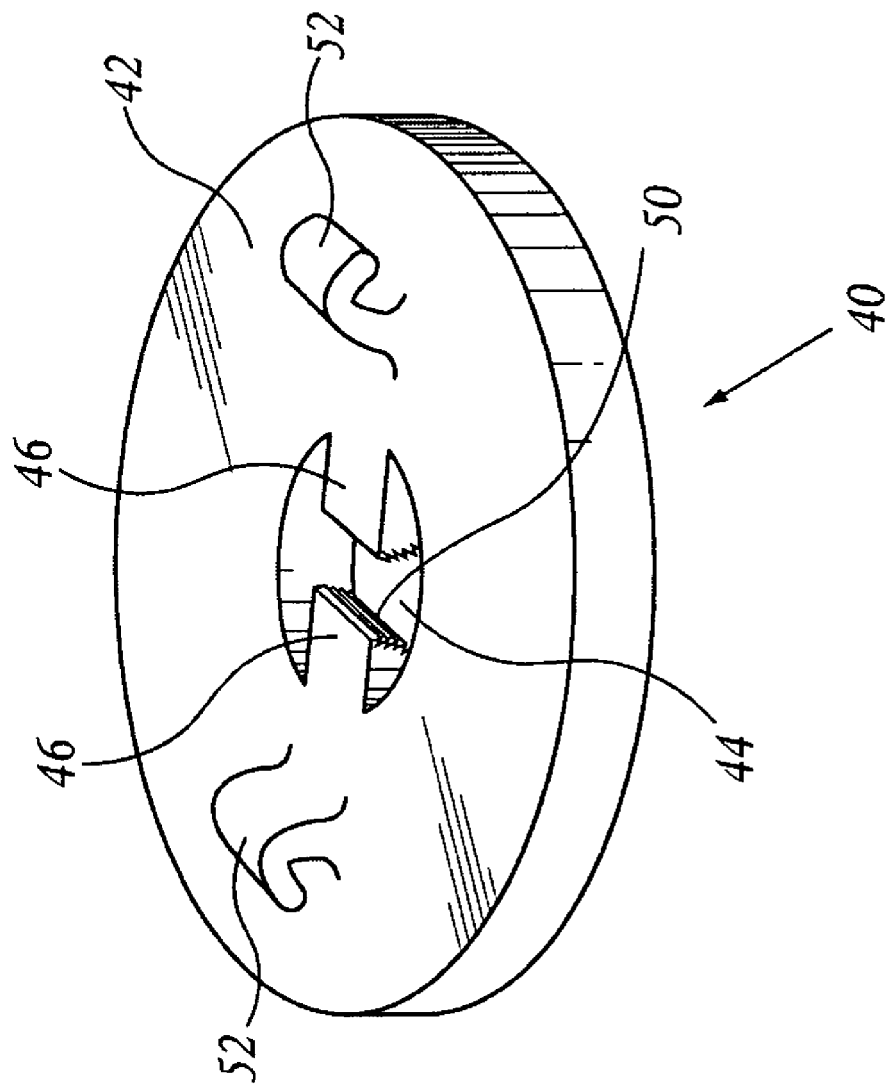
FIGS. 2A and 2B are a perspective view and top view of one embodiment of an anterior anchor, respectively.

FIGS. 2A (perspective view) and 2B (plan view) show an embodiment of the anterior anchor 40. The anterior anchor has a disc-shaped body 42 with a hole or other passageway 44 substantially in the middle of the body. Although the hole is shown in the center of the anchor, those skilled in the art will recognize that the hole can be placed anywhere along the face of the anterior anchor and/or more than one hole can be created in the anchor. Two or more gripping elements 46 project into the center of the hole or other passageway. With respect to the gripping elements, there can be as few as one or more than two. The gripping elements can circumscribe the entire opening or they can be discrete components 46. The gripping elements can be macroscopic as shown in FIG. 2A or they can be microscopic like sandpaper (not shown). The gripping elements may have teeth 50 angled toward the top surface of the anchor. Optionally, two hooks 52, or other graspable recesses, appendages, or structures, are located on the top surface of the anterior anchor. Hooks 52 allow for attachment of a surgical instrument during deployment of the anterior anchor in the patient as described below. Alternatively, there can be none, one, two or more than two graspable recesses, appendages, or structures on the top surface of the anchor. In the preferred embodiment, the anterior anchor body 42 is disc-shaped, but those of skill in the art will recognize that other embodiments are possible, as disclosed in U.S. Patent Application Publication No. 2004/0122456 which is herein incorporated by reference; note particularly the description of anchor structures. The anterior anchor (or the transgastric fastening assembly) can also be wholly comprised of or only partially comprised of one or more magnetic, magnetorheologic, or electromagnetic components. In these embodiments, an electric current is applied to the anchors which either causes attraction of the anchors (e.g. when the anchors contain electromagnets), or results in an increase in the viscosity within the anchors resulting in a resistance to the flow of food (magnetorheologic embodiment). Alternatively, in other embodiments, the anterior anchor (or the transgastric fastening assembly) carries one or more weights within it such that gravity causes the intestinal walls to come together (and provide a resistance to food) as a result of the weights within the anchors.

Figure 2B:
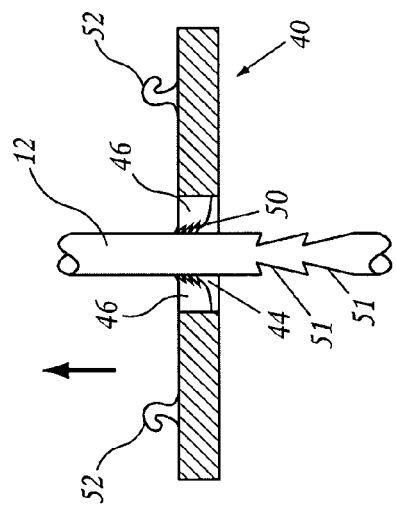
Figure 2C:
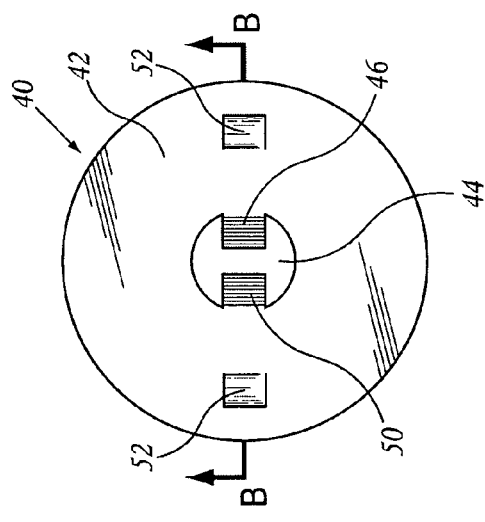
FIGS. 2C and 2D are side sectional views of the embodiment of the anterior anchor of FIGS. 2A and 2B, taken along the line B-B in FIG. 2B, in its deployed and reduced profile configuration, respectively.
Figure 2D:
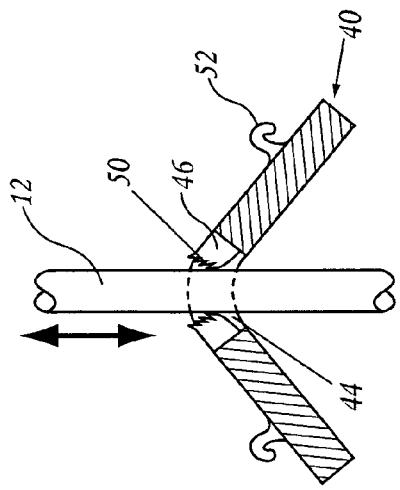

FIGS. 2C and 2D are cross sections of the anterior anchor of FIGS. 2A and 2B, taken along the line B-B in FIG. 2B. FIG. 2C shows the anterior anchor in its deployed configuration with the connector 12 of FIG. 1A passing through the hole or other passageway 44 in the body of the anchor. In the deployed configuration, the gripping elements 46 and teeth 50 engage the connector 12 with sufficient pressure to prevent movement of the anchor along the connector 12 in the direction of the arrow in FIG. 2C, which would increase the distance between the anterior anchor and posterior anchor (not shown). In the case where the connector is a suture, the surface of the suture can be roughened to enable gripping by the anchor. In FIG. 2D, the anterior anchor 40 is in its reduced profile configuration with the connector 12 of FIG. 1A passing through the hole or other passageway 44 in the body of the anchor. Preferably, the anterior anchor is made of a semi-rigid polymer which allows the anchor to be deformed into a substantially folded configuration illustrated in FIG. 2D. When in this configuration, the gripping elements 46 and teeth 50 do not significantly engage the connector 12. This allows movement of the anterior anchor 40 along the length of the connector 12 in the directions illustrated by the arrows in FIG. 2D. Once the anterior anchor is in the desired position along the connector 12, the anterior anchor is permitted to return to the configuration shown in FIG. 2C, and the gripping elements 46 and teeth 50 engage the connector 12, thus preventing movement between the connector 12 and the anterior anchor 40. Importantly as described above in some embodiments, the anterior fastener is slideable along the connector in a reversible fashion. For example, when the fastener is compressed to its undeployed configuration from its expanded configuration, the fastener can once again move (or be moved) along the connector. This feature may be a highly desirable one as it will allow for adjustability after deployment of the fastener because the process can be reversed and the fastener repositioned.

In an alternative embodiment, it is contemplated that the connector 12 can have notches 51, which interact with gripping elements 46 in a ratchet-and-pawl mechanism similar to that used in cable ties, providing a one-way adjustability, in which the posterior and anterior anchors can be moved toward each other, but not away from each other.

Figure 2E:
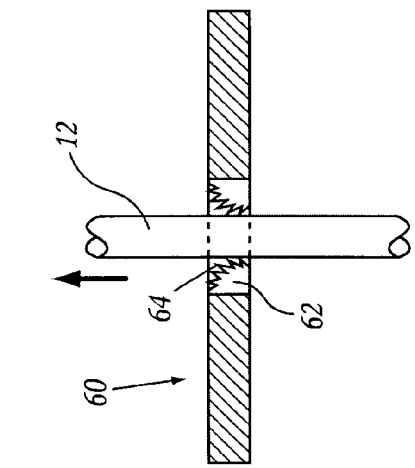
FIGS. 2E and 2F are side sectional views of another embodiment of an anterior anchor, taken along the same line as FIGS. 2C and 2D, in its deployed and reduced profile configuration, respectively.
Figure 2F:
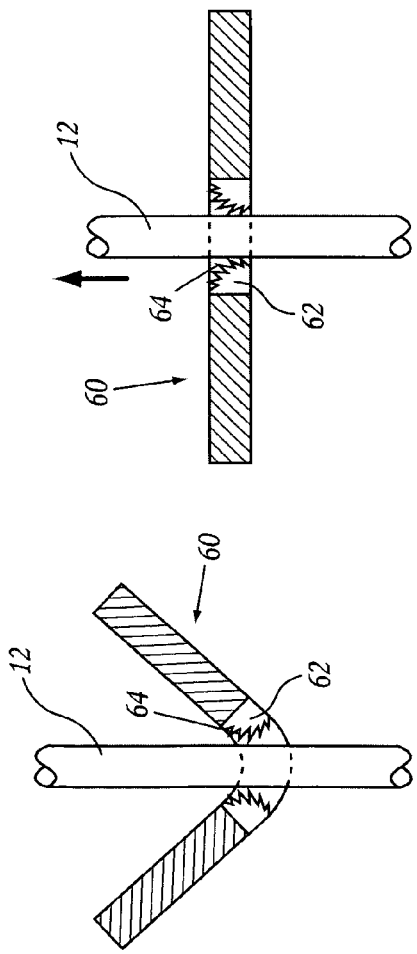

FIGS. 2E and 2F illustrate another embodiment of an anterior anchor 60 which is similar to the one illustrated in FIGS. 2C and 2D. In FIG. 2E, the gripping elements 62 and teeth 64 are oriented so that the anterior anchor can be deformed such that the top surface of the anchor is folded inward as illustrated in FIG. 2F. This is in contrast to the embodiment illustrated in FIG. 2D where the bottom surface of the anchor is folded inward. The teeth 64 in FIG. 2E are angled toward the top surface of the anterior anchor and engage the connector 12 of FIG. 1A such that they prevent movement of the anterior anchor along the connector 12 in the direction of the arrow in FIG. 2E, which would increase the distance between the anterior anchor and posterior anchor (not shown).

Figure 2G:
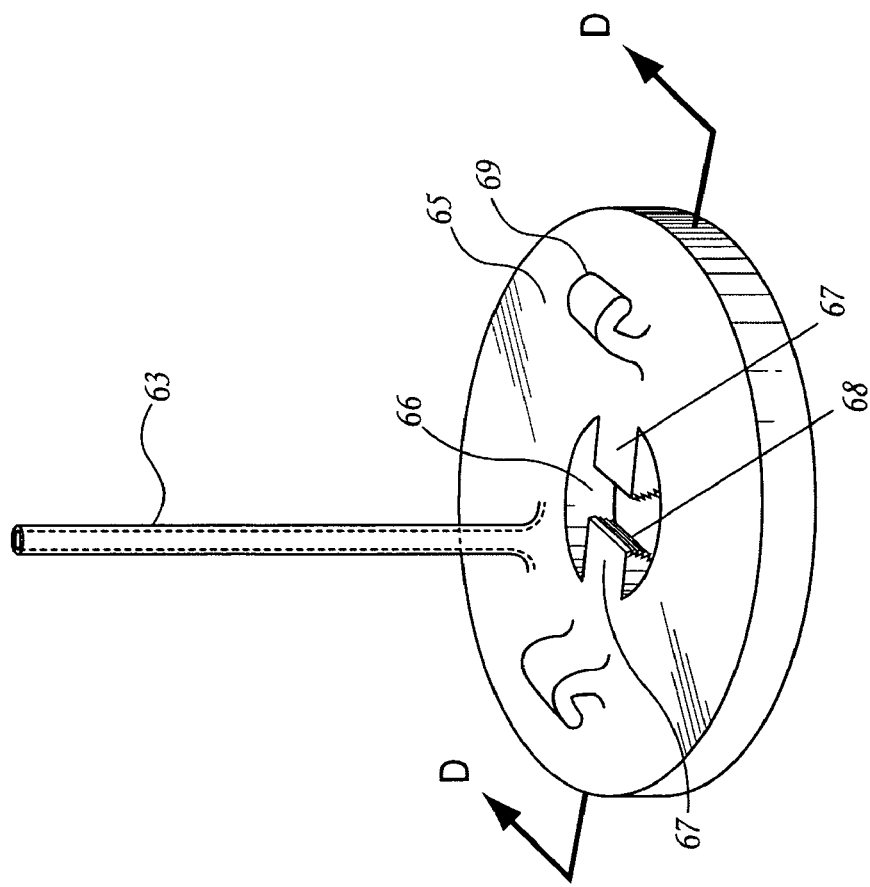
FIG. 2G is a perspective view of an inflatable embodiment of an anterior anchor.

FIG. 2G is a perspective view of a preferred embodiment where the anterior anchor is inflatable. The anterior anchor is inflateable from a reduced state of approximately 5 mm or 1 cm to greater than 5 cm to greater than 10 cm The anterior anchor has a hollow, inflatable disc-shaped body 65 with a hole or other passageway 66 substantially in the middle of the body to track the connector. Two gripping elements 67 project into the center of the hole or other passageway, although there can be as few as one or more than two gripping elements. The gripping elements can have teeth 68 angled toward the top surface of the anchor. Alternatively, in a preferred embodiment, the gripping elements are in the form of a rough surface rather than the protruding elements as shown in FIG. 2G. Such a surface, which may be a sandpaper-like surface, creates enough friction to prevent movement in either direction along the connector. Optionally, two hooks 69 are located on the top surface of the anterior anchor. Hooks 69 facilitate grasping by a surgical instrument during deployment of the anterior anchor in the patient as described below. Alternatively, rather than hooks, there can be one or more graspable protrusions on the body. In yet another embodiment, there are no hooks or graspable protrusions, and the body of the anchor is grasped directly to manipulate the anchor. In another embodiment, protrusions 69 are magnetic or otherwise sticky (e.g. Velcro) in nature to facilitate attachment to a surgical instrument.

An inflation tube 63 is used to inflate and deflate the anterior anchor. This inflation tube may or may not have a valve. In one preferred embodiment, the anterior anchor is filled with gas or fluid through the inflation tube and the fluid is held inside the anchor through an external (e.g. stopcock) valve controlled by the operator. When the inflation tube is cut at the end of the procedure, the inflation line is crimped closed thereby locking the inflating substance inside the anchor. Alternatively, the shears used to cut the inflation line can be metal and an electrocautery current can be applied through the shears and to the inflation line to weld it closed.

Figure 2H:
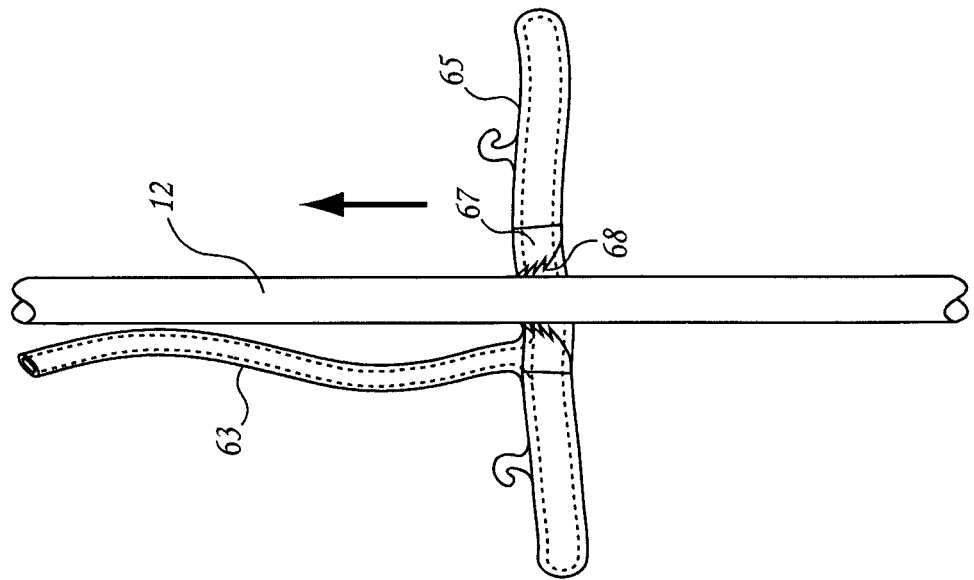
FIGS. 2H and 2I are side sectional views of the embodiment of the anterior anchor of FIG. 2G, taken along the line D-D in FIG. 2G, in its deployed and reduced profile configuration, respectively.
Figure 2I:
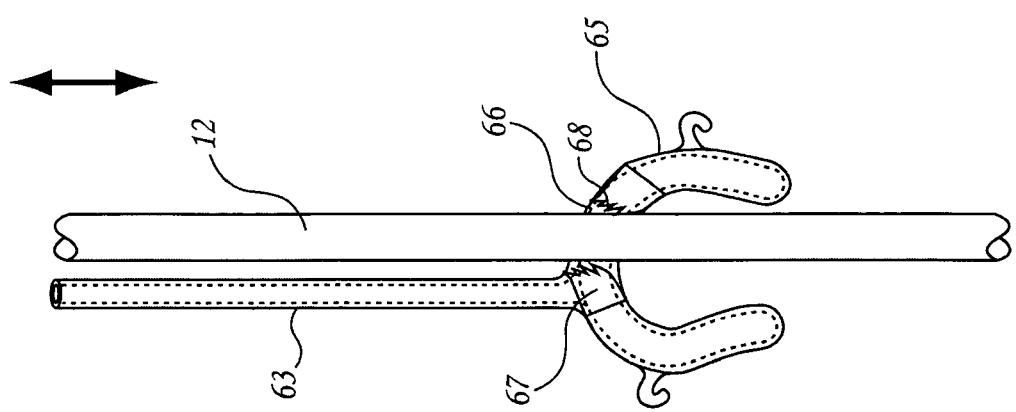

FIGS. 2H and 2I are cross sections of the anterior anchor of FIG. 2G, taken along the line D-D in FIG. 2G. The disc-shaped body 65 is readily deformable when in its reduced profile (i.e., uninflated) configuration as shown in FIG. 2I. The body can be inflated with a substance delivered through the inflation tube 63. When anchor body is inflated, the anchor assumes its deployed (i.e. inflated) configuration as shown in FIG. 2H with the connector 12 of FIG. 1A passing through the hole 66 in the body of the anchor. In the deployed configuration, the gripping elements 67 and teeth 68 engage the connector 12 with sufficient pressure to prevent movement of the anchor along the connector 12 in the direction of the arrow in FIG. 2H, which would increase the distance between the anterior anchor and posterior anchor (not shown). Alternatively, rather than defined gripping elements and teeth, the surface of body which defines the sides of the hole or other passageway 66 can be configured such that when the anchor body is inflated, the sides of the hole or other passageway expand to substantially close off the hole or other passageway and limit movement of the anchor relative to the connector through friction between the connector and the anchor.

In FIG. 2I, the anterior anchor 65 is in its reduced profile (i.e. uninflated) configuration with the connector 12 of FIG. 1A passing through the hole 66 in the body of the anchor. When in this configuration, the anchor body is readily deformable and the gripping elements 67 and teeth 68 do not significantly engage the connector 12. This allows movement of the anterior anchor 65 along the length of the connector 12 in the directions illustrated by the arrows in FIG. 2I. Once the anterior anchor is in the desired position along the connector 12, the anterior anchor is inflated by a filling substance delivered through the inflation tube 63, and the anchor assumes its deployed (i.e. inflated) configuration as shown in FIG. 2H; the gripping elements 67 and teeth 68 engage the connector 12, thus restricting movement of the anterior anchor 65 in one or both directions along the length of the connector 12. The filling substance can be a gas, liquid, or material which changes phase with time (i.e. it may harden, cure, polymerize, or become a gel with time). In some embodiments, the filler substance is a magnetorheologic fluid the viscosity of which can be changed with a magnetic field (e.g. it can be turned on or off).

Figure 3C:
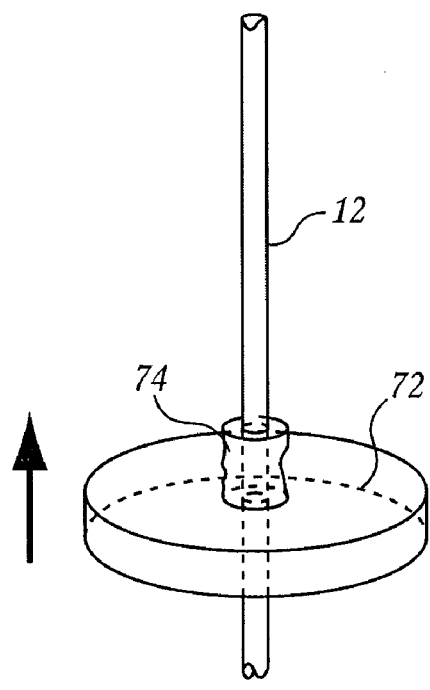
FIGS. 3B and 3C are perspective views of the embodiment of the anterior anchor shown in FIG. 3A in its reduced profile and deployed configuration, respectively.
Figure 3D:
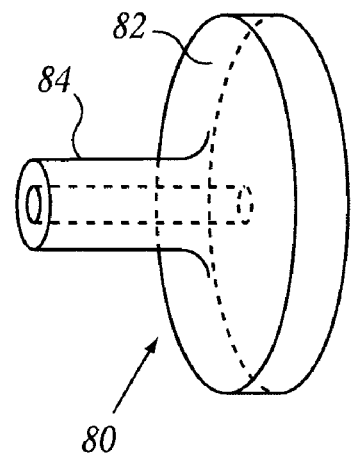
FIG. 3D is a perspective view of another embodiment of an anterior anchor.
Figure 3B:
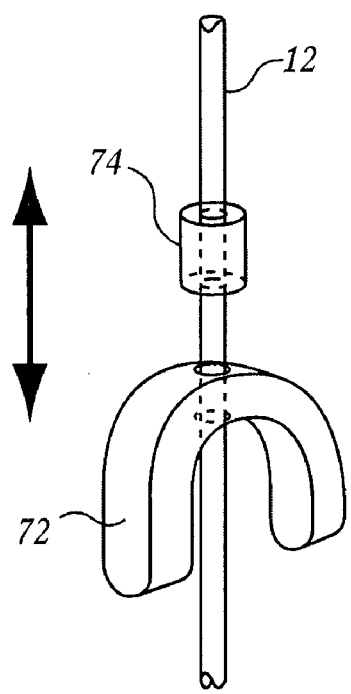
Figure 3A:
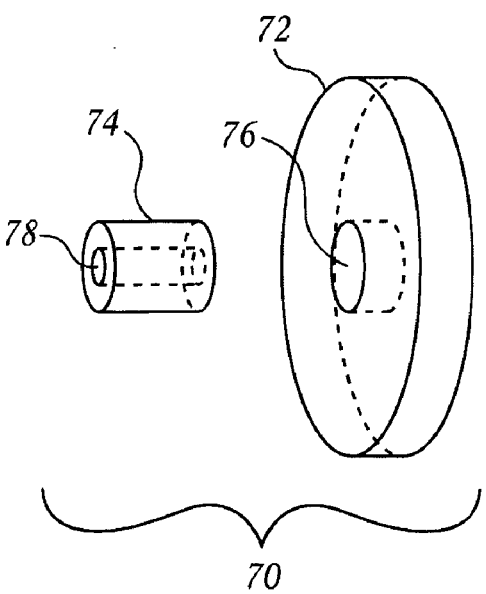
FIG. 3A is a perspective view of another embodiment of an anterior anchor.

FIG. 3A illustrates another embodiment of an anterior anchor 70 consisting of two parts, an anchor body 72 and a readily deformable collar 74. The anchor body and collar have a central hole or other passageway (76 and 78 respectively) through which the connector can pass. Preferably, the anterior anchor body is made of a semi-rigid polymer which can be deformed into a folded configuration with a reduced profile as illustrated in FIG. 3B. Preferably, the readily deformable collar 74 is permanently deformable; i.e., once deformed, it does not return to its original shape. As illustrated by the arrow in FIG. 3B, both the collar 74 and anchor body 72 can move along the connector 12 of FIG. 1A. Once the anchor body 72 is in the desired position, the collar 74 is crushed, such that the collar 74 engages the connector 12 and can no longer move along the length of the connector 12. This prevents the anchor body 72 from moving along the length of the connector 12 in the direction of the arrow illustrated in FIG. 3C, which would increase the distance between the anterior anchor and posterior anchor (not shown). FIG. 3D illustrates an alternative embodiment of the anterior anchor 80, where the anchor body 82 and deformable collar 84 are a single piece.

In a preferred embodiment, the anterior anchor is made from a biocompatible, radio- or magneto-opaque polymer, but it can also be made from various kinds of suitable materials known to those of skill in the art including metals, metal alloys, plastics, natural materials or combinations thereof as disclosed above; the anchor material can also be a biodegradable material. The anterior anchor can be solid, or alternatively, can be porous, mesh-like, umbrella-like or lattice-like. In a preferred embodiment, the anterior anchor is porous, mesh-like, umbrella-like or lattice-like to encourage fibrous ingrowth such that it becomes permanently attached to the stomach wall. Coatings can be added to the anchor, or a mesh material such as polypropylene can be fixed to the anchor surface, such that it touches the anterior stomach wall and encourages tissue ingrowth. In other embodiments, the anterior anchor is solid and treated to discourage tissue ingrowth with materials such as silicone, PTFE, or FEP which are generally hydrophobic and non-reactive. In one embodiment, one side of the anchor is produced from PTFE and the other side of the anchor is produced from polypropylene. In other embodiments, the anterior anchor has a xenograft or allograft material attached to the anchor which can encourage tissue ingrowth. In a preferred embodiment, the anterior anchor is disc-shaped and substantially flat, but those of skill in the art will recognize that other embodiments are possible; for example, the anterior anchor can be elongate and/or continuous and can range in size from 5 mm to 10 cm, in which case, it can traverse the length or width of the stomach.

In some embodiments, the anterior anchors can have electrodes which can communicate electrically with a tissue (e.g. the stomach) after the anterior anchors are positioned in contact with the tissue (e.g. the stomach). The electrodes can pass through the material to communicate electrically with the connector traveling through the anterior fastener. The electrodes can communicate with other effector pathways (e.g. the vagus nerve or the muscle of the stomach) located at different anatomic regions from the anterior fastener.

In any of the above embodiments, the anterior and posterior anchors as well as the connector can have one or more magnets (electromagnetic, paramagnetic, magnetorheologic, or ferromagnetic materials) disposed within or on their surfaces. Such magnet can serve a variety of purposes. In one example, the magnets serve as actuators to forcefully maintain the walls of the stomach together through their inherent and continuous (or discontinuous in the case of an electromagnet) magnetic interaction. In other embodiments, the magnets serve as sensors to sense the amount of food taken in by a patient; in this embodiment, a change in a magnetic field (relative movement of the magnets) is detected as an inductive current and can be correlated to food intake. Such sensing mechanisms are well known in the mechanical arts. In another embodiment, the anchors contain a magnetorheologic fluid which can respond to an electrical current. When stimulated with a magnetic field, the magnetorheologic fluid will undergo a change in viscosity and create a more or less compliant anchor or connector. In this embodiment, once electrically charged, the increase in viscosity will enhance the effect of the anchors in creating restriction or volume reduction (or both) of the stomach (for example).

Multi-Effector Gastric Restriction Structures and Devices

In some embodiments, the transgastric fastening assemblies serve to reduce the volume of the stomach or restrict the entry of food, and in addition, provide for electrical stimulation and/or sensing; furthermore, the gain, or the relationship between an input parameter and an output parameter of the device, can be assigned prior to implantation of the device and/or can be adjusted after implantation of the device. In these embodiments, an electrical signal runs through electrodes in the transgastric fastening assemblies enroute from a sensor or enroute to alter the contraction patterns of the stomach and/or to electrically create a feeling of satiety through one or more afferent patient nervous pathways. Electrical stimulation can enhance or work synergistically with volume reduction and/or the creation of a restriction to flow in the stomach. Thus, fastener assemblies of the present invention can serve as sensing and/or stimulation structures which are useful, for example, in the creation of exogenous satiety feedback loops (see below).

Figure 17A:
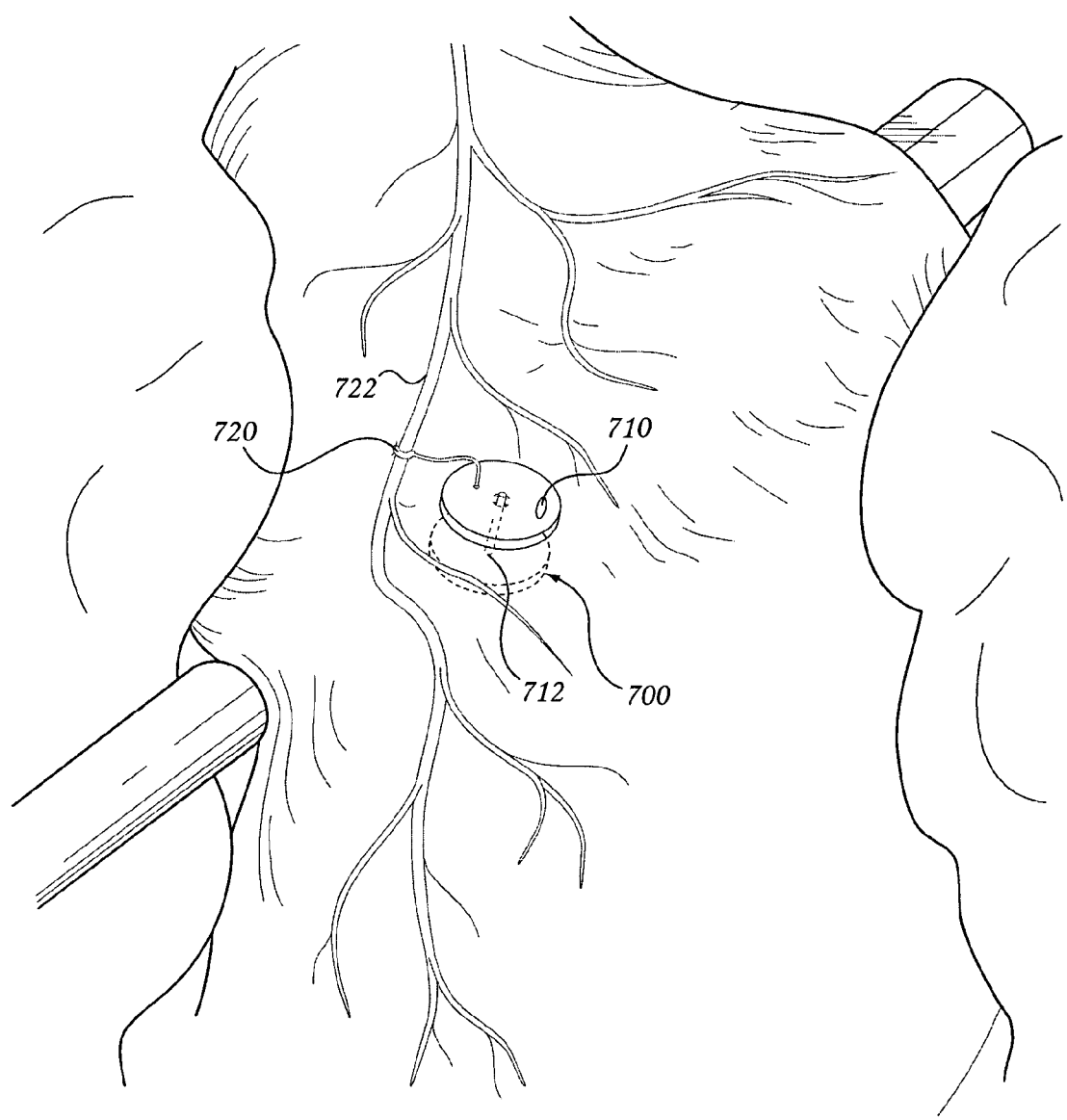
FIG. 17a depicts a transgastric anchor assembly with afferent, efferent, and device end-effector pathways.

In one embodiment, an exogenous gastric feedback loop (see FIG. 17a) is described; a satiety feedback pathway is created surgically by implanting a transgastric fastening assembly 700 wherein the connector 712 is adapted to be a strain gauge (or have a strain gauge as an integral component) and the fastening assembly 700 is further connected via a device efferent pathway 720 to a patient afferent pathway such as the vagus nerve 722. Additional examples of patient afferent pathways include the parasympathetic or sympathetic nervous system which contain patient afferent satiety nerve fibers. In other embodiments, the device afferent pathway (strain gauge sensor) communicates with a device end-effector pathway. For example, if the connector 712 were produced from a shape memory alloy such as nitinol (nickel-titanium), the connector 712 could be induced to decrease in size (generate extra tension) when an electrical current (heat) passes through it. In some embodiments, the strain gauge is located in proximity to the connector but is not the same device as the connector.

In one example, when the strain gauge is activated (e.g. by food passing through the stomach), a message is transmitted to the connector at which point the connector contracts to thereby prevent the flow of food into the stomach. Alternatively (or in addition to) in another embodiment, activation of the strain gauge transmits a signal to the device efferent pathway 720 which in turn sends a signal to the patient afferent pathway 722.

In addition, a gain controller 710 can be provided on the device in one embodiment in order to adjust the relative action (increase in connector tension or degree of stimulation of the vagus nerve) related to the sensing parameter. This device configuration allows the device to apply tension only when necessary (e.g. when food flows into the stomach). In some embodiments, this device configuration can allow for minimal tension to be applied to the device except when required (e.g. when food flows into the stomach). This configuration can save power, may also lead to a decreased tendency for erosion of the devices, and/or may prevent associated complications with the devices such as the Lap-Band™ such as reflux.

Figure 17B:
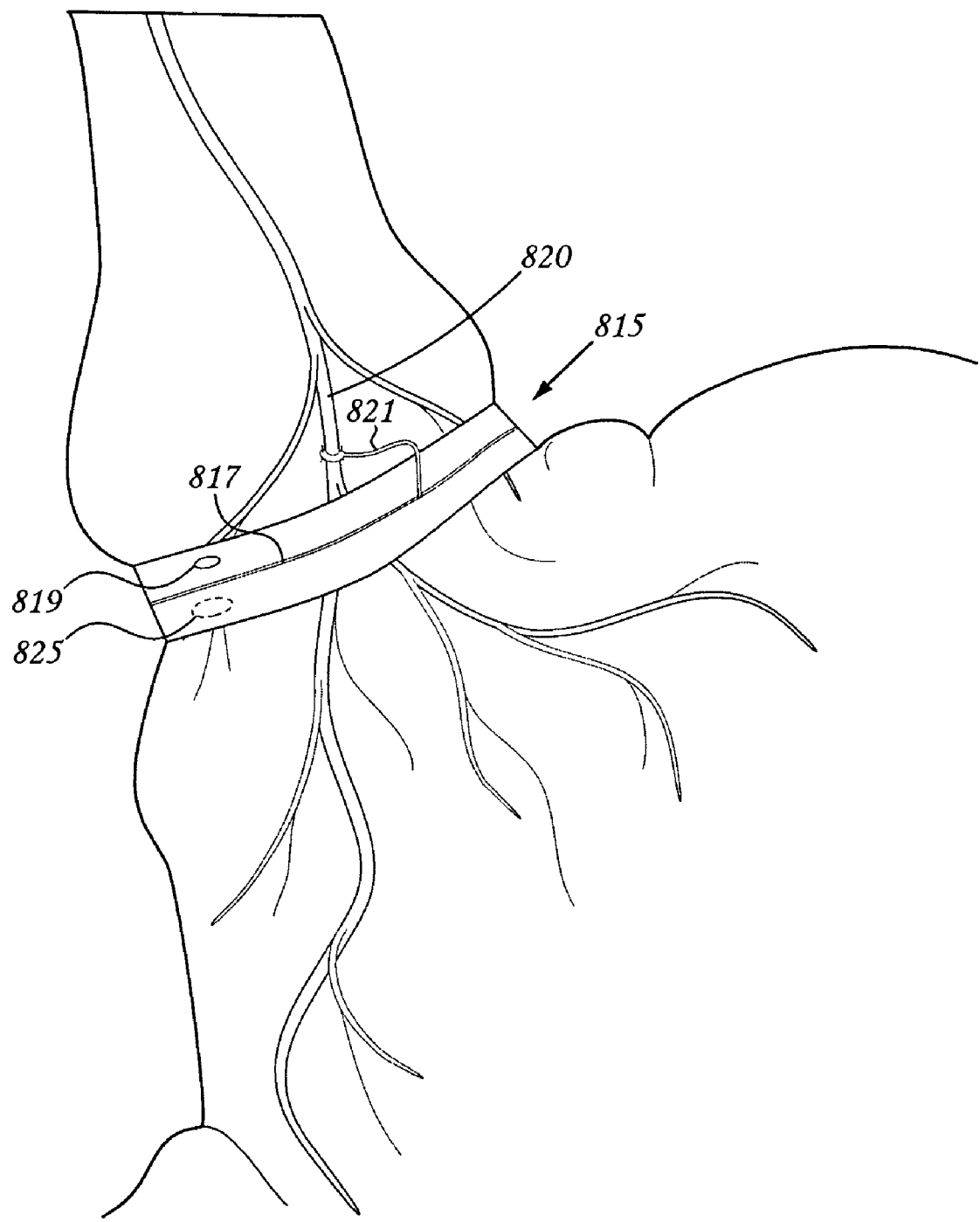
FIG. 17b depicts a constricting band with afferent and efferent feedback pathways.
Figure 18D:
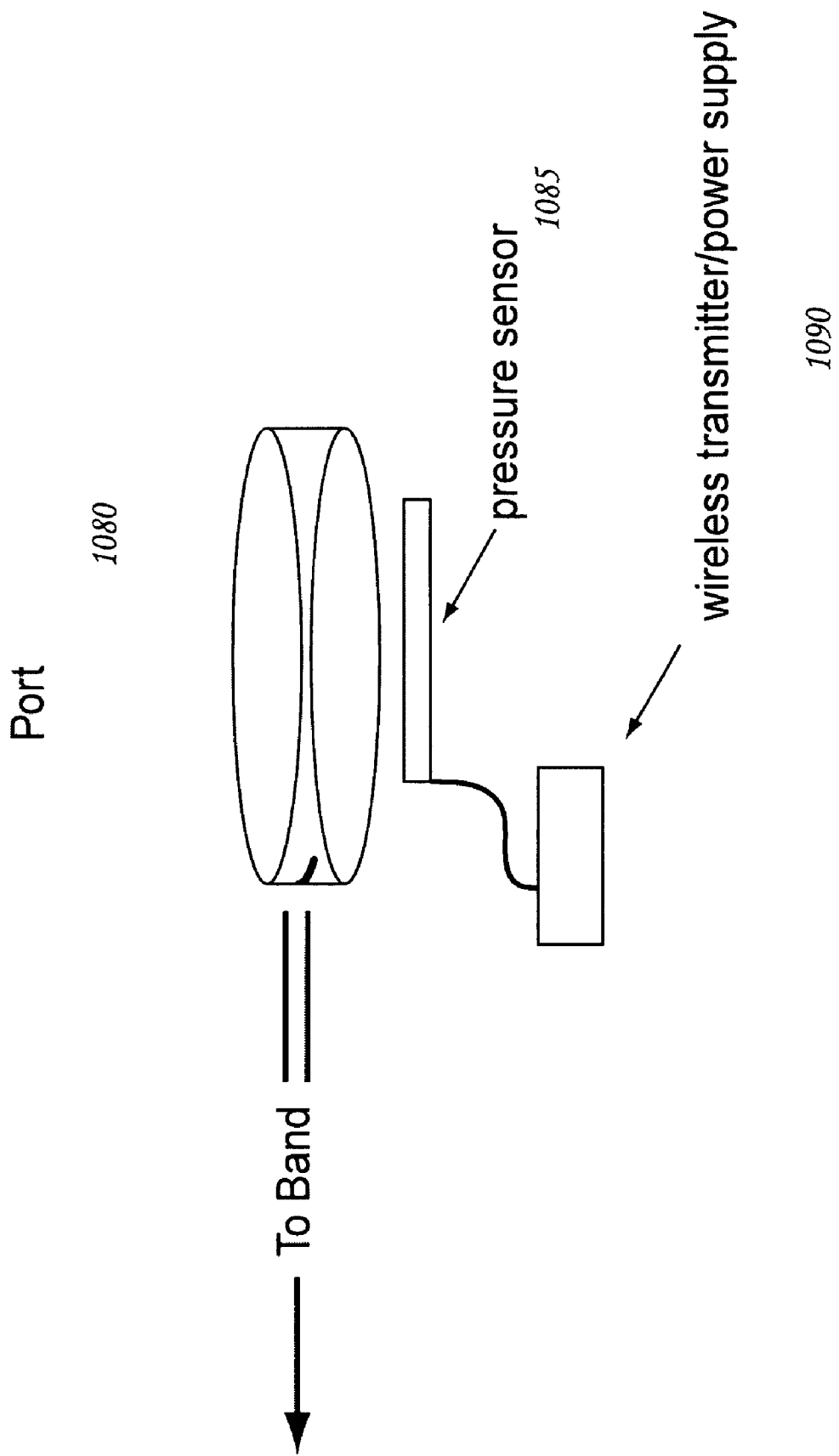

In another embodiment of an exogenous satiety pathway (FIG. 17B), a restricting band type device 815 is placed around a portion of the stomach. As is known to those in the art, the restricting bands typically contain a balloon contained within the outer shell. An additional inventive feature is to endow the restricting device 815 with the ability to sense the circumferential tension or pressure such as, for example, would be created when food flows through the distal esophagus and proximal stomach or when a peristaltic wave approaches the restricting structure. Surgical restricting devices which circumscribe the gastroesophageal junction are well-known in the art (see for example, U.S. Pat. No. 6,464,697); these surgical constricting devices can be further fitted with pressure or volume sensors (e.g. a circumferential strain sensor) 817 in order to create device afferent pathways 817 which respond to the feeding state and simulate (via device efferent pathways 821) patient end-effector pathways 822 (e.g. gastric muscle), device end-effector pathways (e.g nitinol bands), patient afferent pathways such as the vagus nerve 820, or other elements of the visceral nervous system (e.g. sympathetic plexus). Sensor 817 can also communicate directly with a device end-effector pathway; for example, rather than a balloon, the band can be produced from an electrically responsive material such as nickel-titanium. In this embodiment, the material (and therefore the entire constricting band) can be induced to contract when electricity is run through the material, which generates heat to induce a shape change in the material (in this case to generate an increase in tension). In this embodiment, the tension of the band and therefore its restricting ability are controllable through the shape memory material.

In some embodiments, the band also has a balloon which is adjusted by nickel-titanium or by a magnetorheologic fluid (for example), which can also be used to fill the balloon portion of the band. After detecting a feeding state, an electric current passes through the magnetorheologic fluid or through an electromagnet which allow the band to become firmer, more viscous, or less compliant, and thereby more difficult for food to pass through the band. In states when the patient is not taking any food, the fluid inside the balloon is soft and does not apply pressure to the stomach wall.

By detecting the flow of food through the region of the restriction device and inducing restriction electrically in these embodiments, the stress on the stomach can be limited to predominantly the "on" time of the restricting device. This arrangement can limit the tendency for erosion exhibited by implantable devices and can also limit the power requirement for electrical stimulation or to change the diameter of the band. In other embodiments, the device end-effector pathways which adjust the restriction elements run in parallel with the sensor but are composed of separate materials. In some embodiments, these devices are further equipped with gain control in which the relationship between the inputs and outputs can be modified. Such gain controls can further be modified externally with a wireless type transmitter.

Figure 21:
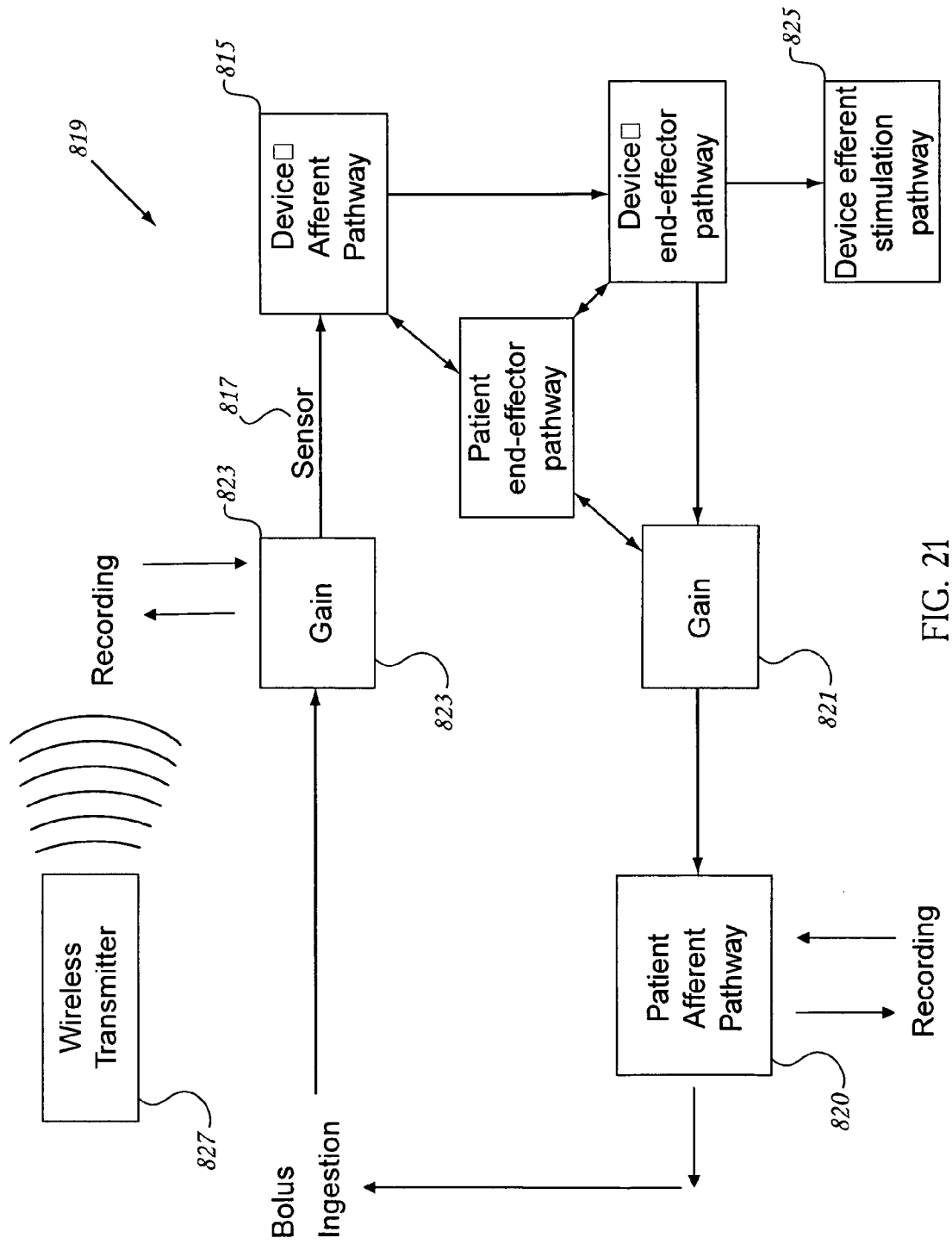
FIG. 21 depicts a schematic of a control system for a gastric restriction device.
Figure 22:
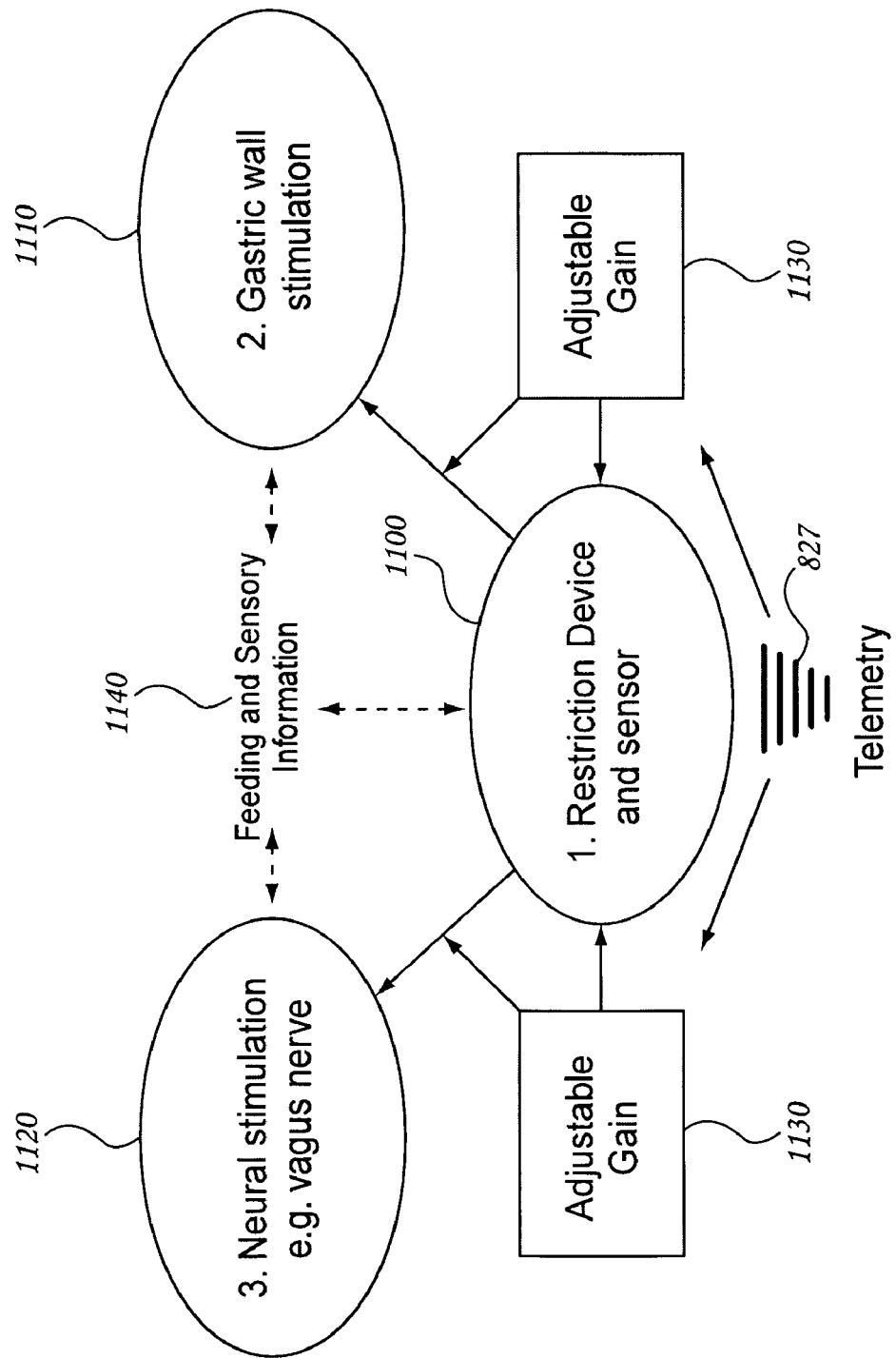
FIG. 22 depicts another schematic of a control system configuration with the surgical procedure as the center of the control system including sensory devices.

Exogenously created satiety pathways can further contain a control system 819 (FIGS. 17B,21,22) which can communicate externally through (for example) wireless transmitters 827 for recording and gain adjustment. The control system 819 can incorporate device afferent pathways 815 (integral sensor 817 such as a strain gauge in one embodiment) such that recording of pressure or volume changes in the distal esophagus, pH in the stomach, relative movement of the afferent sensor, strain or stress on the transgastric connector or circumferential bands, or relative movement of the fasteners of the transgastric fastening assembly, can be fed to the control system 819. Furthermore, the control system 819 has controllable or programmable gains such that the response (e.g. the patient afferent 820, device afferent 815, device efferent 825, device end-effector 831, and patient end-effector 833 pathways) to stimulation is increased or decreased. The gain control can occur with a wireless type 827 transmitting device in some embodiments. Importantly, the schematics of the control system in FIGS. 21,22 are only one depiction of many possible pathway and input-output flow. The various boxes, lines, sensors, and actuators can be mixed and matched in any combination to provide a beneficial effect for a patient. Additional sensors and actuators can be added to the system as well. Some actuators may even be placed outside the abdomen to alert patients or physicians of patient behaviors.

In another embodiment, a sensor (device afferent pathway) 817 is implanted using the methods and devices described herein (e.g. the connector-fastener system and implantation tools described above and below); the sensor 817 can communicate with or be a component of the stimulator and/or the restriction device. In one embodiment, a sensor is placed in the stomach wall (with or without a restricting structure) and senses stretch in the stomach; in another embodiment, the sensor detects transgastric stress and strain or circumferential stress or strain. This sensor can communicate with the stimulator or restricting device to create a feedback loop in which stretch is sensed (the sensor) and then a signal is sent to the stimulator portion of the system (e.g. the device efferent pathway) wherein a nerve (e.g. the patient afferent pathway), for example, the vagus nerve or sympathetic plexus, is stimulated to prompt the patient to slow their intake of food. The end-effecter (patient end-effector pathway) of the feedback loop does not have to be a nervous structure and in some embodiments is a muscular portion of the stomach or duodenum such as the pyloric channel, the antrum, the cardia, or the fundus. In some embodiments, the patient end-effecter pathway is a stimulus such as a small electrical current under the skin to inform the patient that the stomach is full and to stop food intake. In another embodiment, the patient end-effector is an audible alarm. In some embodiments, the device end-effector pathway is an actuator on the gastric band or near to the band and the end-effector can have its power output automatically adjusted. In one embodiment, a transgastric fastening assembly serves to reduce the volume of the stomach as well as provide for electrical stimulation. In this embodiment, an electrical signal runs through electrodes in the transgastric fastener assembly to possibly alter the contraction patterns of the stomach or to electrically create a feeling of satiety in addition to reducing the volume of the stomach and creating a restriction to flow in the stomach. Thus, fastener assemblies of the present invention can serve as electrodes which are useful, for example, for gastric electrical stimulation.

In one embodiment, an exogenous satiety pathway is recreated surgically by implanting a transgastric fastening assembly wherein the connector is adapted to be a strain gauge. In this embodiment, transgastric anchors serve as anchors and/or stimulators and/or sensors in addition to reducing volume or causing mechanical restriction. The fastening assembly is further connected via a device efferent pathway to a patient afferent pathway. Examples of patient afferent pathways include the parasympathetic or sympathetic nervous systems which contain patient afferent fibers which can induce satiety.

In another embodiment, a satiety pathway is recreated surgically by placing a constricting device around a portion of the stomach where the constricting device is able to sense circumferential tension or pressure such as, for example, would be created when food flows through the distal esophagus and proximal stomach. Surgical constricting devices include devices such as the Lap-Band™, transgastric anchor assemblies, or the extragastric restricting devices (e.g. a balloon) discussed below. Any or all of these devices can also be placed around or near an anastomosis such as a Roux-n-Y anastomosis. FIGS. 17B, 18, 21, 22 depict a constricting device 815, 1000 within an obesity treatment system. Sensor 1010 detects a stimulus, the signal is interpreted by the device control system 825, and the signal is delivered to a patient efferent, device end-effector (for example further constriction of a nitinol based band or balloon), device efferent, and/or patient end-effector pathway.

In FIGS. 18*a-c*, a surgically placed banding system 1000 is depicted around the proximal stomach 1005. The band system 1000 comprises a restricting structure 1030 and balloon 1020 which acts to restrict the flow of food into the stomach relative to the pressure in the balloon which initially is dependent on the volume of fluid in the balloon 1010; in this embodiment, the balloon can be fitted with a sensor (e.g. pressure sensor) to provide information about feeding habits including frequency of meals, volume of meals, and consistency (e.g. caloric intake). The pressure sensor 1020 can be incorporated into the fluid fillable balloon 1010 of constricting system 1000. When food passes through the lumen of the restricting device, the pressure increases inside the balloon 1010, signaling patient ingestion. The pressures sensor 1020 can detect changes in balloon pressure as a bolus of food passes through the constricting device system 1000. Although one pressure sensor is used in one preferred embodiment, in alternative embodiments, one or more pressure sensors (1020 in FIG. 18B), strain, or other sensors can be coupled to one another or directly to the balloon.

In one embodiment (FIG. 18D), one or more pressure sensors 1085 are incorporated into the port 1080 of a laparoscopic band. The port communicates directly with the balloon. When fluid is introduced into the port by a surgeon, the pressure in the balloon is measured in order to determine and set the volume of the balloon. In this embodiment, pressure sensors communicate directly with the fluid chamber of the port and therefore communicate directly with the pressure in the balloon. Sensing pressure directly in the port can be advantageous because the balloon and or surgery does not have to be modified to add a pressure sensing to the treatment regime of the patient. Furthermore, in patients whom already have a band in place, the port can be changed without having to worry about the balloon; therefore, a band which is already in place can be outfitted to sense pressure. Further, the port of a balloon already on the market can be retrofitted with pressure sensors, a power supply, and a telemetry without having to develop or change the balloon the patient already has in place. All of these sensing devices can further be adjusted, changed or calibrated when the port is accessed percutaneously.

In one preferred embodiment, a pressure sensor can be incorporated into the bottom portion of the port 1080 by cutting a hole in the port and placing the pressure sensor through the hole so that it is in fluid communication with the fluid inside the port. The sensor can further communicate with a transmitter (e.g. a wireless transmitter) 1090 and power supply. The power supply does not have to be implanted; for example, power can be delivered inductively and remotely to the pressure sensor through the skin. Furthermore, the pressure sensor can communicate with an automated system which fills and/or empties the port based on measurements from the pressure sensor.

In some embodiments, sensor 1020 is not a pressure sensor but a temperature sensor, pH sensor, etc. The pressure sensor is incorporated into system 1060, which in one embodiment is an electronic control system which incorporates the pressure sensor and the output 1050 (e.g. a stimulator). Output 1050 is any of the patient or device efferent or afferent outputs described above and below; in one embodiment, the output pathway is a stomach muscle stimulator 1070 which also stimulates vagal afferents and/or vagal efferent pathways. Required, but not shown is a source of power which, as is well-known in the art, is required for operation of the system and can be delivered remotely or through an integral power supply.

Figure 19:
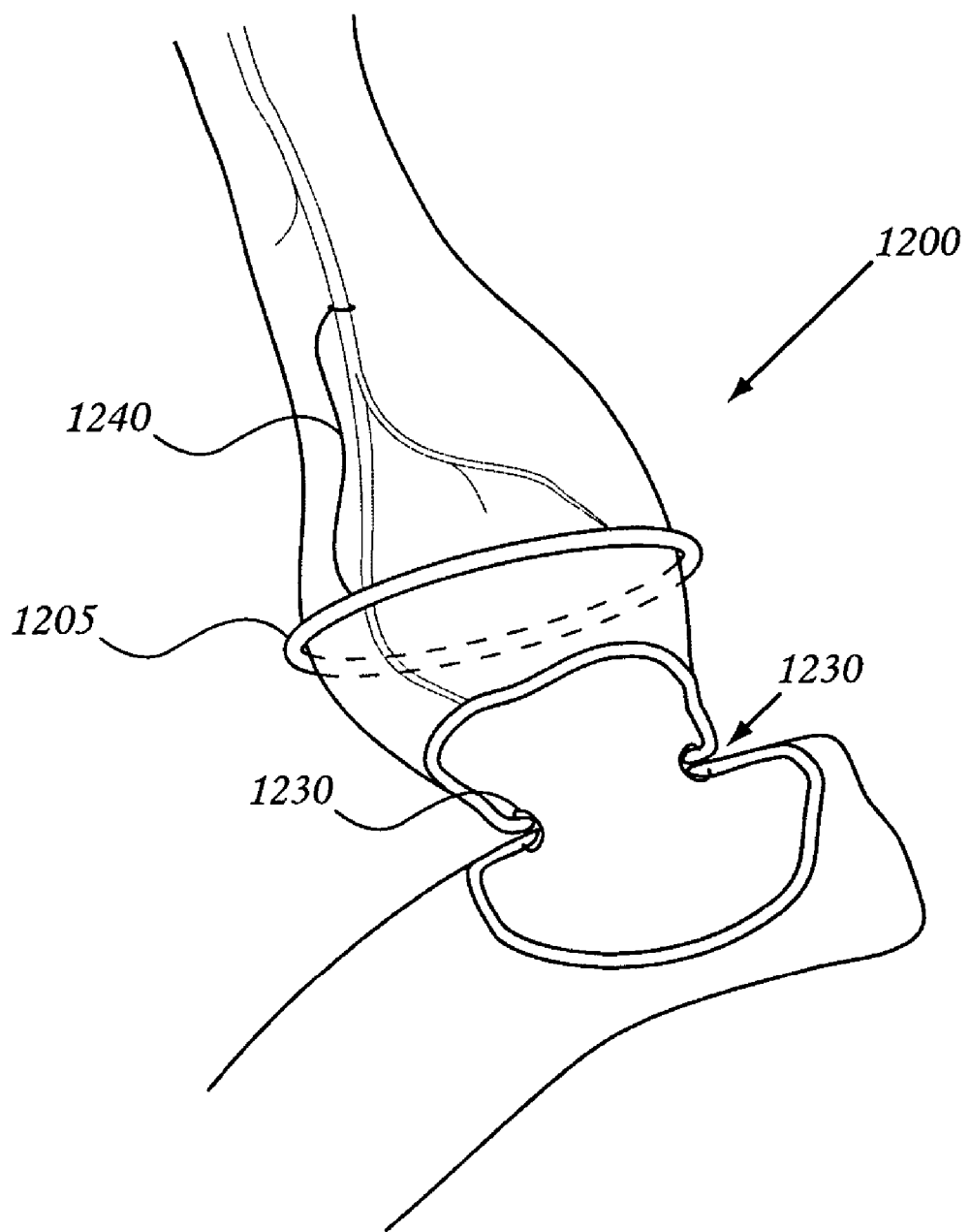
FIG. 19 depicts a surgical anastomosis outfitted with a sensory feedback system.

FIG. 19 depicts a surgically created restriction system 1200 can be placed near or around an anastomosis 1230. In one embodiment, a band 1205 is ultilized as the restriction as well as the structure incorporating a sensor. In another embodiment, surgical clips, sutures, and/or staples 1230 are utlized as sensors for the system 1200. In another embodiment, a port is attached to the constricting band and contains the sensor. In one embodiment, an effector system, such as a vagal nerve stimulator 1240, is incorporated into the surgically created restriction system 1200. As described in other embodiments, there are other system outputs which can be combined with or used in place of the vagal nerve stimulator 1240. Additional components of the other embodiments above and below can be incorporated into the system depicted in FIG. 19. These additional components include telemetry, adjustable gain, power, etc. In addition, although a restricting band 1205 is depicted, other structures such as the transgastric fastening systems or devices similar to the Lap-Band™ can be used in place of the restricting band in this system 1200 at a surgically created anastomosis 1230.

Figure 20:
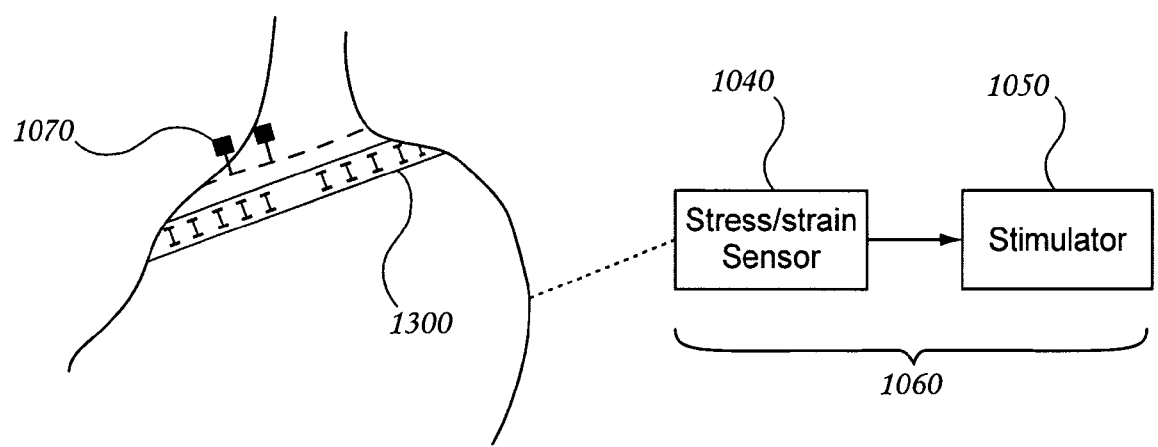
FIG. 20 depicts a preferred embodiment of a gastroplasty device with a central stoma and a feedback system for stimulation.

FIG. 20 depicts a surgically created restriction system placed at the inlet of the stomach. In this embodiment, the restricting portion of the system 1300 is a transgastric assembly as described above. Sensing system 1060 communicates with the transgastric assembly 1300, processing the physical parameter (e.g. stress/strain) associated with the assembly 1300 and delivering an output signal to a device such as an electrical stimulator 1070.

In another embodiment of the current invention, a neurostimulator or neurostimulator lead is a component of the restriction or volume reducing device (but does not have to be an integral component; for example, it can be distal in the stomach yet communicate with the restricting device) and is placed in the serosal layer of the stomach or small intestine to stimulate the muscular or nervous portion of the stomach or small intestine (e.g. the duodenum). In some embodiments, the stimulator contacts and acts on the parasympathetic, the enteric, or the sympathetic nervous system; in other embodiments, the stimulator acts on the muscular portion of the stomach. The stimulator can be placed anywhere along the stomach including the anterior and/or posterior walls of the stomach. In some embodiments, the stimulator contacts the mucosa and in other embodiments, the stimulator does not contact the mucosa. In some embodiments, a sensor is placed as a component of the stimulator or as a separate device. In some embodiments, the stimulator further communicates with a second or third stimulator through a wired or wireless connection.

FIG. 22 further depicts a system for weight control with a surgically created restriction at the center 1100. The system contains one or more output potential pathways such as gastric wall stimulation 1110 and/or visceral stimulation 1120. The system also can contain adjustable gain controls 1130 which control the relationship between the restriction device 1100 and the inputs and outputs. The gains are adjustable from a location external to the patient, or in some cases, are internally adjustable (e.g. through an endoscope). A telemetry system 827 allows for outside monitoring and/or adjustment of the system. A further component of the system is the ability of the system to detect 1140, store, and transmit 827 sensory and motor information from the effector pathways 1110 and 1120. This information includes voltages, amplitudes and waveforms from neural pathways such as the parasympathetic, sympathetic, gastric muscle, and enteric nervous pathways. When interpreted in relation to patient ingestion and type of ingestion, these signals can be used to further understand satiety signals generated in reponse to ingestion. In this manner, the system can essentially learn from itself and be optimized for each patient.

Extragastric Restriction Devices

Figure 11C:
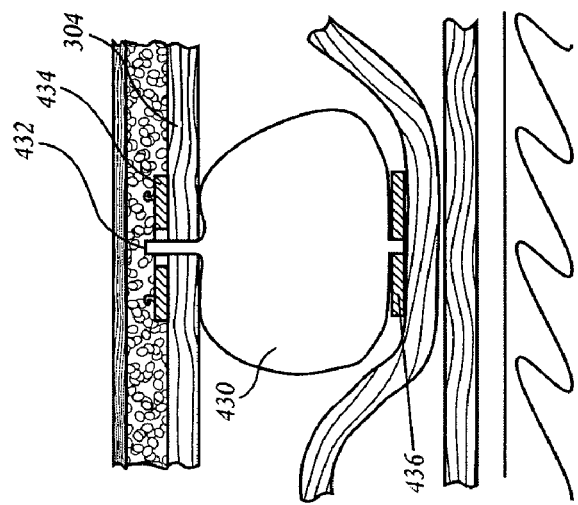
FIG. 11C illustrates a volume displacing device which resides outside the stomach and is fixed to the anterior wall of the stomach and to the abdominal wall with an anterior anchor and connector.
Figure 11B:
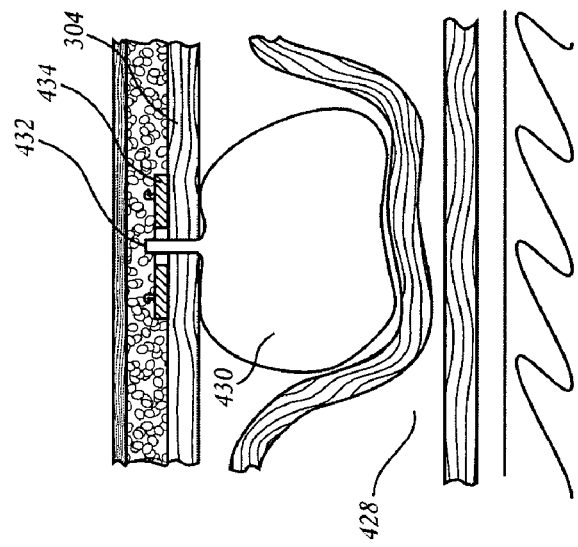
FIG. 11B illustrates a volume displacing device which resides outside that stomach and is shown in a deployed state and adapted to the contour of the stomach.
Figure 11A:
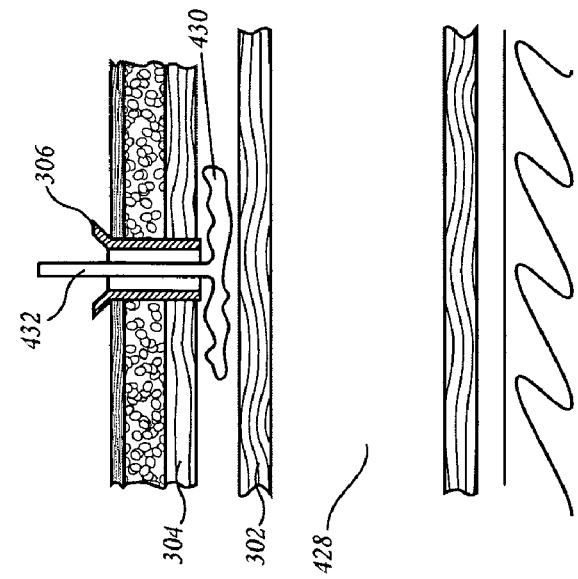
FIG. 11A illustrates a volume displacing device which resides outside the stomach and is shown in an undeployed state.

In another embodiment, an extragastric balloon (FIGS. 11A-11C) is used to reduce the volume of the stomach and/or create a barrier to the flow of food and a restrictor to the flow of food. FIG. 11a depicts the balloon 430 in the undeployed configuration. The balloon is placed through a trocar port 306 after the trocar port has been placed between the peritoneum and the anterior wall of the stomach as described in detail above and below. FIG. 11B shows an embodiment of an extragastric balloon 430 in its deployed state. The balloon 430 is attached to the abdominal wall by any of the percutaneous anchor-connector assemblies and methods described above. Stem 432 is the residual from the connector used to place the balloon with an optional access port/valve for further inflation and/or deflation after the balloon is placed. Anchor 434 is similar to the anterior anchors described above can be placed between the muscular portion of the abdominal wall 304 and the subcutaneous fat or between the anterior layer of muscular fascia and the muscle (e.g. the rectus muscle). In some embodiments, the balloon is placed close to the pylorus or at the fundus of the stomach close to the GE junction and can optionally be contoured 433 to partially of completely surround the GE junction or the pyloric outlet. In some embodiments (FIG. 11c), the posterior portion of the balloon is fixed 436 to the outer or inner portion of the stomach using any of the fastening systems described above. The balloon can further be combined with a transgastric anchor assembly to aid its attachment, to control tension on the transgastric assembly, or to synergize with the transgastric anchor assembly. The posterior portion of the balloon can be fixed to the anterior gastric wall with an anchor delivered through the stomach with an endoscope.

The extragastric balloon can be placed anywhere along the stomach, even at a position 1-5 cm below the gastroesophageal junction at the same place where laparoscopically placed adjustable gastric bands are currently placed. The balloon can further be shaped to partially circumscribe, or form a lumen (fully circumscribe) around, a structure such as the gastroesophageal junction. Even though the balloon may completely circumscribe the stomach, it does not necessarily have to be a continuous ring and can be discontinuous even though it forms a complete ring when fully expanded. In some embodiments, multiple balloons are implanted. The extragastric balloons can further be configured to act as stimulators and can deliver electrical current or sense certain parameters such as peristaltic contraction or food boluses. This information can be used to increase or decrease the volume of the balloon accordingly.

As described above, any of the extragastric balloon embodiments can further contain an integral sensor to detect changes in volume (for example, volume and/or pressure changes) of the restricted portion of the stomach. Such changes in volume can then be used to create satiety feedback loops to deter the patient from further food intake (as discussed above and below, for example, vagal nerve stimulation).

In some embodiments, mechanical fixation structures are used to attach the balloon to the serosa of the stomach. Other means of attaching balloons to the stomach include adhesives, pledgets, expandable anchors, etc. The connector-anchor systems above are used to attach the balloon to the abdominal wall. The connector can further serve as an inflation valve for the extragastric balloon.

Surgical Instruments

Surgical instruments which can be used to implant many of the devices of this invention are disclosed. The surgical instruments represent one example of the methods to implant the disclosed device but not the only possible means for implantation. Any of the devices and/or methods and/or features of the current inventions can be implanted with an endoscopic procedure in addition to endoscopic means to assist a percutaneous procedure or an endoscopic means to assist a laparoscopic procedure.

Figure 4A:
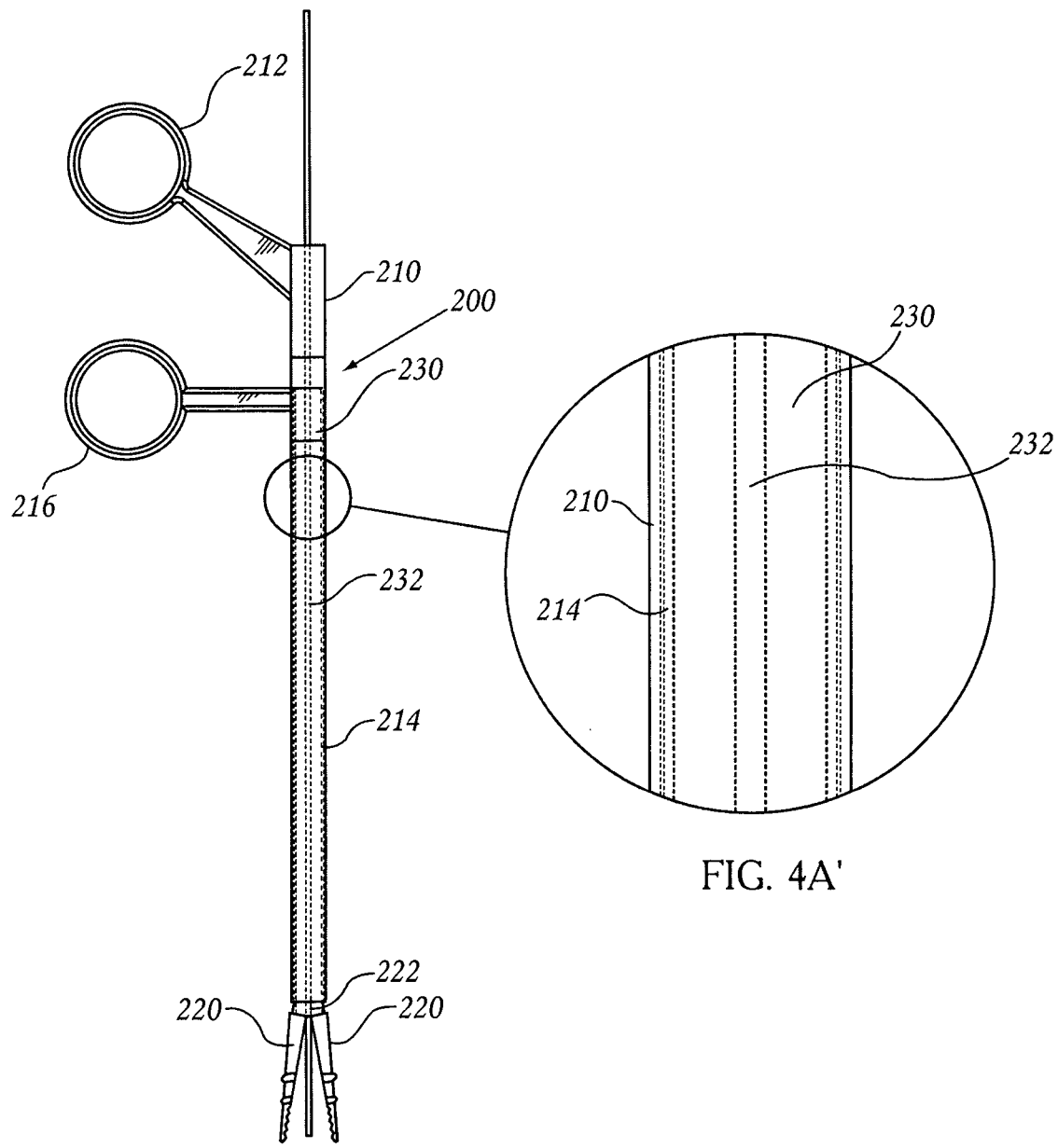
FIGS. 4A and 4A' are a side and blow-up view, respectively, of one embodiment of a tissue grasping instrument with the distal end in its open configuration.
Figure 4B:
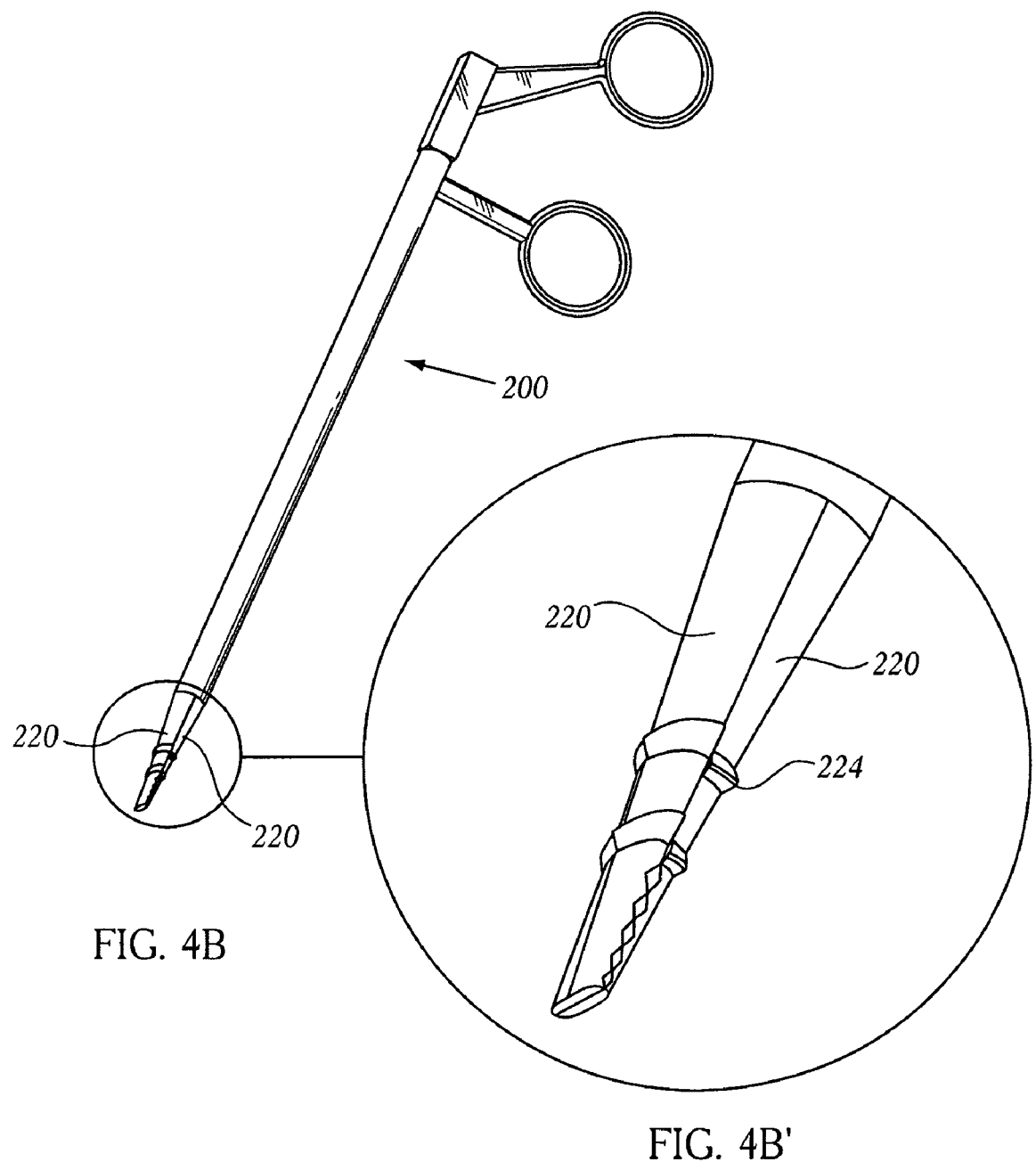
FIGS. 4B and 4B' are a perspective and blow-up view, respectively, of the tissue grasping instrument of FIG. 4A with the distal end in its closed configuration.

FIG. 4A illustrates one embodiment of a tissue grasping instrument 200. The tissue grasper has a tubular outer sleeve 210 to which a portion of a handle 212 is attached at the proximal end. As shown in more detail in the blow-up, FIG. 4A', disposed within the outer sleeve 210 is a tubular inner member 214 which has an outer diameter such that it can slide within the outer sleeve 210 in the longitudinal axis of the outer sleeve 210 but cannot move substantially transverse to the longitudinal axis of the outer sleeve 210. At the proximal end of the inner member, a second portion of a handle 216 is attached. At the distal end of the inner member is a pair of jaws 220 which is connected to the inner member at a hinge point 222. When the distal end of the inner member 214 is displaced from the inside of the outer sleeve 210 such that the hinge point 222 is outside the outer sleeve, the jaws 220 assume their open position as depicted in FIG. 4A. As the hinge point 222 is withdrawn into the outer sleeve 210, the outer sleeve forces the jaws 220 into their closed position, as illustrated in FIG. 4B. The opening and closing of the jaws 220 can be accomplished by manipulation of the handle portions 212 and 216.

Figure 4C:
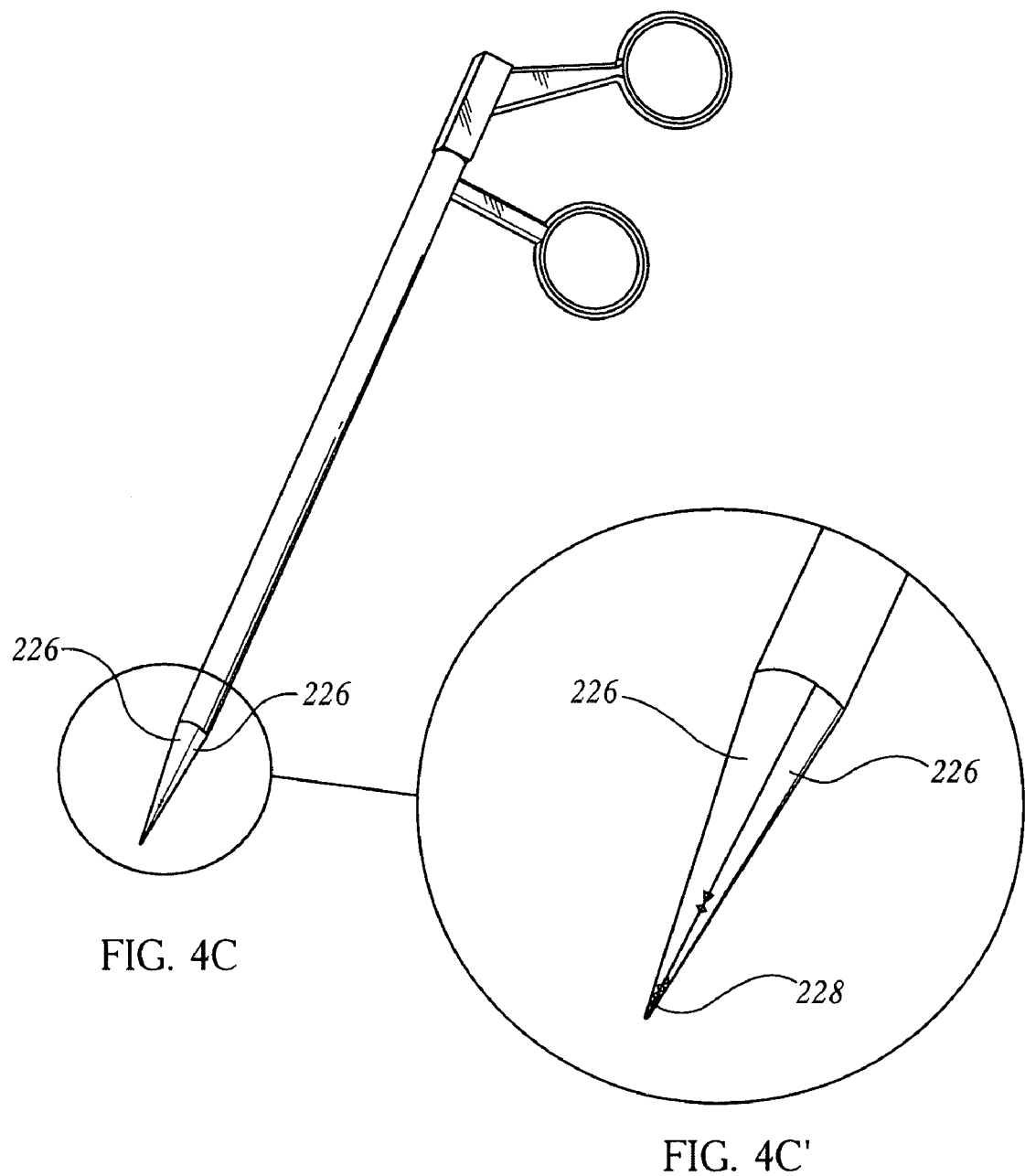
FIGS. 4C and 4C' are a perspective and blow-up view, respectively, of another embodiment of the tissue grasping instrument with the distal end in its closed configuration.

The distal end of the grasping instrument 200 is configured to cut, puncture, or dilate tissue when the jaws 220 are in the closed position. In one embodiment shown in FIG. 4B, the jaws 220 have screw-thread-shaped protrusions 224 on the surface. By rotating the instrument as it passes through tissue, the protrusions 224 facilitate the penetration of tissue, similar to a corkscrew. In another embodiment illustrated in FIG. 4C, the instrument has jaws 226 that form a sharp tip 228 when closed. In yet another embodiment, the jaws form a blade which can cut through tissues when in the closed position. One of skill in the art would recognize that the above configurations can be combined, or that other configurations are possible which facilitate the passage of the tip of the instrument through the wall of the stomach or other tissue.

It also should be realized to one skilled in the art that the closed end of the grasping device does not have to be the only instrument responsible for cutting through the tissue; the central lumen 230 of the device can be utilized to assist in tissue penetration. For example, a needle (e.g. a Veres needle) 232 can be passed through the lumen and the needle 232 can make the initial puncture through the tissue. The configuration of the distal end of the grasper is meant to be a tissue dilator and facilitator of the entry into the stomach (or any other hollow organ) after the needle makes the initial puncture. For safety, the needle can be retracted as the tissue grasper dilates the tissue.

In the embodiment of the tissue grasper 200 illustrated in FIG. 4A, the inner member 214 and outer sleeve 210 have a central tunnel 230 that extends the length of the tissue grasper. The tunnel 230 allows for the passage of an expanding means such as a needle 232, or other instrument or device such as the posterior or anterior anchor described above (see for example, the description above regarding the connector-suture combination in which the suture is left behind and the outer sheath of the connector is pulled away), through the length of the tissue grasper as shown in FIG. 4A. The central tunnel is also adapted such that a radially dilating sheath can be inserted through it. The diameter of the central lumen is preferably at least 4 mm, but can be at least 5, 6, 7, 8, 9, 10, 11, or 12 mm. In an alternative embodiment, the distal jaws can be configured to close through an electromechanical means or purely magnetic means such that the inner member is not necessary.

Figure 5A:
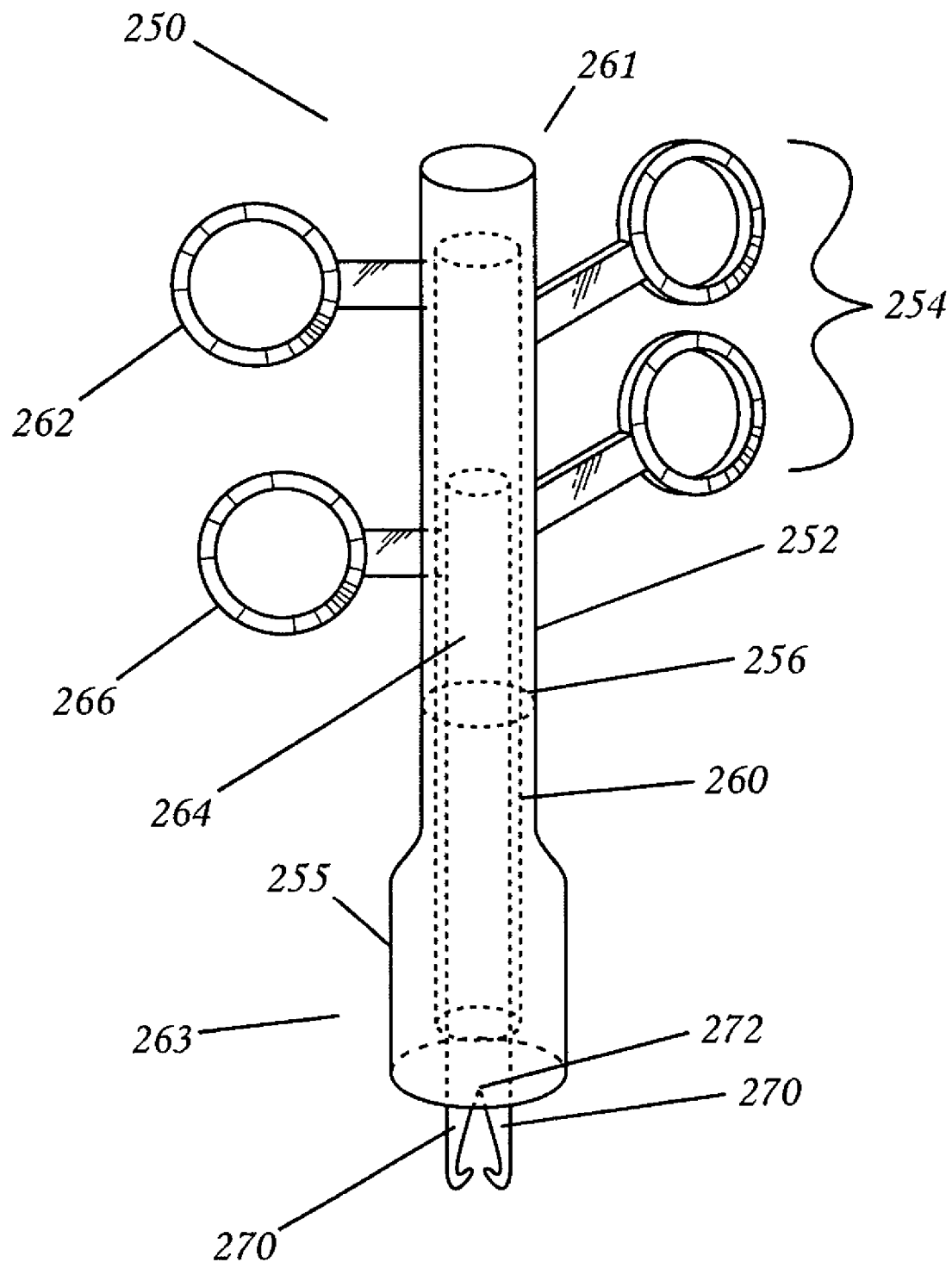
FIG. 5A is a side view of one embodiment of an anchor implantation instrument.

FIG. 5A illustrates one embodiment of an anchor implantation instrument 250 to implant the anterior anchor. The implantation instrument has a tubular outer sheath 252 which has a handle 254 attached. At the distal end, the outer sheath flairs out to an increased diameter 255 to accommodate the anterior anchor in its substantially folded position as illustrated in FIG. 5C. Within the outer sheath is an anchor grasping instrument 256 similar to the tissue grasping instrument of FIG. 4A, made up of a tubular middle sleeve 260 and a tubular inner member 264. The tubular middle sleeve 260 has an outer diameter such that it can slide within the outer sheath 252 in the longitudinal axis of the outer sheath 252 but cannot move substantially transverse to the longitudinal axis of the outer sheath 252.

The tubular middle sleeve 260 of the anchor grasping instrument has a portion of a handle 262 attached at the proximal end 261 of the instrument. Disposed within the middle sleeve 260 is a tubular inner member 264 which has an outer diameter such that it can slide within the middle sleeve 260 in the direction of the longitudinal axis of the middle sleeve 260 but cannot move substantially in transverse to the longitudinal axis of the middle sleeve 260. At the proximal end of the inner member, a second portion of a handle 266 is attached.

Figure 5B:
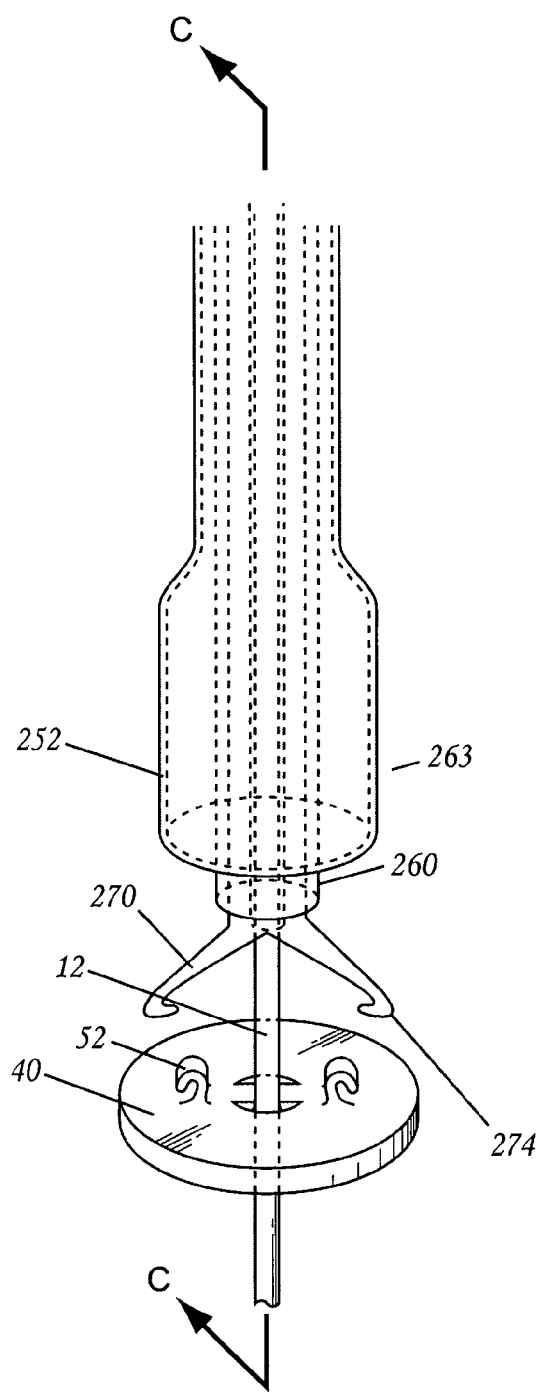
FIG. 5B is a perspective view of the distal end of the anchor implantation instrument of FIG. 5A and an anterior anchor and connector.
Figure 5C:
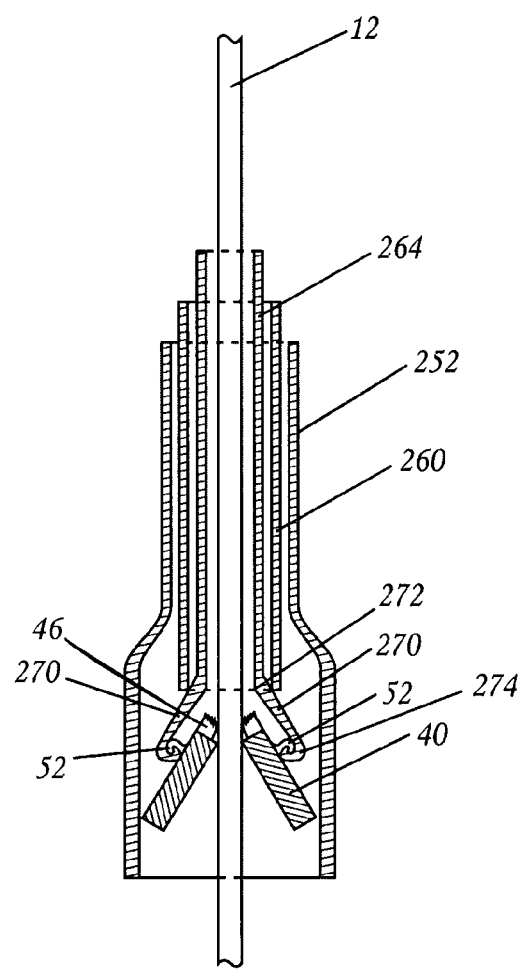
FIG. 5C is a side sectional view of the distal end of the anchor implantation instrument of FIGS. 5A and 5B, taken along line C-C in FIG. 5B, with the anterior anchor in its reduced profile configuration.

The distal tip 263 of the instrument is illustrated in more detail in FIGS. 5B and 5C, with the inclusion of the anterior anchor 40 of FIG. 2A and connector 12 of FIG. 1A. FIG. 5C is a side section view taken along the line C-C of FIG. 5B. At the distal end 263 of the inner member 264 is a pair of hooking members 270 which are connected to the inner member at a hinge point 272. When the distal end of the inner member 264 is displaced from the inside of the middle sleeve 260 such that the hinge point 272 is outside the middle sleeve, the hooking members 270 assume their open position as depicted in FIG. 5B. As the hinge point 272 is withdrawn into the middle sleeve 260, the middle sleeve forces the hooking members 270 into a closed position, as illustrated in FIG. 5C. The opening and closing of the hooking members 270 can be accomplished by manipulation of the handle portions 262 and 266.

The instrument is designed such that the anterior anchor is easily manipulated. When the anterior anchor is in its substantially folded or compressed configuration as in FIG. 5C, the entire anterior anchor assembly can be manipulated along the longitudinal axis of the connector 12. FIG. 5C depicts the assembly as it would be introduced over the connector 12 and into the patient. The operator pulls the connector 12 toward the operator such that the posterior anchor is urged toward the anterior anchor. When in position, the operator deploys anterior anchor 40. To deploy anterior anchor 40, outer sheath 252 is pulled back toward the operator. Middle sleeve 260 is then withdrawn proximally toward the operator as well. Hooking members 270 tend to fan out as the middle sleeve is pulled back and will release hooks 52. Once deployed, anterior anchor 40 is now fixed in a longitudinal position along the connector 12.

An important feature of the anterior anchor in some embodiments is that it be grippable by a laparoscopic grasping instrument and able to be translated through a laparoscopic port; further, the anterior anchor is reversibly translatable along the connector such that the surgeon can place and replace depending on what is seen by the endoscopist or the tension indicated by the tensiometers. If the surgeon wants to readjust the anterior anchor, connector 12 is manipulated so that the hooks 52 of the anterior anchor are brought into contact with hooking members 270; middle sleeve 260 is advanced distally from the operator, permitting hooking members 270 to engage the hooks 52; such contact is facilitated by pulling back (proximally) on the connector 12. By manipulating the middle sleeve 260 over the hooking members 270, the hooks 274 on the ends of the hooking members 270 can engage the hooks 52 on the anterior anchor 40. The outer sheath 252 is then slid over the anterior anchor 40 (or the anchor-middle sleeve complex is withdrawn into the outer sheath 252), until it is compressed into an undeployed configuration as shown in FIG. 5C. As described above, when the anterior anchor 40 is in a substantially compressed configuration, it can move along the length of the connector 12 in either direction.

In an embodiment where an inflatable anterior anchor such as the one illustrated in FIGS. 2G-2I is utilized (or in the case that the anterior anchor is otherwise sufficiently compliant to be pushed through a laparoscopic port), a standard laparoscopic grasping instrument (with teeth) can be used to manipulate the anterior anchor. When the inflatable anterior anchor is in the uninflated position, it is sufficiently compliant such that it can easily be passed through a laparoscopic port prior to inflation and deployment or after it has been deflated for readjustment; the middle sheath may not be necessary because the compliance of the balloon enables easy compression into the outer sheath. The inflation tube 63 passes through the laparoscopic port and out of the patient. This allows the inflation tube 63 of the anchor to be temporarily opened or closed outside the patient allowing for deflation and reinflation until the anchor is in place. The inflation tube is then sealed and cut off, preferably substantially flush to the surface of the anterior anchor.

Methods of Implantation

Percutaneous Procedure

FIG. 6A depicts the initial step of a preferred embodiment of a surgical method to implant a transgastric fastening assembly. The first part of one procedure embodiment, the "percutaneous procedure," involves entering the stomach with an endoscope 300 and insufflating the stomach with a gas. When insufflated, the anterior wall of the stomach 302 is pushed toward the anterior abdominal wall 304 to create a potential space (the stomach interior). After insufflation of the stomach, an incision is made in the skin and a typical laparoscopic port 306 is placed through the anterior abdominal wall 304 to a position wherein the distal end is in the potential space between the abdominal wall 304 and the anterior wall of stomach 302. The laparoscopic port 306 can be a radially dilating type port or similar port known in the art. Even though a laparoscopic port is used, in these steps, generalized pneumoperitoneum is not required and this part of the procedure can be done with minimal or no general anesthesia as discussed in the next paragraph.

A particularly advantageous laparoscopic port is one which allows visualization (with a laparoscope) of the individual abdominal layers as the laparoscope is being pushed through the abdominal wall (well known to those skilled in the art). Use of such a port allows the surgeon to "see" the different layers of the abdominal wall from within the trocar (using a standard laparoscopic camera) as the trocar is advanced through the abdominal wall. The endoscopic light inside the stomach will be "seen" by the surgeon as the port approaches the inner layers of the abdominal wall because the endoscopic light source transilluminates through the layers of the stomach wall and inner layers of the abdominal wall. Such visualization is advantageous if the patient has a very thick abdominal wall (e.g. in a morbidly obese patient) because the surgeon needs to ensure that another organ (e.g. the colon) is not positioned between the stomach and the posterior wall of the abdomen. Once the transillumination of the stomach is visible through the transparent port, the port 306 can be slipped in the abdomen between the abdominal wall and the anterior wall of the stomach. This portion of the procedure may be done without pneumoperitoneum and without general anesthesia (e.g. local anesthesia).

At this point, the camera can also be used to visualize the anterior wall of the stomach and/or it can be used to visualize placement of devices into the anterior wall of the stomach; examples of some devices include stimulators, sutures, clips, drug delivery devices, sensors, and volume displacing devices (extragastric balloons are discussed below). As described above, visualization of the surface of the stomach and implantation of devices into the anterior wall (without puncturing through the stomach) can be achieved with this method and does not require general pneumoperitoneum. The camera can be slid along the stomach to reach virtually any portion of the anterior stomach, duodenal wall, or lower esophagus. Additional ports can also be placed in the space between the abdominal wall and the anterior wall of the stomach. With the additional ports, additional instruments can be used which can facilitate placement of the devices into the walls of the stomach. Suture passers, knot tiers, electrosurgical devices, and clip appliers are just some examples of instruments which already exist in the surgical arts and which can be utilized to facilitate placement of devices into the walls of the stomach. Small incisions can be made in the serosa of the stomach and a pocket can be made so that stimulators can be placed in a pouch in the stomach wall. Therefore, using the inventive technique of entering the abdomen without general anesthesia and without pneumoperitoneum as detailed above, many different gastric operations can be performed.

At this point in the procedure (or any other point), a therapeutic energy device can also be applied to the stomach. For example, a laser (or other phototherapy device), a radiofrequency device, a microwave device, or an ultrasound device can be applied to the stomach. Furthermore, electrical or nervous mapping can be performed with the surgical device in the position between the anterior wall of the stomach and the abdominal wall. In the embodiment where an extragastric balloon is being deployed (see above and below), such deployment can proceed at this step. The ability to perform these procedures without general pneumoperitoneum and with minimal anesthesia is enabled by the inventive methods described above. Furthermore, in the embodiment where balloons are placed inside the stomach or neuro- or muscular stimulators or other devices are placed in the walls of the stomach, these devices are implanted at this step and do not require pneumoperitoneum or general anesthesia.

At this point in the percutaneous procedure (after entry into the stomach), the tissue grasping instrument 200 of FIG. 4A is inserted through the port 306 with the jaws 220 in the closed position (with or without a needle projecting in front of the instrument) and is passed through the anterior wall of the stomach 302. When the jaws of the instrument are closed, the jaws define a sharp, dilating, and/or cutting configuration which can more easily advance through the stomach wall.

FIG. 6B depicts the next step in the percutaneous procedure. The jaws of instrument 200 are used to grasp the posterior wall of the stomach. Although one method to approach the region behind the stomach is shown in the FIG. 6b, there are many ways in which the posterior wall of the stomach can be accessed. For example, suction can be used, as can visualization with an ultrasound probe, CT scan, MRI, and/or fluoroscopy. The posterior wall of the stomach 314 is lifted away from the retroperitoneum 316, allowing for access to the potential space of the lesser peritoneal sac 320. A needle 232, such as a Veres needle (well-known in the art, a Veres needle allows for easy and safe access into and between two serosal layers), is inserted through the central channel 230 of the instrument and passed through the posterior wall of the stomach 314 into the potential space of the lesser peritoneal sac 320. The potential space of the lesser peritoneal sac 320 is expanded by injection of a gas, such as carbon dioxide, through the needle 232. In other embodiments, the potential space is expanded using a liquid, gel, or foam. Alternatively, the space can be expanded using a balloon or other space expanding or space filling device; alternatively, a surgical instrument (e.g. electrocautery and/or blunt ended grasper, etc.) can be used in place of a needle to access the lesser peritoneum or to expand the potential space of the retroperitoneum 320. Preferably, the expanded space of the lesser peritoneal sac can extend from the angle of His at the gastroesophageal junction to the pylorus.

Figure 6D:
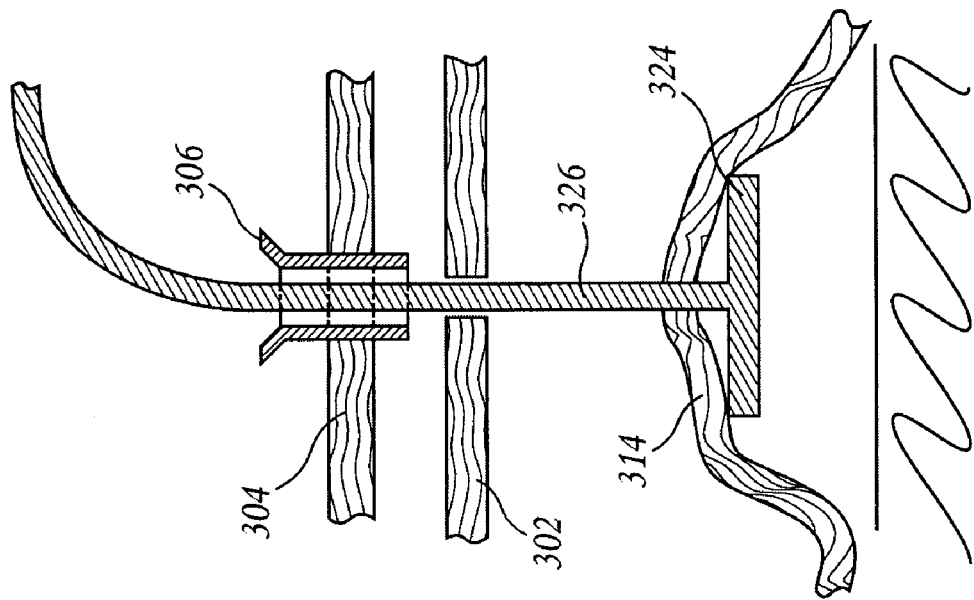
FIG. 6D illustrates the next step in one embodiment of a method of reducing the volume of the stomach. Shown is a side sectional view of a patient's abdomen with a posterior anchor and connector deployed in the expanded potential space of the lesser peritoneal sac, with the connector passing out of the patient's abdomen through a laparoscopic port.
Figure 6C:
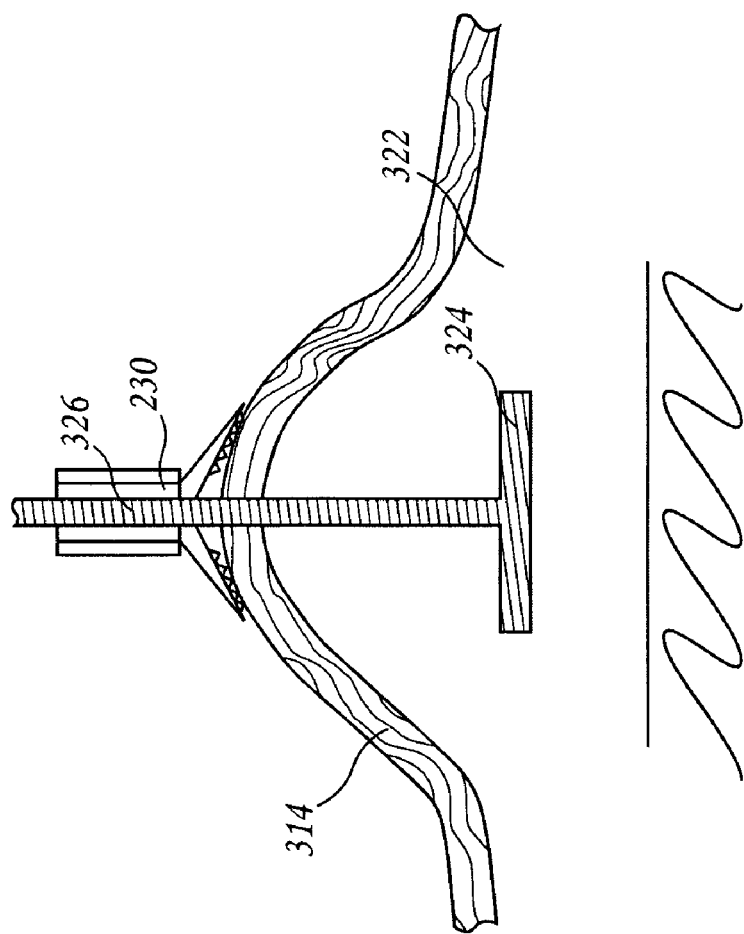
FIG. 6C illustrates the next step in one embodiment of a method of reducing the volume of the stomach. Shown is a side sectional view of a patient's abdomen with the instrument of FIG. 4 grasping the posterior wall of the stomach and a posterior anchor and connector deployed in the expanded potential space of the lesser peritoneal sac.

FIG. 6C depicts the next step in the "percutaneous procedure" embodiment. With a direct path from outside the patient to the lesser peritoneal sac 322, the needle 232 is withdrawn from the instrument 200. An optional dilation step can be performed at this stage in the procedure using a device such as a radially dilating sheath (e.g. InnerDyne STEP™ system; Sunnyvale, Calif.) inserted through the central channel 230 of the instrument. The dilating device expands the opening in the posterior wall of the stomach in such a way that the opening contracts down to a lesser profile after dilation. A posterior anchor 324 and connector 326, such as those depicted in FIGS. 1B, 1E or preferably 1F, in its reduced profile configuration, is passed through the central channel 230 of the instrument, through the posterior wall of the stomach 314, and deployed in the lesser peritoneal sac 322 as shown in FIG. 6C. Where the optional dilation step is performed, the posterior anchor 324 is passed through the dilating sheath. The connector 326 is preferably of sufficient length to pass from inside the lesser peritoneal sac 322 through the central channel 230 of the instrument and out of the patient's body. FIG. 6D depicts the deployed posterior anchor 324 and connector 326 after the grasping instrument is withdrawn from the patient and tension is applied to connector 326 to pull the posterior anchor 324 against the posterior wall of the stomach 314.

In an alternative embodiment, the space of the lesser peritoneal sac is not expanded before the posterior anchor is placed. For example, in an embodiment where an inflatable posterior anchor is used, the potential space can be expanded by the anchor itself as it is inflated to its deployed configuration.

In another embodiment, the posterior anchor is directly implanted in the retroperitoneum rather than in the lesser peritoneal sac. In this embodiment, the posterior anchor is placed in the retroperitoneum above the envelope of the lesser peritoneal sac. Above the envelope, the retroperitoneum is safe, being above the pancreas and splenic vessels. As is known to those skilled in the art of bariatric surgery, the Lap-Band® is implanted at this spot in the retroperitoneum (however, implantation requires general anesthesia and pneumoperitoneum). A Cat-Scan, MRI, fluoroscopy, or ultrasound can be used to assist in this step.

Laparoscopic Procedure

Figure 6E:
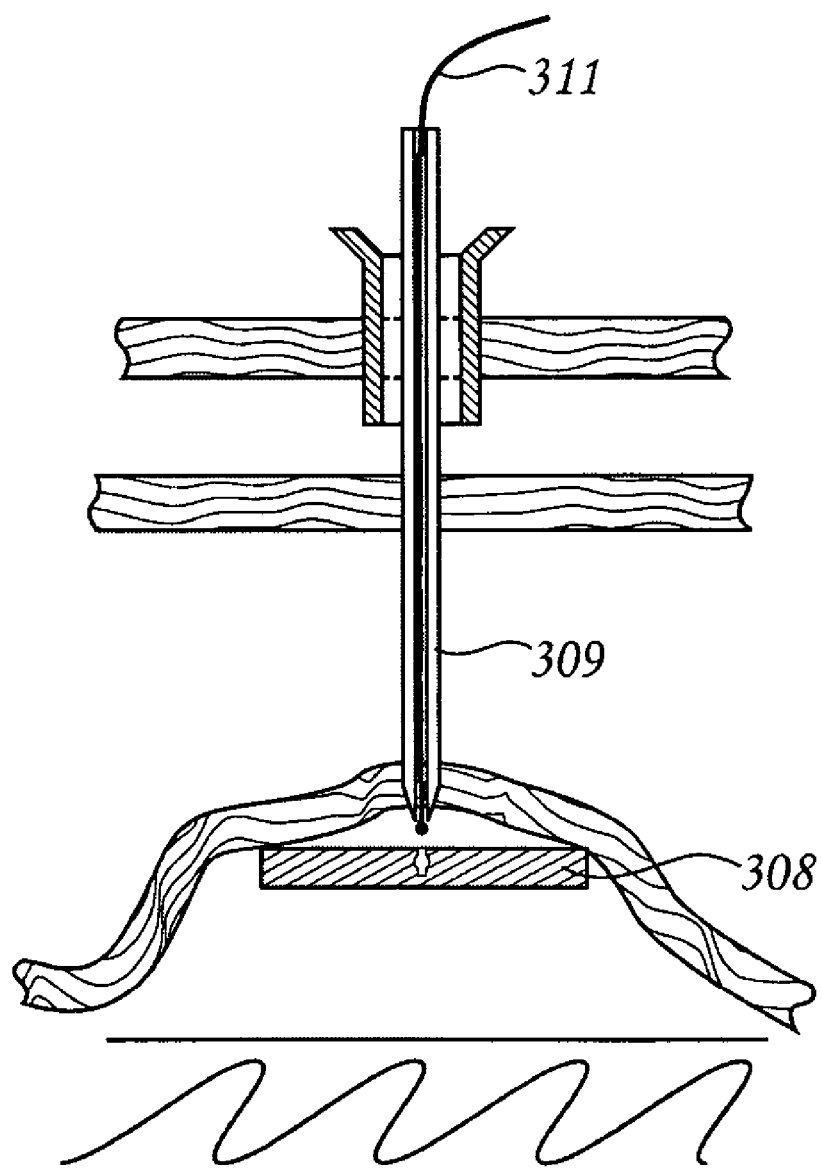
FIG. 6E illustrates an alternative step and device to place the posterior anchor in which the posterior anchor is brought behind the stomach before the connector is attached.
Figure 15A:
FIGS. 15a-b illustrate the placement of a continuous posterior anchor in the laparoscopic procedure.
Figure 15B:
Figure 15C:
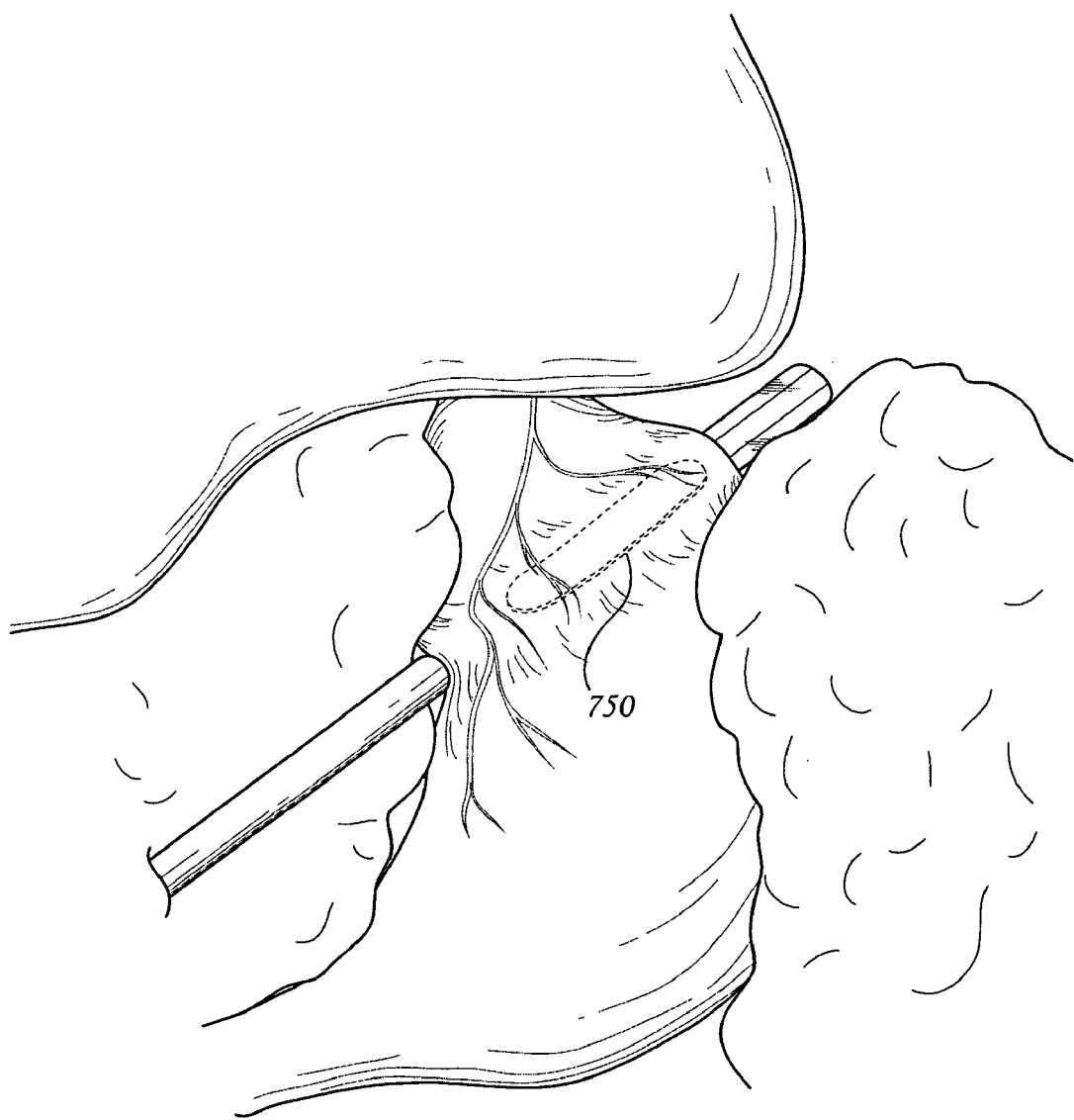
FIGS. 15c-d depicts a horizontal row of transgastric anchors and connectors after their placement in the stomach.
Figure 15D:
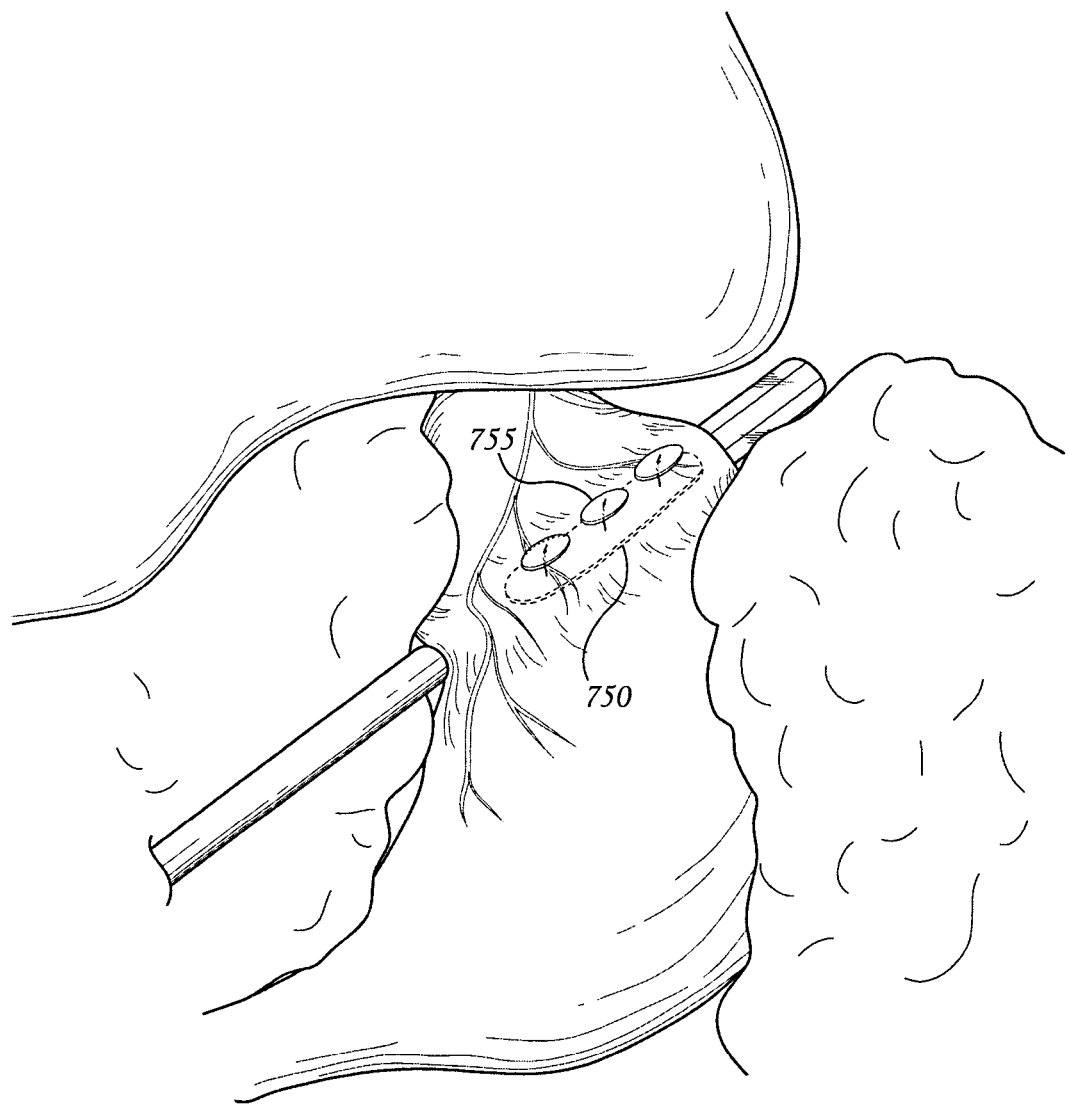

In the "laparoscopic procedure," after insufflation (pneumoperitoneum and general anesthesia) of the abdominal cavity with a Veres needle, a retrogastric tunnel 500 is created as is well known in the surgical arts and is shown in FIG. 15a. The posterior anchors 510 are shown as a component of the retrogastric instrument 510 in FIGS. 12 and 15a. Embodiments of the posterior anchors 308 are also shown in FIGS. 6E and 1K. Depicted are single posterior anchors with one or more connectors and continuous posterior anchors with one or more connectors. The suture-connector system 309, 311 depicted in FIG. 1 H-J is also depicted in FIG. 6E and can be used in one of the laparoscopic embodiments. Connector 309 (in FIG. 6E) engages anchor 308 and locks suture 311 into posterior anchor 308. Connector 309 is then slid over suture 311 prior to the anterior anchor (similar to the anterior anchor in FIG. 13a; 550) being slid over (tracking) the connector 311. FIG. 15B depicts the configuration of the transgastric anchor assemblies 700 after the anterior anchors are placed, tensioned, and the connectors are cut. FIG. 15C depicts devices of the laparoscopic procedure where the posterior anchor 750 is continuous. Anterior anchors 755 are shown as individual anchors and as discs; however, in some embodiments, the anterior anchors can be rectangular or continuous.

Figure 12A:
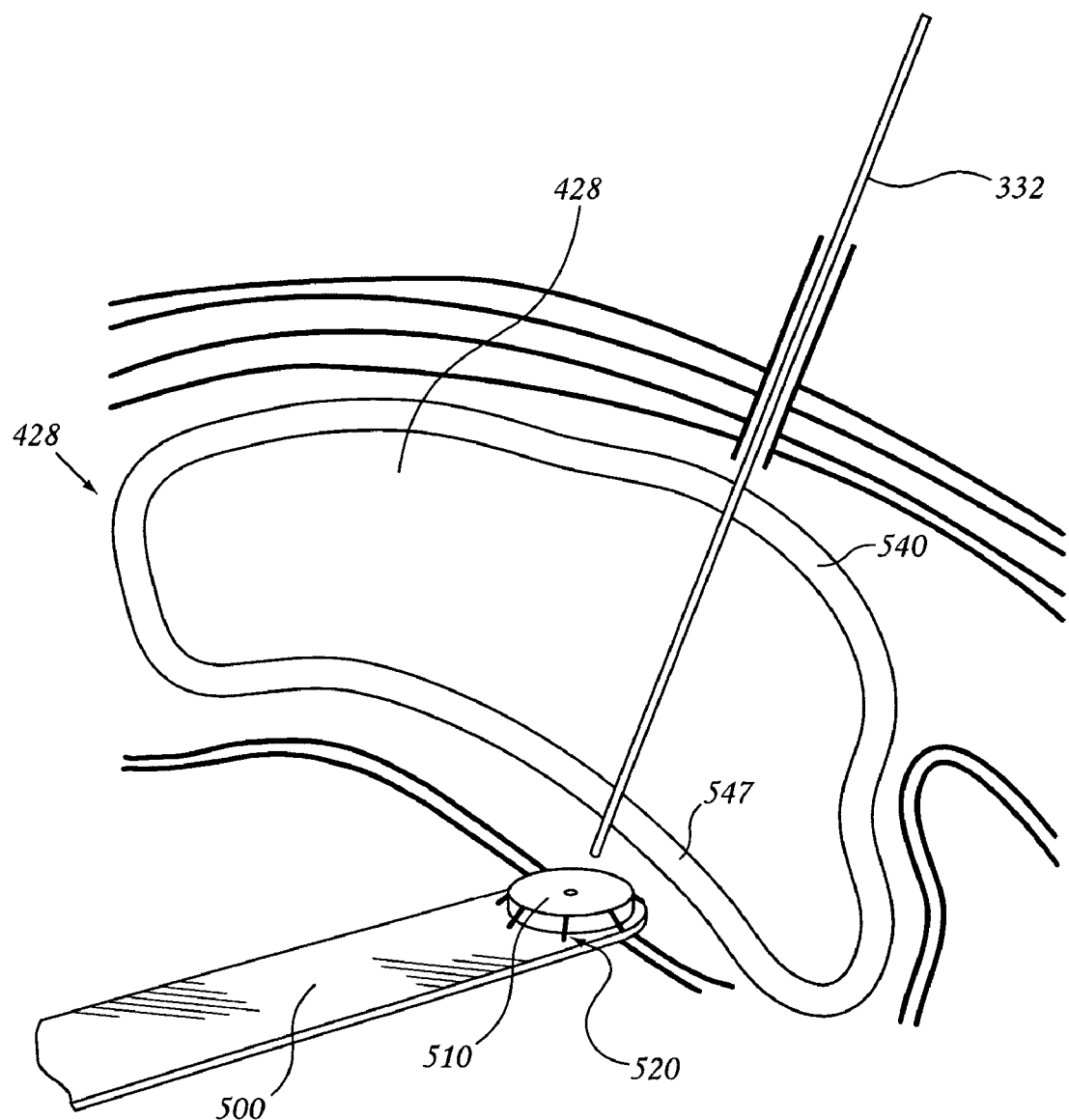
FIGS. 12a-c illustrate the steps in the laparoscopic method of placing a device in the stomach where the transgastric connector attaches a suture to a posterior anchor.
Figure 12B:
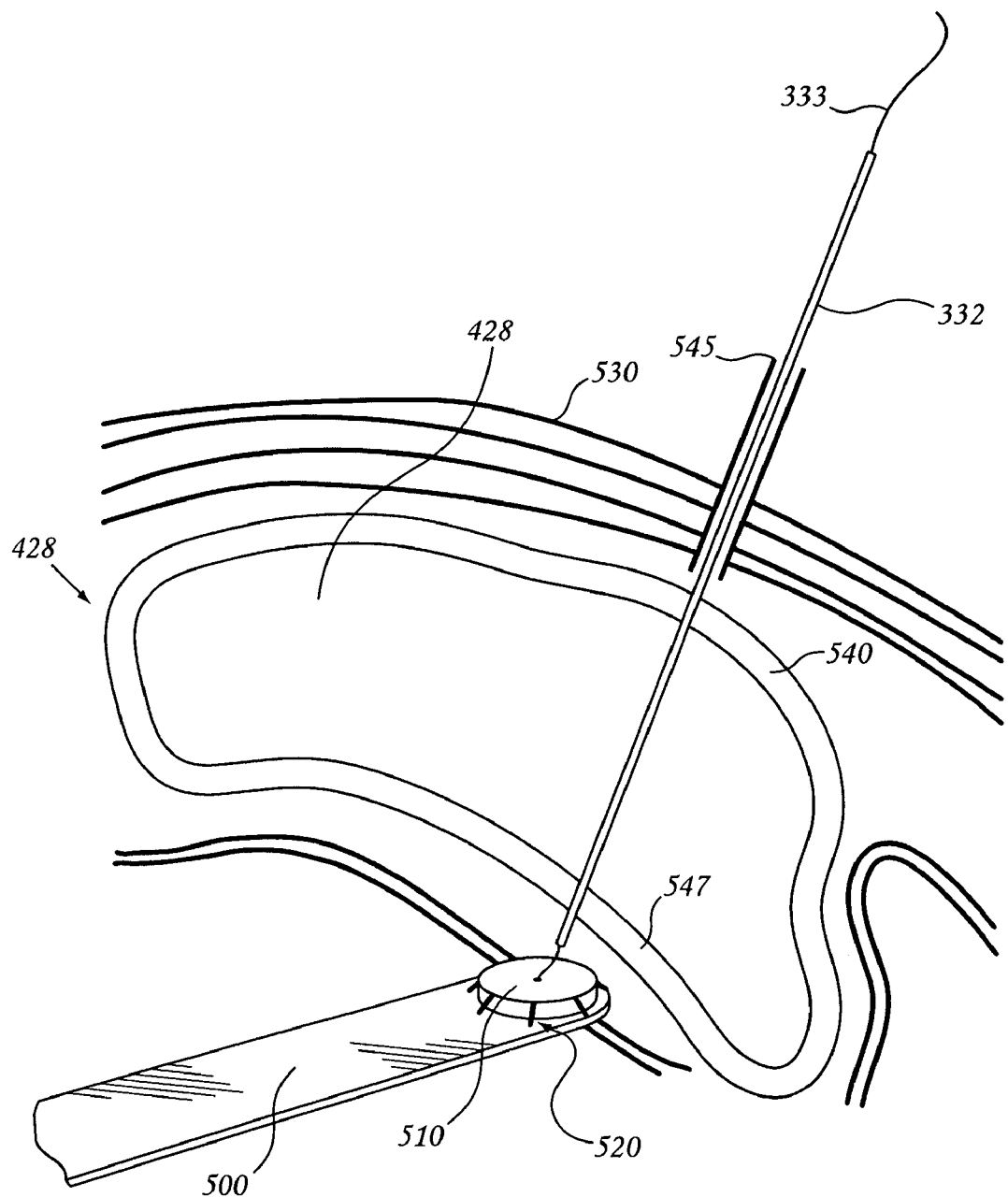
Figure 12C:
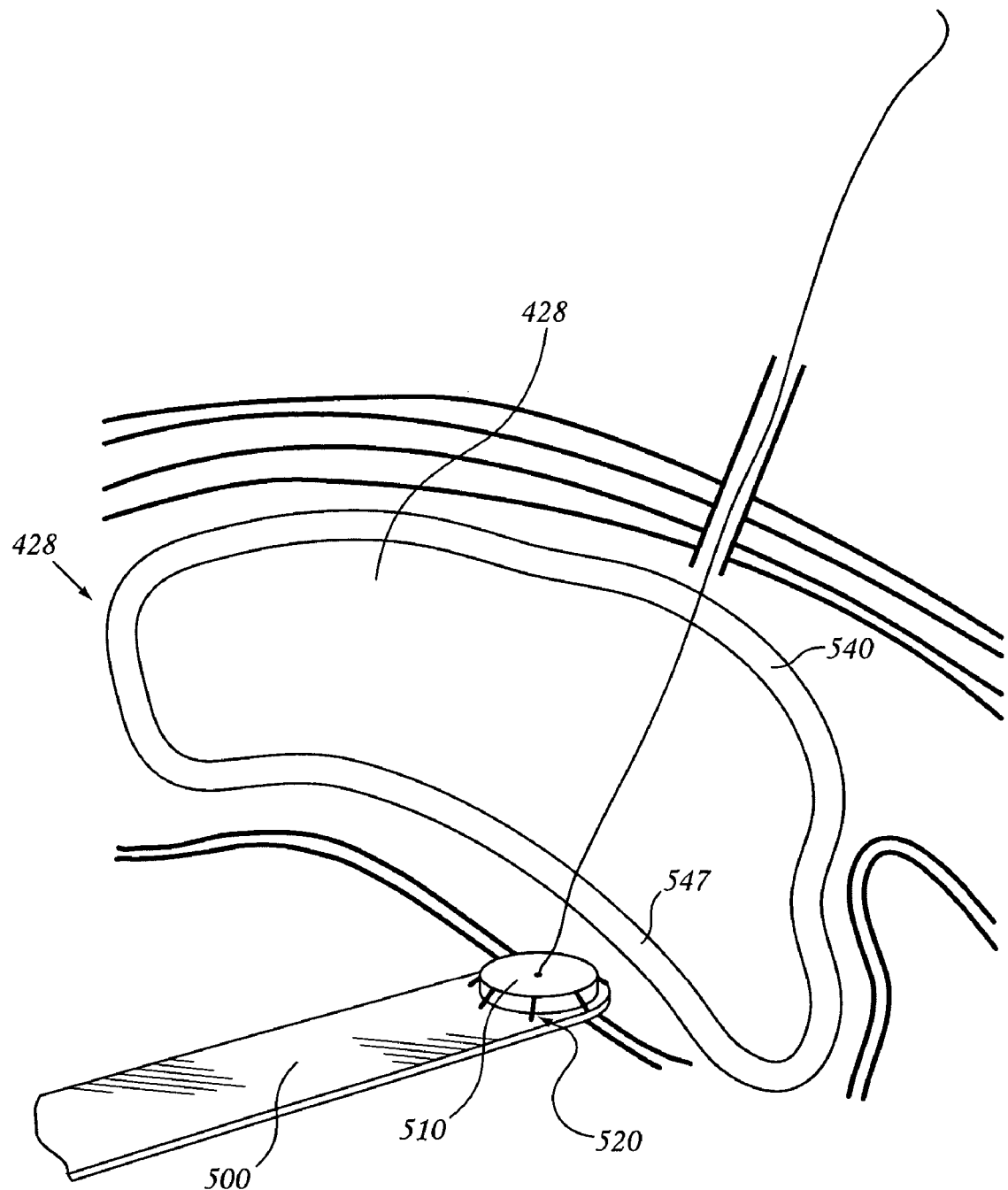
Figure 13A:
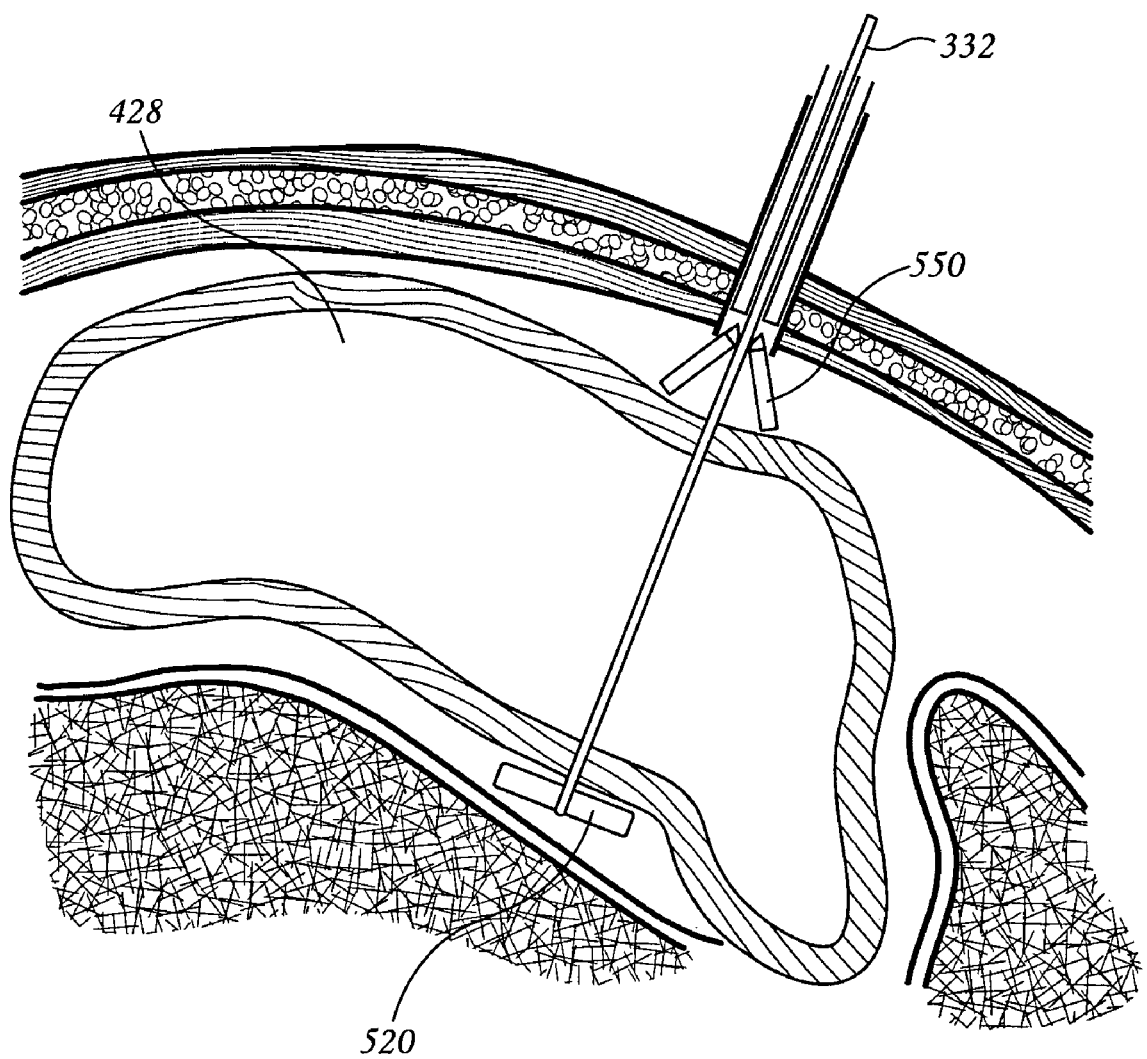
FIGS. 13a-b illustrate another step in the laparoscopic procedure in which the anterior anchor is urged toward the posterior anchor over a connector.
Figure 13B:
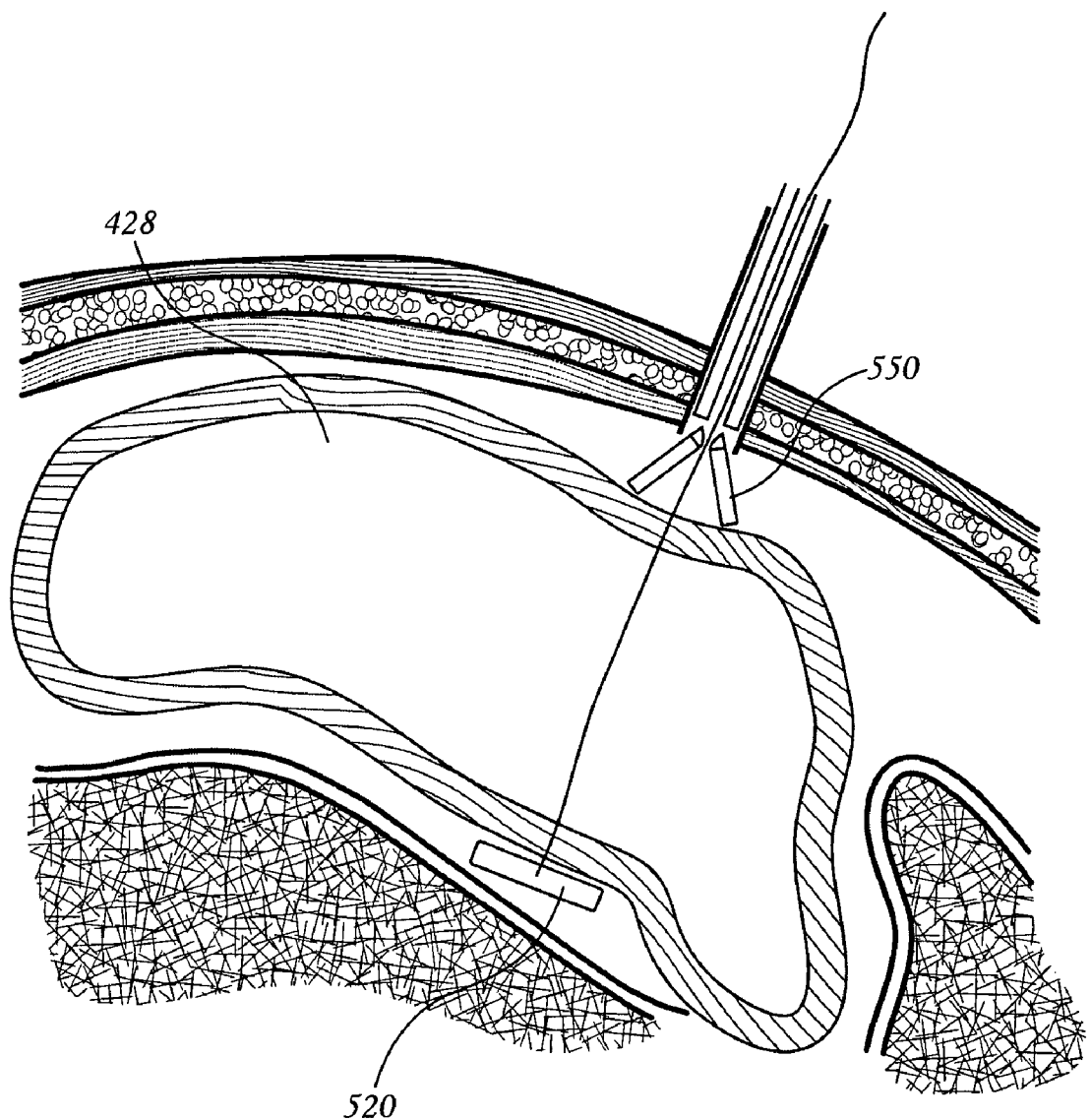

FIGS. 12a-c depicts some of the steps in one embodiment of a "laparoscopic procedure"; a laparoscopic instrument 500 is provided which has a reversibly attached anchor 510. Grips 520 reversibly grip anchor 510. Any of a variety of gripping mechanisms can be employed to retain the anchor 510 on laparoscopic tool 500. Connector 332 is substantially similar to any of the connectors described above except that in this embodiment, the posterior anchor 510 is not attached to connector 332 when it is inserted through the anterior abdominal wall. The surgeon places laparoscopic tool 500 behind the stomach 428 of the patient and connector 332 is advanced through the lumen of laparoscopic port 545 formed in patient's skin 535 and anterior abdominal wall 530. Connector 332 is then further advanced through first and second walls 540 and 547 of stomach 428. In FIG. 12B, a suture 333 is an inner component of the connector 332 for the transgastric device; an outer portion of connector 332 is removable over the suture after the suture 333 is attached to the posterior anchor 510; connector 332 is then removed from the patient (FIG. 12C).

In some embodiments, a suture is provided on the posterior anchor 510 (not shown) prior to insertion of the connector 332; connector 332 is adapted to pull the suture through the stomach and thence through the abdominal wall after being inserted through the anterior and posterior wall of the stomach. This results in a configuration similar to FIG. 12C. Subsequent attachment of the anterior fastener/s and subsequent urging step where the anterior and posterior walls are brought together is similar as outlined above.

When the connector 332 reaches the posterior anchor 510, gripping elements 520 are released by the surgeon through a mechanism which is integrated into the laparoscopic tool 500. Connector 332 is fixed to posterior anchor 510 through a locking mechanism. Mechanisms of locking connector 332 to posterior anchor 510 are well-known to those skilled in the art of mechanical fixturing. Some or all of the fixturing mechanisms may reside on the connector or on the anchor. In another embodiment, the gripping force of the grippers 520 can be overcome by force applied by the surgeon on connector 332. Reversible locking means other than mechanical means also exist and include magnetic, electromagnetic, and adhesive means.

Figure 14A:
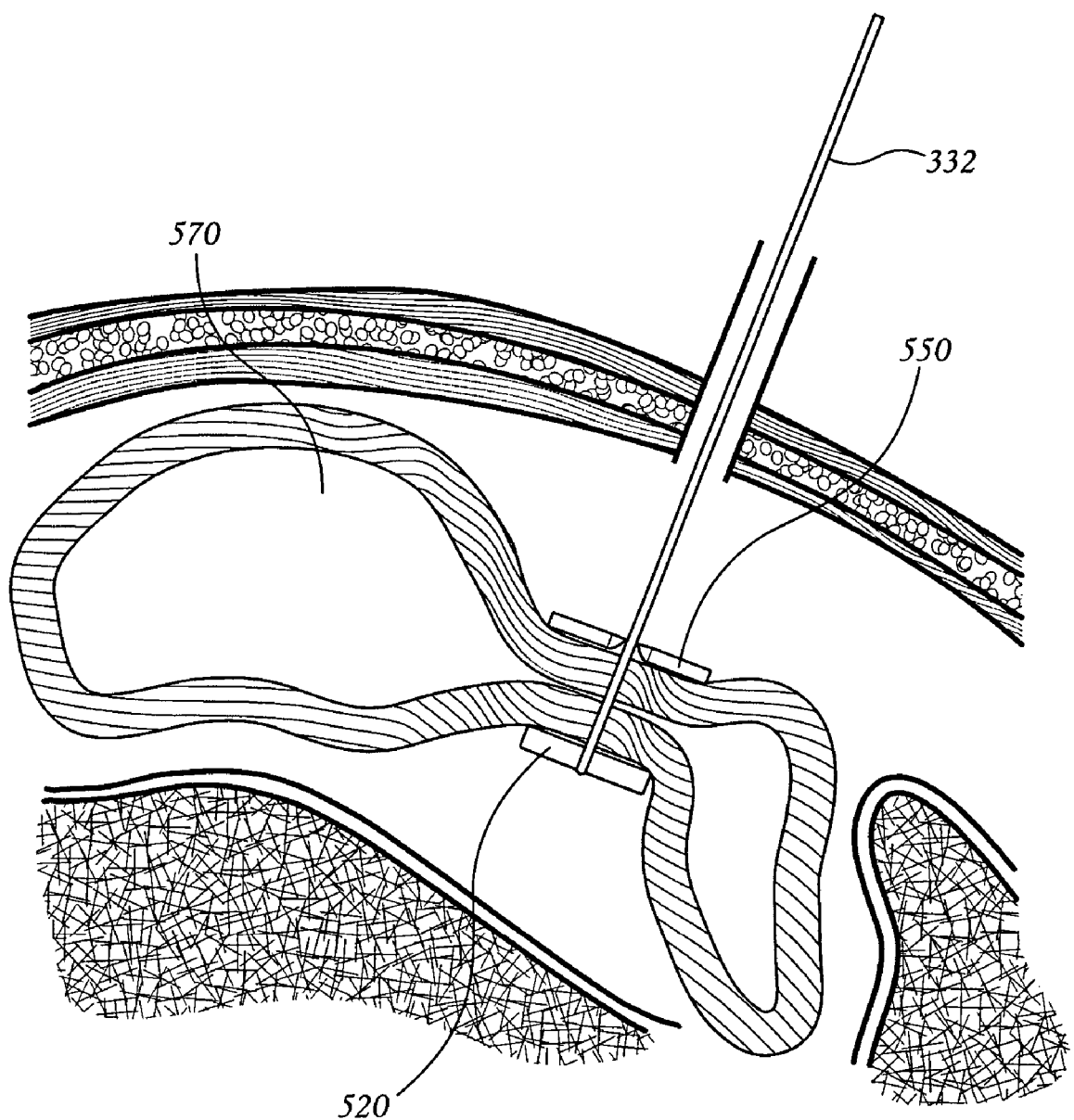
FIGS. 14a-c illustrate another step in the laparoscopic procedure in which the anterior and posterior walls of the stomach are urged together and the connector and the transgastric suture are cut flush with the anterior anchor.
Figure 14B:
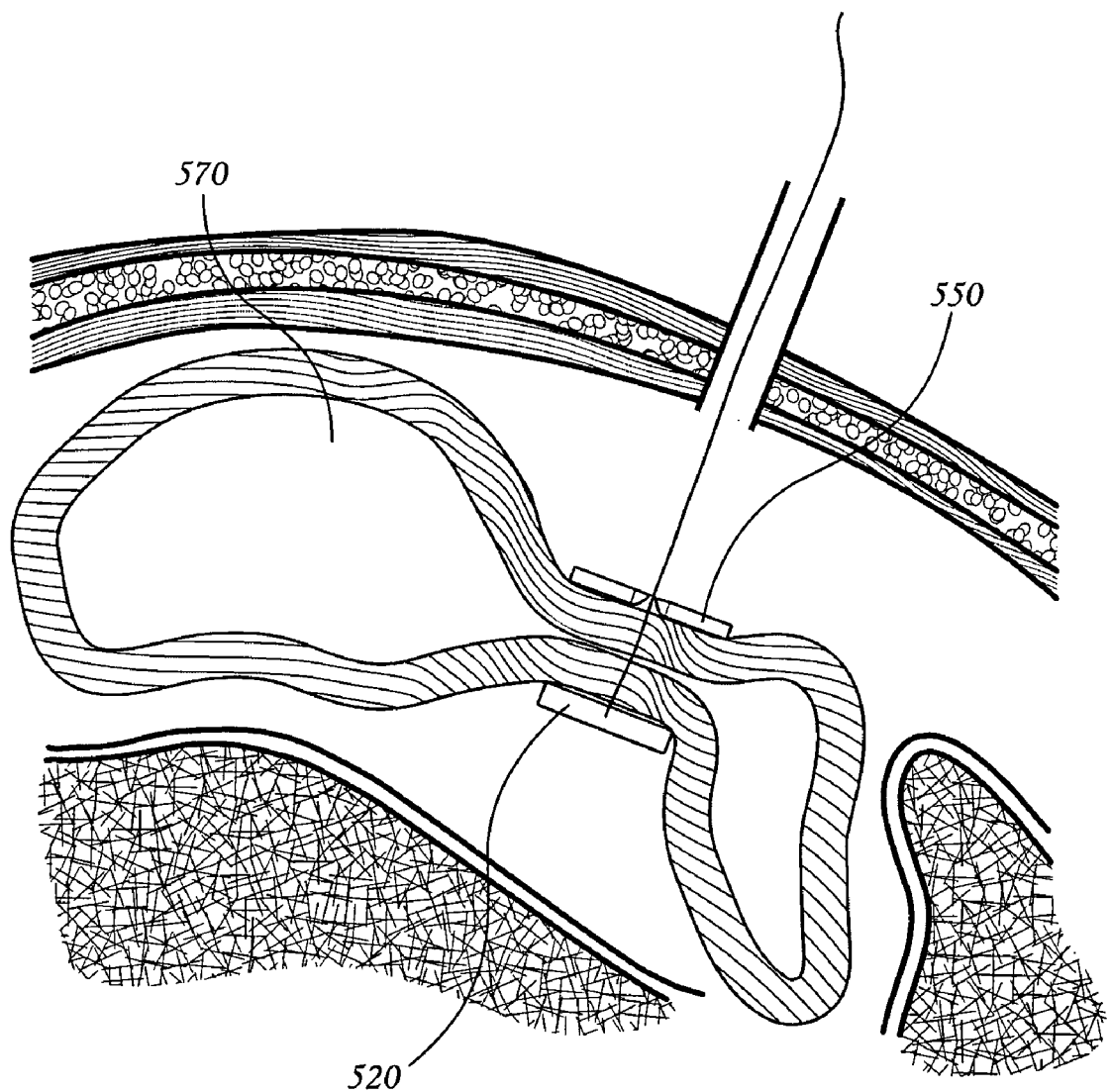
Figure 14C:
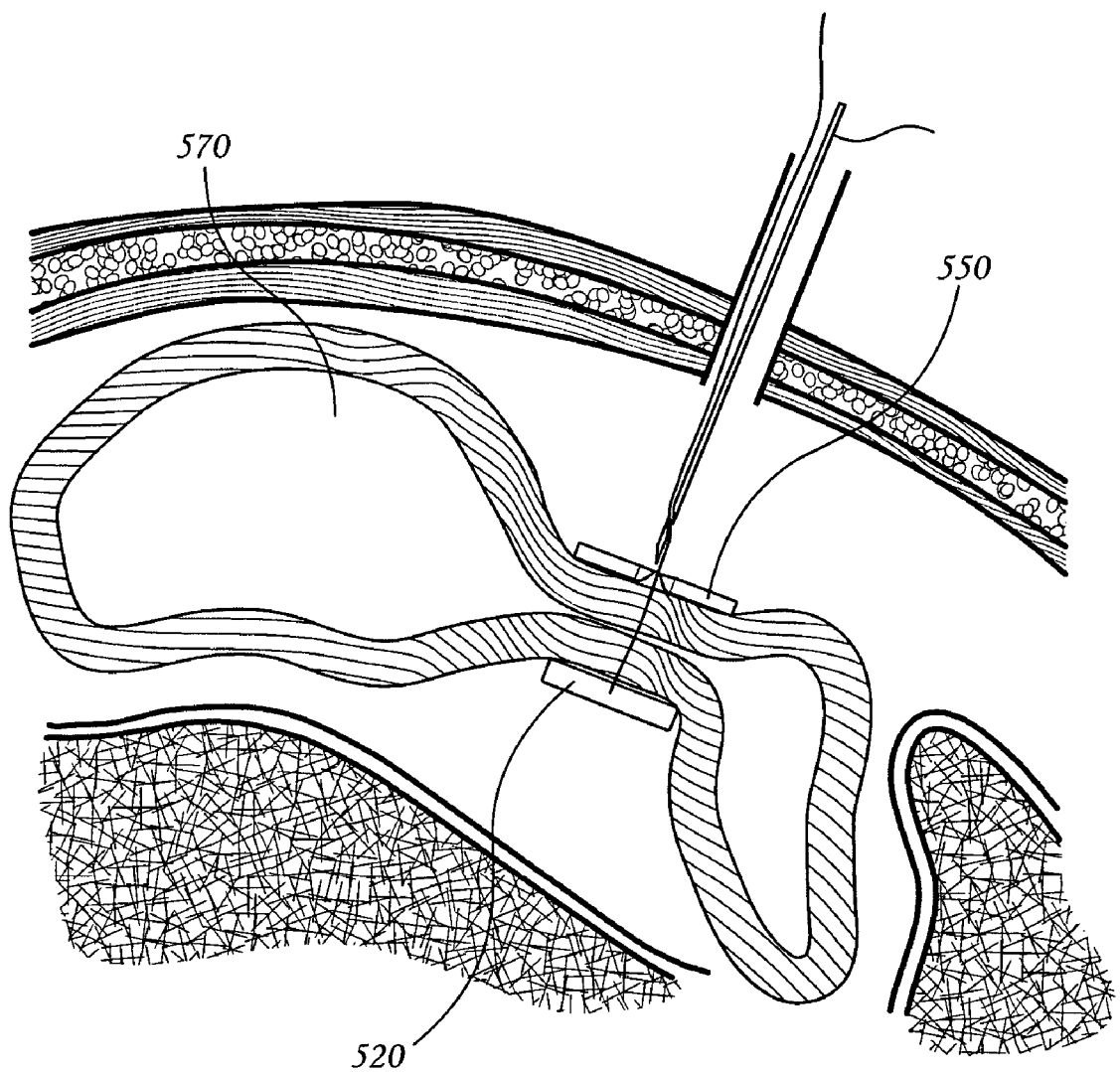

An anterior anchor 550 (FIG. 13a) is then placed over the connector 332 by the methodology and devices described in the next paragraph; the mechanism of deploying the anterior anchor is the same in both the "laparoscopic" and "percutaneous" procedures. The walls of the stomach are urged together (FIG. 14a) to create a resistance to the flow of food within the stomach or to reduce the volume of the stomach. 570 depicts one side of the stomach after the walls of the stomach are urged together. 570 is the side of the stomach where the food enters. Its (the stomach) volume and capacity are now reduced as compared to its original volume and capacity. Although not shown, connector 332 is subsequently truncated at the level of the anterior anchor 550 after the anterior anchor is deployed by any of the mechanisms described and depicted above.

Figure 7A:
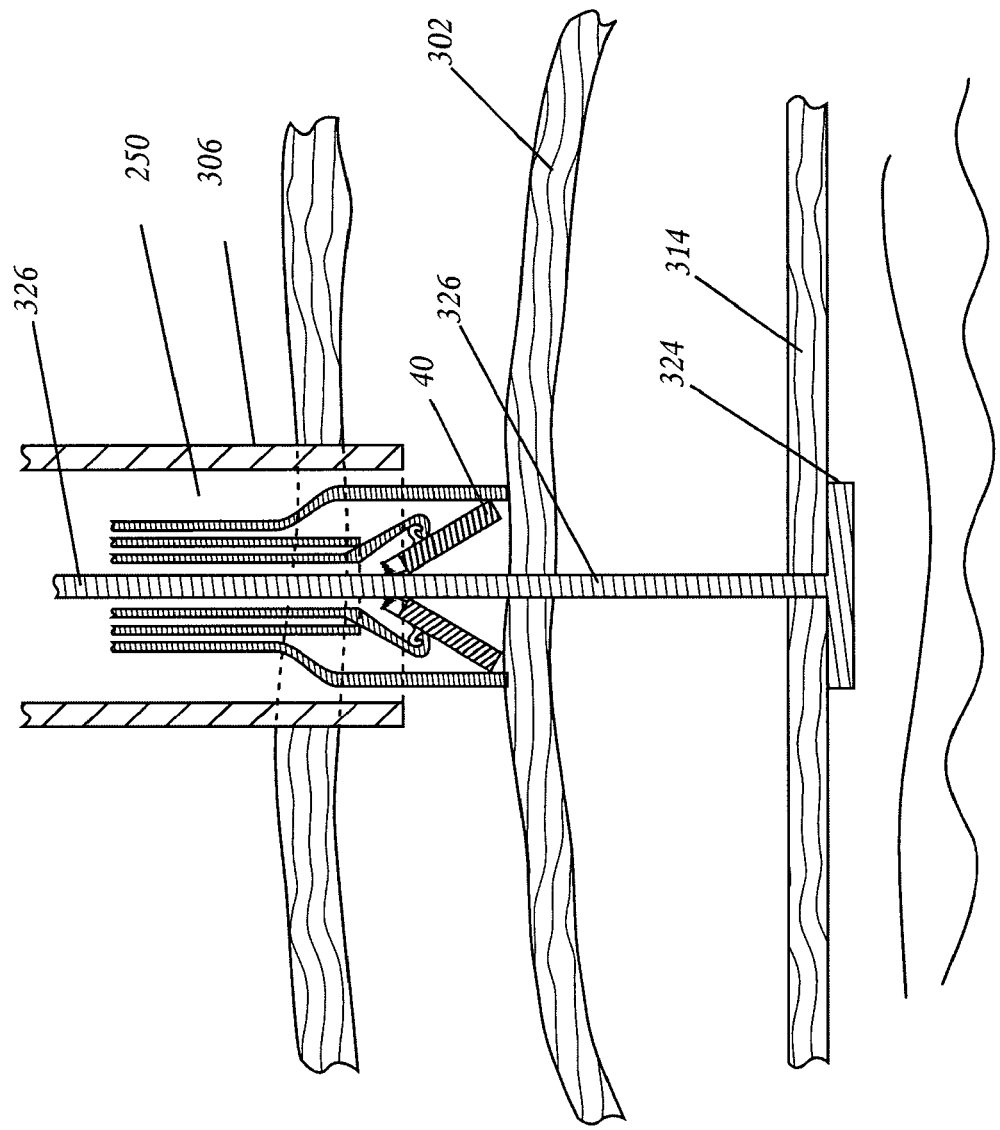
FIG. 7A illustrates the next step in one embodiment of a method of reducing the volume of the stomach. Shown is a side sectional view of a patient's abdomen with the instrument of FIG. 5C placing an anterior anchor in the patient's abdomen adjacent to the anterior wall of the stomach.

FIG. 7A illustrates the step of implanting the anterior anchor in one embodiment. The connector 326 is inserted through the hole or other passageway of an anterior anchor 40 of FIG. 5C, and the anchor implantation instrument 250 of FIGS. 5A, 5B and 5C is used to slide the anchor 40 through the laparoscopic port 306 into the abdomen of the patient. The anterior 302 and posterior 314 walls of the stomach are urged together, either by using the anchor implantation instrument 250 to urge the anterior wall 302 toward the posterior wall 314, or by pulling on the connector 326 and posterior anchor 324 to urge the posterior wall 302 of the stomach toward the anterior wall 314, or by a combination of the two methods. Once the anterior anchor 40 is in the desired position, the anterior anchor 40 is placed in its deployed configuration by manipulating the anchor implantation instrument 250 as described above.

In a preferred embodiment, the inflatable anterior anchor of FIGS. 2G-2I is used, and the use of the implantation instrument of FIG. 5A is optional. After the anterior anchor is in the desired position, the anterior anchor is inflated with a filling substance through the inflation tube until it is in its deployed configuration. The gripping elements 67 and teeth 68 are thus engaged against the connector 326, (12 in FIG. 2I). The anchor implantation device 250 (FIG. 5A) can then be withdrawn from the patient's abdomen.

Figure 15E:
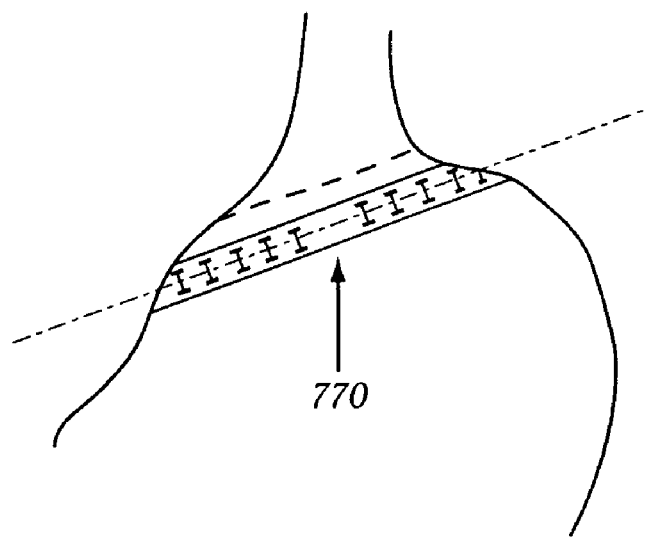
FIG. 15e-g depicts a configuration where both the anterior and posteriof fasteners are connected by a continuous mesh implant.
Figure 15F:
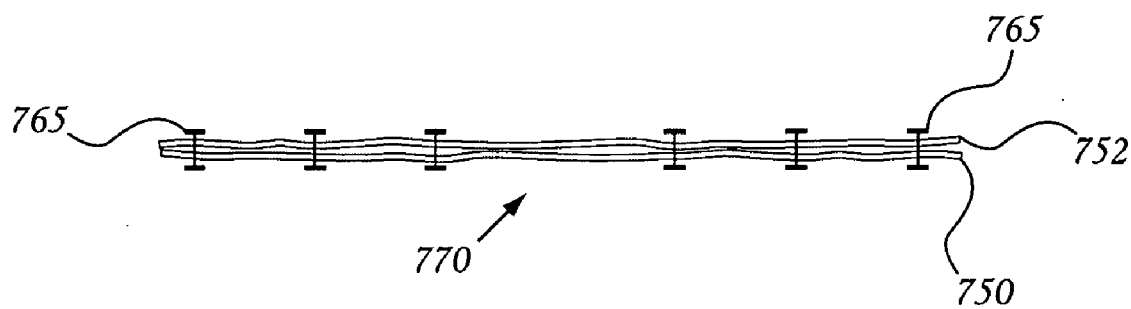
Figure 15G:
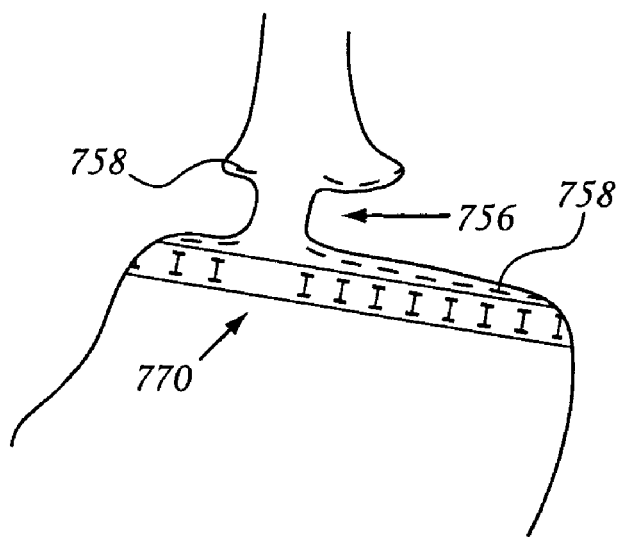

In another embodiment (FIG. 15e-g), both the posterior anchor 750 and the anterior anchor 752 are continuous along both the anterior and posterior portions of the stomach. In this embodiment, connectors 765 are suture like or are more rigid as described above. Strain gauges may be incorporated into any or all of the connectors 765. Region 770 is the where food flows through the restriction system. In some embodiments, it is desirable to transect 758 a part of the stomach with staplers well known in the surgical arts creating a region 756 between the staple lines.

With the transgastric fastening assembly complete, the surgeon can examine the resulting configuration of the stomach using an endoscope. If one or more anterior anchors is/are not in the desired location, its placement along the connector can be adjusted as described above. Alternatively, in another embodiment, the anterior anchor can be urged closer to the posterior anchor simply by pushing it along the connector without using the implantation device to capture the anchor and deform it into its reduced profile configuration.

In another embodiment, the anterior anchor can be deflated, allowing the anterior anchor to be repositioned (the anterior anchor is reversibly fixed to the connector), and then reinflated to engage the connector. FIG. 7B illustrates the transgastric fastening assembly with the anterior anchor 40 in its deployed configuration on the connector 326 and the anchor implantation instrument removed from the patient's abdomen. The anterior 302 and posterior walls 314 of the stomach have been urged closer together by the transgastric fastening assembly. Whether the walls of the stomach are urged into contact or not is determined by the surgeon. Contact between the mucosal surfaces can be loose such that food can go through yet a significant resistance to food is provided; alternatively, mucosal surfaces are urged together and touch; however, food cannot pass through the apposed surfaces.

Figure 7C:
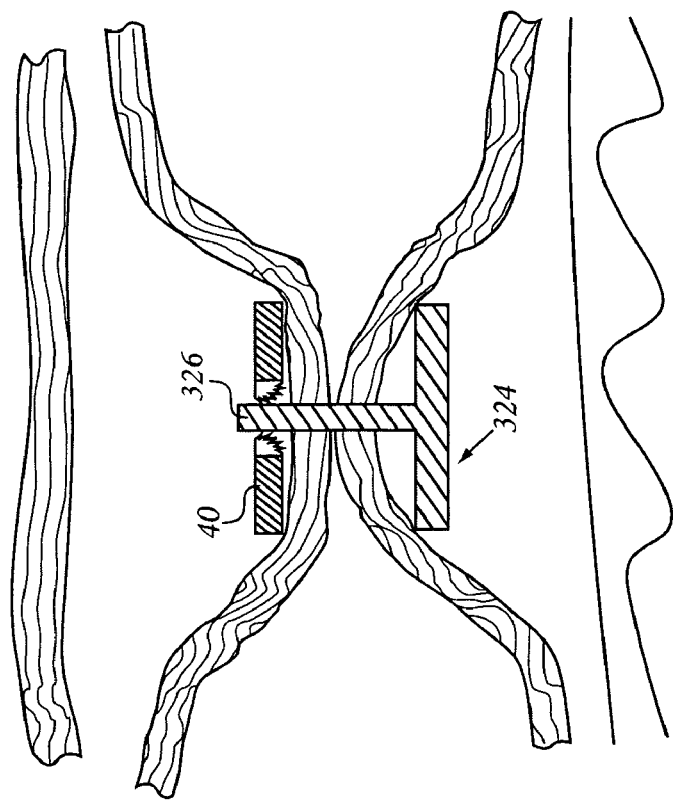
FIG. 7C illustrates the next step in one embodiment of a method of reducing the volume of the stomach. Shown is a side sectional view of a patient's abdomen after the connector has been cut flush with the anterior anchor.
Figure 7B:
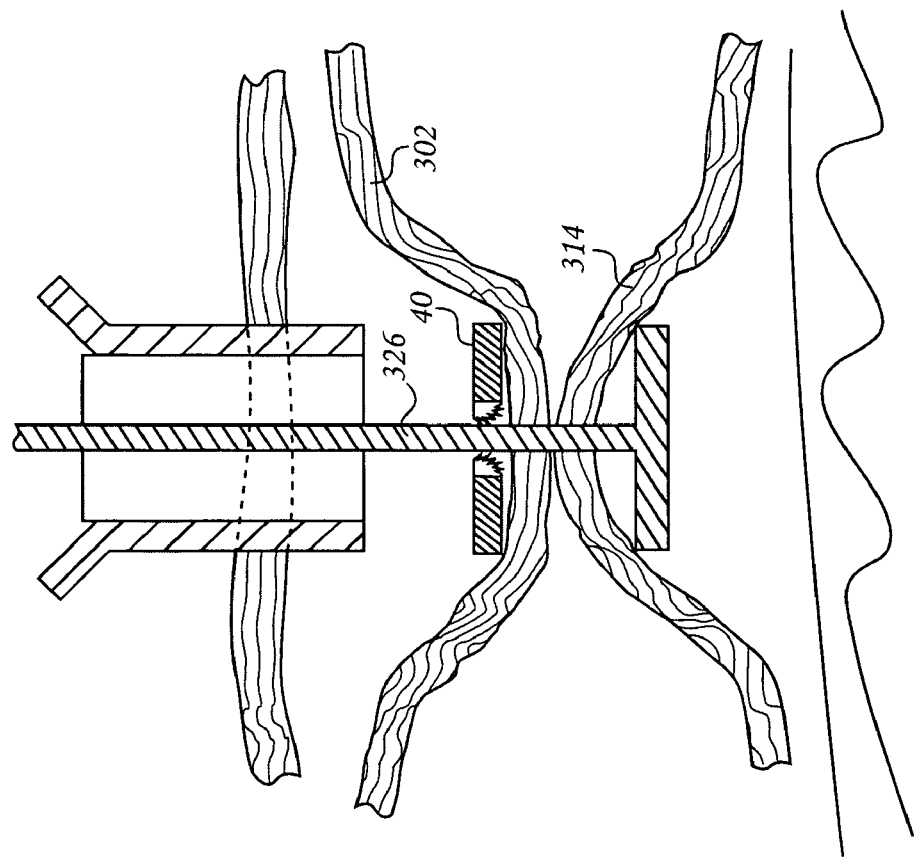
FIG. 7B illustrates the next step in one embodiment of a method of reducing the volume of the stomach. Shown is a side sectional view of a patient's abdomen with an anterior anchor in its deployed configuration on the connector, with the anterior and posterior walls of the stomach urged together.

FIG. 7C depicts a transgastric fastening assembly in its final configuration after deployment. Once the surgeon is satisfied that the transgastric fastening assembly is properly placed, a cutting implement, well-known to those of skill in the art, is inserted through the laparoscopic port and the connector 326 is cut, preferably flush to the anterior anchor 40. In some embodiments, the cutting instrument is placed over the connector with the connector as a guide. In an embodiment, where inflatable anchors are used, the hollow connector and inflation tube are sealed prior to, or as a result of, cutting, preventing anchor deflation. Alternatively, if a filling substance which hardens with time is used, it may not be necessary to seal the connector or inflation tube prior to cutting if the filling substance is sufficiently hard or viscous such that it will not leak from the connector or inflation tube.

When more than one transgastric fastening assembly is to be implanted, it is sometimes preferred to insert all of the posterior anchors and connectors before attaching any or all anterior anchors. For example, in FIG. 8A, posterior anchors 330 are show in a position posterior to the stomach with connectors 332 outside the abdomen. Anterior anchors can now be placed over the connectors 332 and the tension independently adjusted under endoscopic visualization. In some embodiments, an instrument to measure and quantify tension is used to measure the compression of the stomach mucosa prior to the operation. In some embodiments (FIG. 8B), test blocks 336 are placed on the laparoscopic ports 334. The tension on connectors 332 can now be tested without placing an anterior fastener on the connector. This type of parallel fastener placement and quantification allows the operator to control the tension of each individual fastener across a row of fasteners. Test blocks 336 are adapted to engage connectors 332 and the optimal tension on the connectors 332 can be quantified using a standard tensiometer attached to connectors 332. The degree of volume reduction can also be tested with this setup and by visualization with endoscope 344. Once the optimal tension has been determined, the anterior fastener is placed over the connector at the pre-determined tension. Tensioning of individual fasteners is in contrast to attempting place transgastric fastening assemblies in series. While possible to individually place transgastric assemblies in series, if one were to do so, each successive assembly would be more difficult to place because the volume of the stomach would be progressively reduced, resulting in more difficult visualization each time.

Figure 8A:
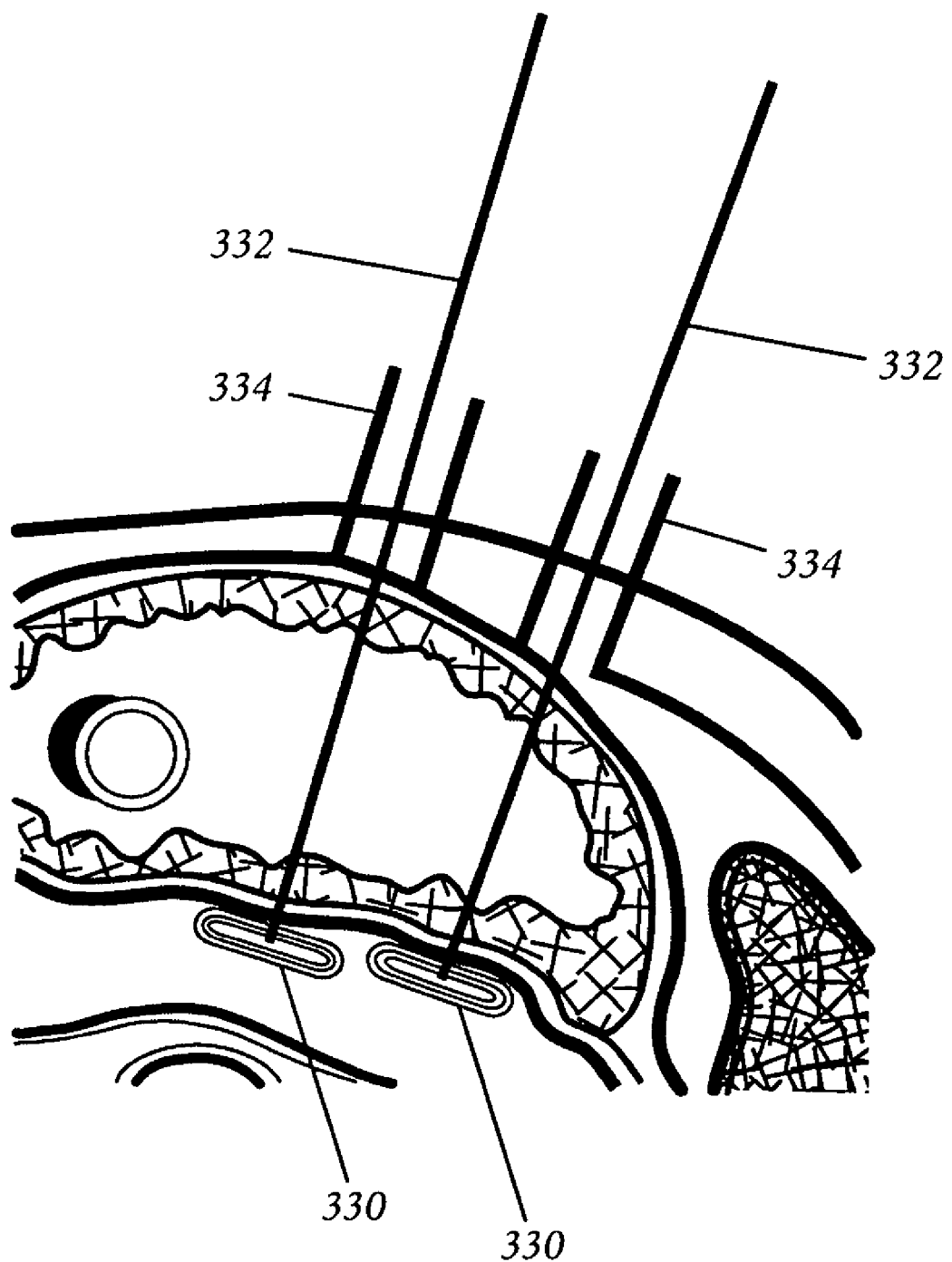
FIG. 8A illustrates an embodiment of a method of reducing the volume of the stomach. Shown is a side sectional view of a patient's abdomen after two posterior anchors and connectors have been deployed adjacent to the posterior wall of the stomach, with the connectors passing out of the patient's abdomen through laparoscopic ports.

FIG. 8A depicts an embodiment in which two posterior anchors 330 and connectors 332 are deployed in the expanded lesser peritoneal sac. In this embodiment, there is one laparoscopic port 334 for each connector 332. In an alternative embodiment, there may be more anchors placed than incisions and laparoscopic ports. Depending on how far apart the anchors are placed, a given laparoscopic port can be used to implant a plurality of transgastric implants. This can be accomplished because there is significant mobility of the stomach and/or abdominal wall which allows for different points along the anterior wall of the stomach to be accessed without having to create another hole through the abdominal wall.

Figure 8B:
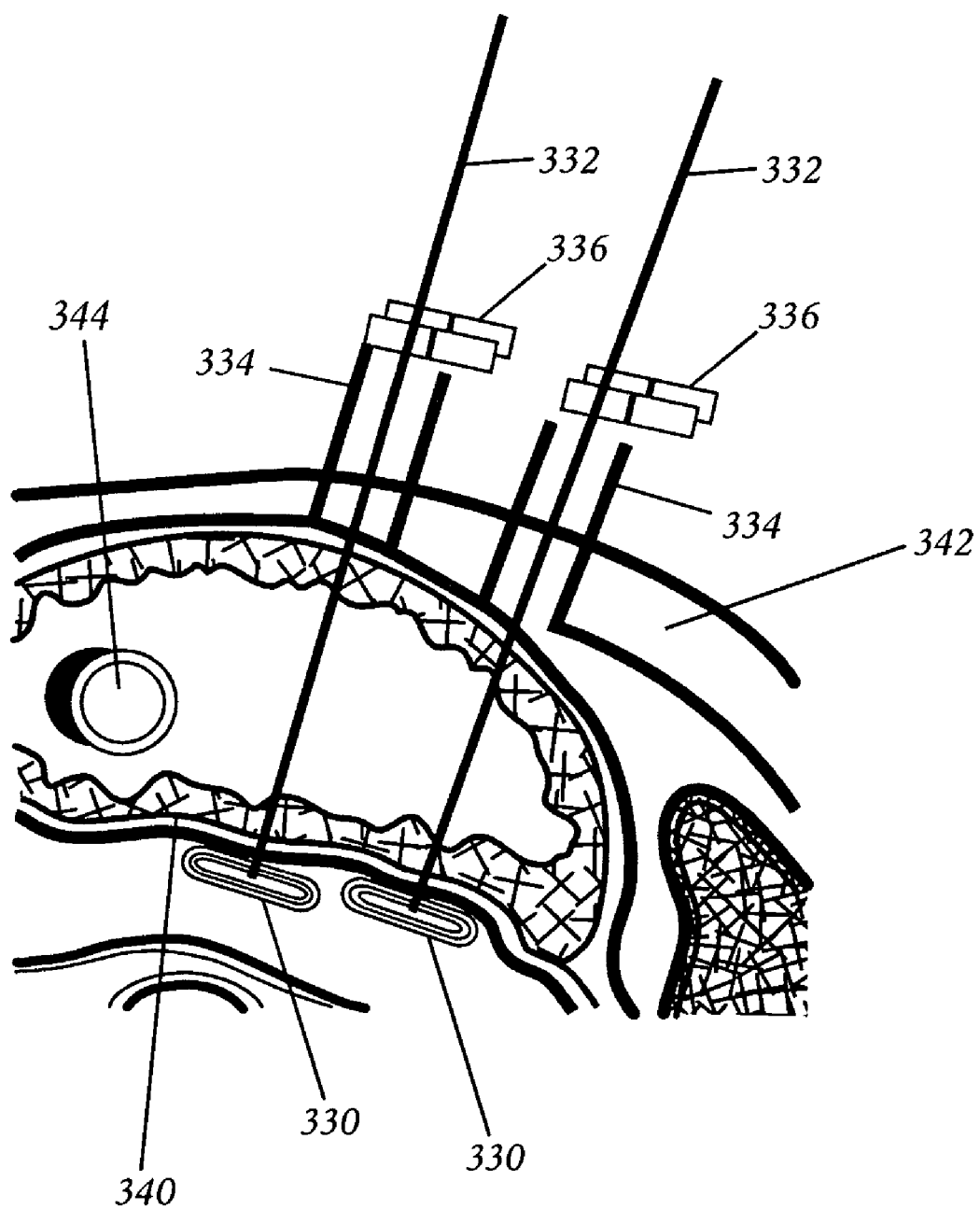
FIG. 8B shows the connectors of FIG. 8A with clamps placed on the connectors outside the patient's body to temporarily hold the connectors in a test position.

In an alternative embodiment, the stomach is fastened to the abdominal wall rather than there being a free space between the anterior gastric wall and the peritoneum of the abdominal wall (not shown). The initial steps are as discussed above. After the posterior anchors are placed, their position can be tested as depicted in FIG. 8B to simulate the configuration after the anterior anchor is placed. Next, the outer laparoscopic port is pulled back so that the anchor deploying instrument directly contacts and sits within the tissues of the muscular abdominal wall. Once the outer laparoscopic port is pulled back, the anterior anchor can be deployed within the abdominal wall musculature and the connector can be cut flush with the anterior anchor. In an embodiment where the inflatable anterior anchor is used, after the anterior anchor is deployed within the abdominal wall musculature, the inflation tube is cut, preferably flush with the anterior anchor.

Method of Reversal

The connector 326 (e.g. a suture) of a preferred embodiment of the deployed transgastric fastening assembly, as illustrated in FIG. 7C, can be cut at a point between the anterior and posterior anchors, which results in reversal of the gastric volume reduction. The connector is preferably made to resist corrosion from stomach acid, but is able to be cut by a cutting implement advanced through an endoscope into the stomach. In the Smith paper (Smith, L. et. al. Results and Complications of Gastric Partitioning. The American Journal of Surgery. Vol. 146; December 1983), a nylon suture was used to traverse the stomach in the anterior-posterior direction and attach the pledgets to the walls of the stomach. The nylon material was suitable for use for over 3 years without any indication of corrosion. Other materials suitable to prevent corrosion and yet allow cutting include plastics such as polyurethane, silicone elastomer, polypropylene, PTFE, PVDF, or polyester, metals and metal alloys such as stainless steel, nickel-titanium, titanium, cobalt-chromium, etc. Once the connector is cut, the walls of the stomach are free to move away from one another, thereby reversing the procedure. Reversal of the procedure can occur at any time (days to years) after the procedure. In a preferred embodiment, the anchors remain in the gastric wall permanently even after the connector is cut or otherwise divided; the anchors are made from a material which facilitates permanent integration into the gastric wall (or other intestinal wall); suitable materials include polypropylene, Alloderm™, Surgisis™, and polyesters. Alternatively in other embodiments, the anchors can, in part or in whole, be manufactured from a bioabsorbable material such that the anchors will eventually be absorbed by the body. In the case of bioabsorbable anchors, it is preferable to have a connector which is at least in part bioabsorbable. In another embodiment, substantially all of the elements of the transgastric fastening assembly are made of bioabsorbable materials, with the intent that over the desired period of time, the entire assembly will be absorbed by the body, reversing the procedure without any additional actions required by a doctor. In another embodiment, the anchors are made of a non-reactive material such as silicone. In this embodiment, reversal of the procedure requires a "laparoscopic procedure;" that is, pneumoperitoneum so that the connectors can be cut and the fasteners removed. The connector is cut with the endoscope and then the anchors are removed with standard laparoscopic instrumentation; being composed of silicone, the anchors in this case will be easily removed.

Even if there is some degree of fusion between the mucosa around the connector at the region of the assembly, once the connector is cut or absorbed, the walls will tend to move apart over time. Alternatively, a balloon or other dissection device is introduced through an endoscope and used to urge apart the walls of the stomach at the point of fusion.

Additional Embodiments of the Disclosed Devices, Instruments, and Methods

The devices, methods and instruments disclosed above and below can be used to treat other diseases, such as gastroesophageal reflux disease (GERD). In this embodiment, a transgastric fastening assembly is placed in the cardia region. Such a configuration would maintain the position of the GE junction in the abdomen and potentially create a barrier to reflux contents. Similar to the devices above, feedback systems can be instituted so that the reflux prevention is initiated as a response to a stimulus such as pH or peristalsis rather than applying continuous pressure to the tissue even when reflux is not present. Furthermore, GERD devices can be equipped with patient controlled features such that when the patient feels symptoms, the antireflux features are activated. Reflux disease can also be treated with sutures or plications placed with a percutaneous procedure and in the region of the GE junction. Placement of the sutures (with or without pledgets) with a percutaneous procedure would not require general anesthesia and would be advantageous in many patients.

Figure 9:
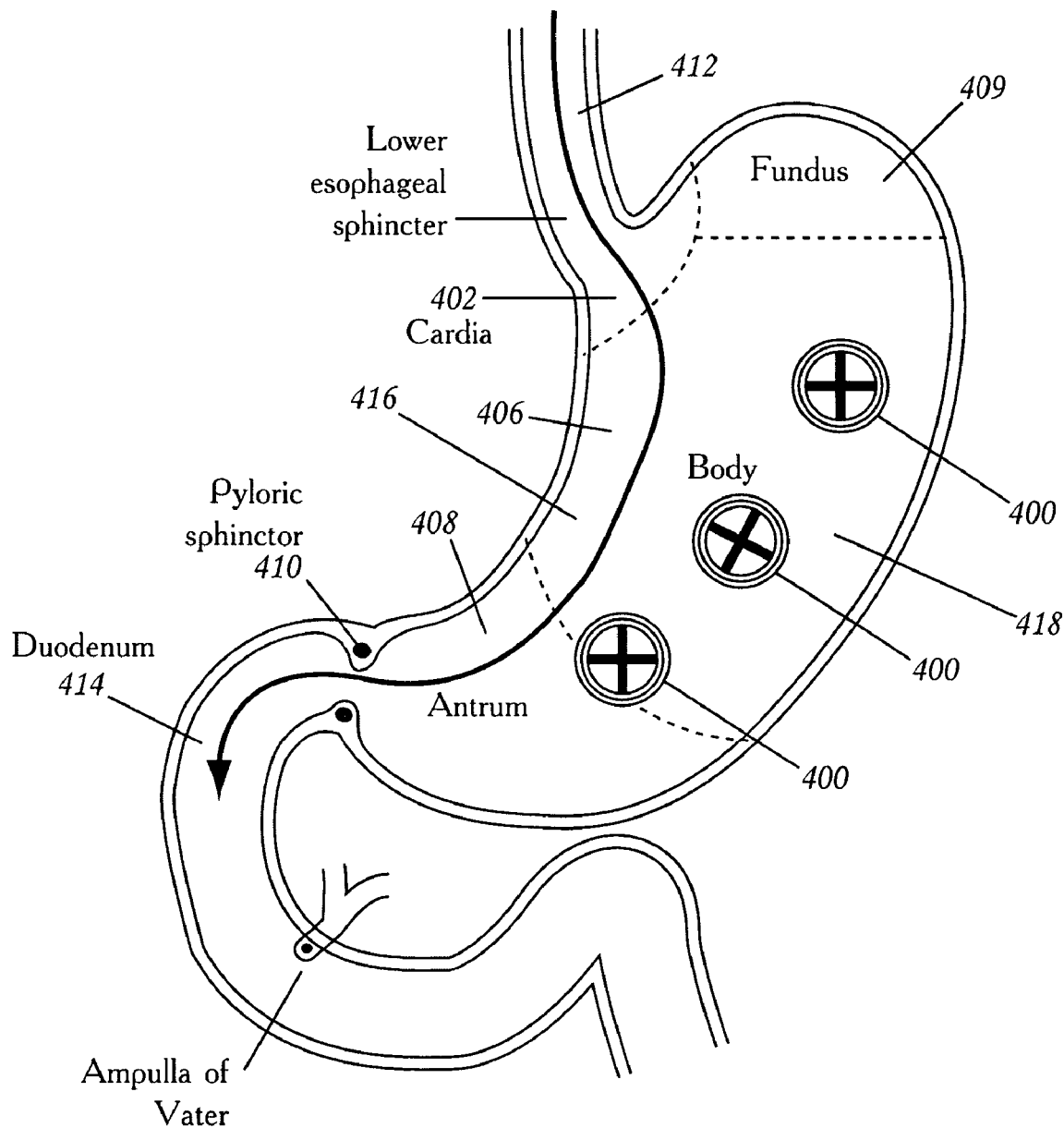
FIG. 9 is a perspective view showing three transgastric fastening assemblies deployed longitudinally in a patient's stomach.

In many of the embodiments discussed above, a transverse row of fasteners is depicted which is one method of creating volume reduction or flow restriction. FIG. 9 depicts and alternative embodiment in which three transgastric fastening assemblies 400 are deployed longitudinally in the stomach; such a configuration of anchors results in a tubular configuration of the remaining portion of the stomach. The dashed lines represent boundaries of the divisions of the stomach: the cardia of the stomach 402, the fundus of the stomach 409, the body of the stomach 406, the antrum of the stomach 408, and the pyloric sphincter 410. In one embodiment, the fastening assemblies are not implanted in the antrum 408 (but are implanted longitudinally in the stomach as shown in FIG. 9) in order to maintain the normal digestion process of the stomach. Normal digestion therefore occurs in the antrum which precedes passage of food into the duodenum. In stopping short of the antrum 408, the implants replicate the degree of volume reduction of the Magenstrasse and Mill (M&M) procedure (discussed above in the background).

Food ingested by the patient follows a physiologic pathway for digestion depicted by the arrow in FIG. 9. It travels through the esophagus 412 and enters the cardia of the stomach 402. The food is digested in the stomach and pushed toward the duodenum 414 as chyme for further digestion. The preserved antrum 408 allows for relatively physiologic digestion and emptying into the duodenum 414 akin to the M&M procedure. With transgastric fastening assemblies 400 in place, food which leaves the esophagus 412 and enters the stomach, results in increased wall tension on the lesser curvature of the stomach 416 as the greater curvature of the stomach 418 will be restricted from the food pathway. The path of least resistance will be the path toward the pylorus 410 and duodenum 414. The increased wall tension of the stomach will result in a feeling of satiety by the patient, leading to decreased food intake and weight loss. As discussed further above, any of the transgastric assemblies in this embodiment can have feedback systems which communicate with patient end-effector, patient afferent pathways, device efferent, and/or device afferent pathways. Although three assemblies are shown in FIG. 9, there may be as few as one or as many as ten or more depending on the degree of volume reduction desired. Such flexibility in number of devices as well as the ability of the surgeon to tune the tension between the anterior and posterior anchors is advantageous. Such flexibility may enable, for example, reversal of a few anchors rather than all the anchors, such that the volume reduction procedure is partially reversed. As described above, any or all of the anchors, or parts of the anchors, can be biodegradable and therefore, the gastric reduction procedure would be reversible by virtue of the implanted biodegradable anchors. Furthermore, in some embodiments where there are multiple transgastric connectors which are produced from an electrically active material, different ones of the multiple connectors can be adjusted. In some embodiments, an electrical current is applied to the structures in order to reverse the procedure. For example, some metals and polymers will dissolve (corrode) in response to current.

In another embodiment, a transgastric fastening assembly is placed in the antrum 408 or the region just proximal to the pyloric sphincter 410 if deemed necessary by the gastroenterologist and/or surgeon. Such a configuration would not reduce the volume of the stomach but would cause a feeling of fullness similar to a gastric outlet obstruction, leading to decreased food intake and weight loss. The anchors in this region can also conduct a current to electrically stimulate the pyloric region to simulate satiety.

In another embodiment, a transgastric fastening assembly may be required at the region of the cardia 402 to treat morbid obesity in a similar manner to that utilized with the LAP-BAND™ (Inamed Corp., Santa Barbara, Calif.). In this embodiment, the transgastric fastening assembly is not utilized to reduce the volume of the stomach, but to create a restriction to the inflow of food. In this embodiment, the fastening system can traverse the cardia but does not necessarily completely oppose the mucosal surfaces of the anterior and posterior walls of the stomach. In some embodiments, the transgastric assemblies do in fact completely appose the walls of the stomach together but allow food to pass through by not completely traversing the cardia, leaving a space for flow of food stuffs. The assembly can further be configured to provide electrical signals to the anterior and/or posterior portions of the stomach in this region. The active region of this embodiment can be quite large, in some cases ranging up to 10-15 cm, large enough to traverse almost the entire width of the cardia.

In another embodiment, the disclosed methods in combination with the transgastric fastening assemblies can be adapted to attach a gastrointestinal organ to the abdominal wall which, in addition to reducing volume, can also create a kink in the organ (e.g. the stomach). The kink may cause a resistance barrier (in addition to volume reduction) to gastrointestinal contents and can be useful to treat reflux disease or morbid obesity. Such a kink would also fix the gastrointestinal region to the abdominal wall as well as maintain the reduction of a hiatal hernia in the abdominal compartment (e.g. in reflux disease). A major component of reflux disease is a hiatal hernia in which the gastroesophageal junction freely slides from the abdomen to the mediastinum. A percutaneously placed suture or anchor in the region of the gastric cardia and/or fundus can tether the junction to the abdominal wall and confine the junction to the abdomen.

In other embodiments, the devices and methods of this invention can assist in the implantation of devices such as stents, meshes, stitches, or tubes in the gastrointestinal tract. A major technical difficulty encountered in placing stents, tubes, balloons, stimulators, and meshes inside the lumen of the gastrointestinal tract is that they tend to migrate because the walls of such devices do not adhere to slippery mucosa. A transgastric or transintestinal anchor, implanted with the current instrumentation, could solve this problem. Such a method would be particularly useful in the attachment of the stent part of the stent-sleeve system outlined in patent application US20050075622A1, or the mesh of patent application US20040172141A1. In another example, devices such as those disclosed in U.S. Pat. No. 6,773,441 attempt to place an endoscopic stitch to tether the cardia of the stomach to the fundus to treat reflux disease. Such stitches are tenuous in the long term because they do not necessarily penetrate the serosa. Even if the stitches penetrate the serosa, they tend to erode through the wall with time because of their thin profile and an inability of the endoscopic operator to control tension on the suture when it is placed. With the methods and devices of this invention, such an endoscopic suture can be buttressed with a percutaneously placed anchor.

Although the described methods are focused on the implantation of transgastric fastening assemblies to reduce the volume of the stomach or to increase the resistance to the flow of food in the stomach, the methods and devices can easily be expanded to the implantation of other types of devices such as neurostimulators, gastric muscle stimulators, gastric balloons, and bulking devices inside the wall of a gastrointestinal organ using the percutaneous procedures and devices described herein.

The methods disclosed herein (e.g. the percutaneous procedure) can further be used to apply an energy source to an internal organ without having to give general anesthesia or pneumoperitoneum. For example, the methods and devices of the current invention can be used to apply radiofrequency probes, microwave probes, ultrasound probes, and radioactive probes (to the serosa) in similar ways as disclosed in U.S. Pat. No. 6,872,206. The energy sources can be temporary or permanent and can be activated remotely through the abdominal wall in the case where they are implantable. The methods can further be used for diagnostic purposes prior to performing a surgical therapy. In one example, the methods and devices are used to identify specific nerves or nerve plexuses prior to delivering a specific therapy. In another example, specific hormone producing regions, such as ghrelin, are identified prior to delivering a specific therapy. Following the methods and devices outlined both above and below, instruments can be placed in the abdominal cavity under percutaneous guidance. Any of the layers of the stomach can be accessed and stimulation, ablation, or diagnostic devices can subsequently be placed without anesthesia and without pneumoperitoneum. For example, a stimulation device can be placed in any layer of the stomach wall such as the serosa or muscular layers for example.

Similarly, the anchor assemblies and anchors are applied to solid organs such as the spleen, kidney, liver, and pancreas to urge the edges of a defect together to promote healing; in other embodiments, the anchor assemblies are applied to the blood vessels such as arteries or veins; for example, the aorta or vena cava.

Figure 7E:
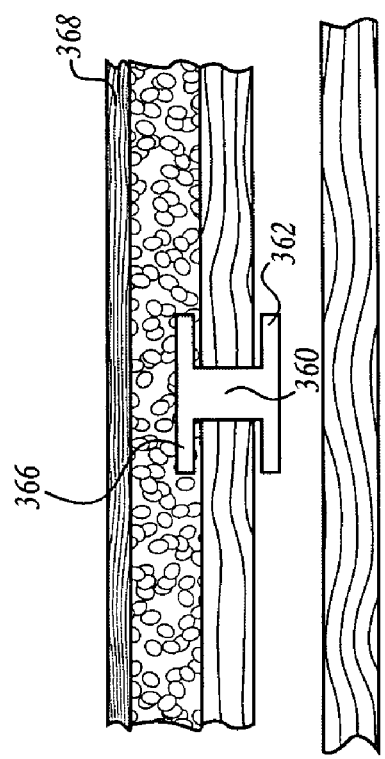
FIGS. 7D-E illustrates a transgastric fastening assembly placed in a position to close a fascial defect from a laparoscopic port.
Figure 7D:
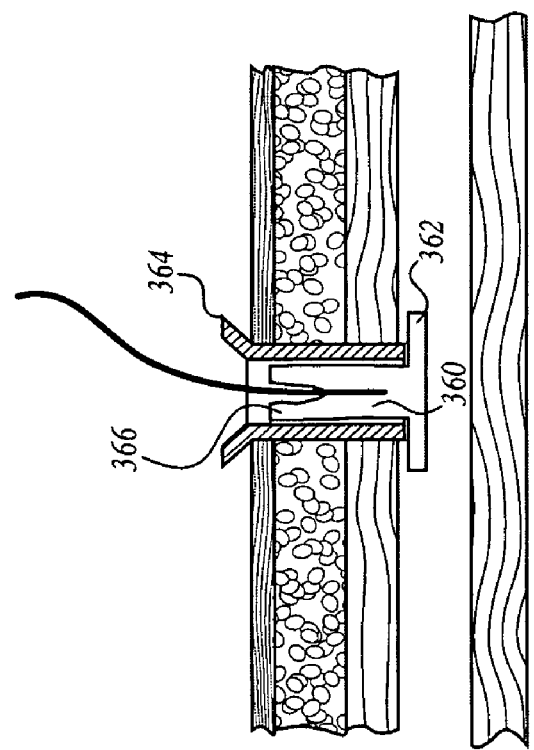

In still further embodiments, fascial defects can be closed with the anchoring assembly described above. FIG. 7*d*-7*e* for example shows an anchor being delivered into a fascial defect caused by a laparoscopic port. Using similar methodology as above except applied to a fascial defect, a posterior anchor 362, a connector 360 and an anterior anchor 366 are shown in FIG. 7D. A laparoscopic port 364 is shown as well. After anterior anchor 366 is threaded over connector 360, the connector is 360 is trimmed as described above (shown in FIG. 7E). When the anchoring assembly is in place as shown in FIG. 7E, the defect created by port 364 is effectively closed and the connector stabilized in the anterior abdominal wall. Typically, laparoscopic fascial defects are closed with sutures which can be very difficult in an obese patient. The anchor-connector-anchor assembly shown in FIGS. 7D-E is a possible solution to having to close fascial defects with sutures in obese patients.

In some embodiments, the methods and devices described herein are used to place devices inside or outside the stomach; inside or outside the lesser sac of the peritoneum; inside or beside a structure within the retroperitoneum; inside, beside, or outside the duodenum, pylorus, or gastroesophageal junction. Implanted devices include but are not limited to the anchor devices and transgastric fastening assemblies described above; stents, meshes, stent-grafts, stitches, stimulators, and bulk forming agents can be implanted individually, in combination, and as a component of the same device.

In some embodiments, a transgastric method of placing such stimulators is described which in some embodiments enable placement of stimulators in the lesser peritoneal space where they can stimulate the sympathetic system or directly stimulate structures in the lesser peritoneal sac (such as the pancreas). In these and other embodiments, the transgastric access method to the lesser peritoneal sac is used to place stimulators and stimulate and/or inhibit pain fibers in and around the celiac ganglion. This type of procedure is used to treat patients with severe pain from a tumor or from pancreatitis.

Devices that circumscribe the gastroesophageal junction are well-known in the art (see for example, U.S. Pat. No. 6,464,697); the surgical constricting balloons can be retrofitted with sensors in order to create device afferent pathways which detect overeating and simulate (via device efferent pathways) patient afferent pathways such as the vagus nerve or the visceral nervous system.

The methods and devices of this invention can also be used to place sutures in the stomach or pylorus to treat reflux disease or obesity. Such suturing would be facilitated by the placement of multiple ports through the walls of the stomach. Any of these methods and devices could be used in combination with or in place of the transgastric fastening assemblies to induce weight loss in a patient.

Figure 10B:
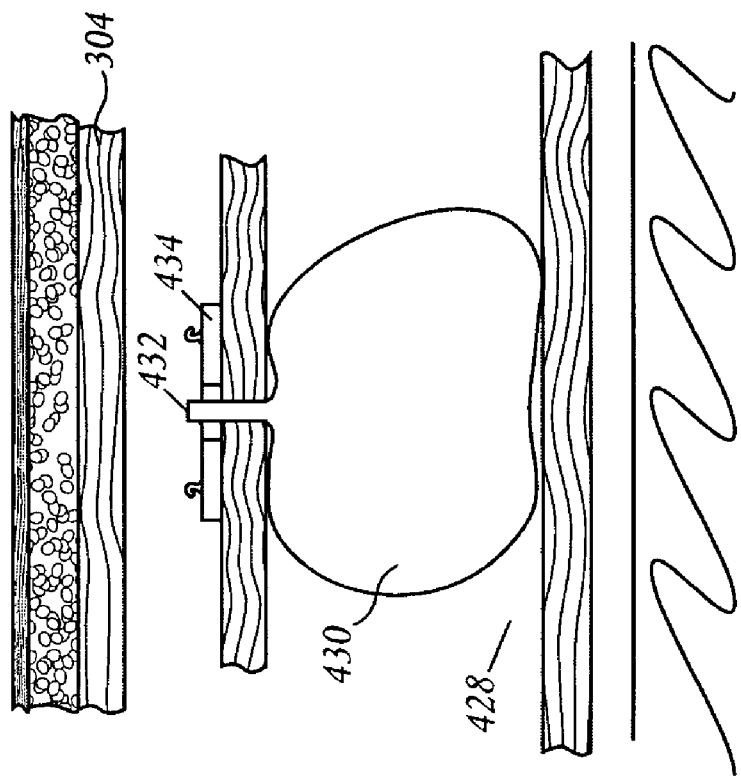
FIG. 10B illustrates one embodiment of a method for deploying a volume displacing device in the stomach. Shown is a side sectional view of a patient's abdomen with the balloon anchor in its deployed position, held in place by an anterior anchor and connector.
Figure 10A:
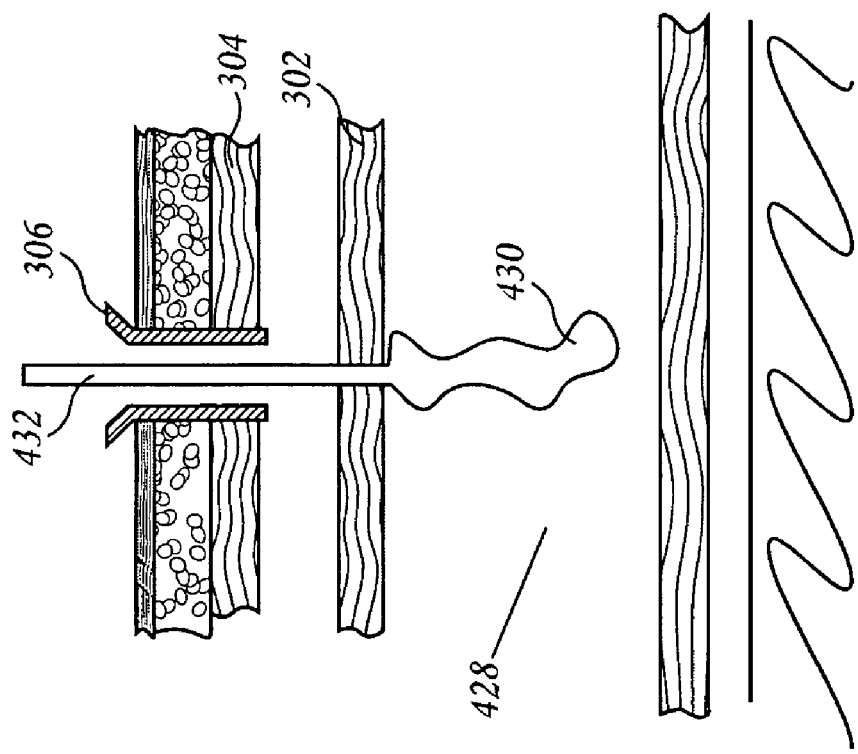
FIG. 10A illustrates one embodiment of a method for deploying a volume displacing device in the stomach. Shown is a side sectional view of a patient's abdomen after an uninflated balloon anchor has been inserted inside the patient's stomach with a connector passing out of the stomach, through the anterior stomach wall, and through a laparoscopic port.

In another embodiment, the novel methods, implantation devices, and anchors of this invention are used to implant devices in one wall of a gastrointestinal organ without volume reduction. One example of such an embodiment is illustrated in FIGS. 10A and 10B in which a balloon-like device is deployed in the stomach to displace volume rather than to reduce volume from the outside. The internal balloon 430 is similar to the posterior anchors in some of the embodiments described above. In one embodiment, after initial insufflation of the stomach and placement of a laparoscopic port 306 percutaneously and without pneumoperitoneum (as described above) between the abdominal wall 304 and the anterior wall of the stomach 302, an instrument is used to penetrate only the anterior wall of the stomach 302 and place an inflatable intragastric balloon 430. Inflation is achieved through the connector lumen 432 and the balloon is placed within the interior of the stomach 428, as illustrated in FIG. 10A. When inflated, the balloon 430 is preferably spherical in shape such that it occupies a substantial portion of the stomach volume when inflated. In the embodiment shown, the connector also acts as the inflation tube for inflating the intragastric balloon. In another embodiment, in addition to the connector, there is a separate inflation tube similar to embodiments presented above. As discussed above, a valve can be located between the anchor and the connector, or alternatively outside the patient. Preferably after the intragastric balloon is inflated and an anterior anchor 434 is deployed on the connector 432, as described previously. The connector 432 is also cut, preferably flush with the anterior anchor, and the laparoscopic port is removed, as shown in FIG. 10B. The anchor portion of the intragastric balloon 434 is then fixed in the wall of the stomach. In the preferred embodiment where an inflatable anterior anchor 434 is used, the inflation tube is also cut, preferably flush with the anterior anchor. Other devices which may only be implanted in one gastric wall with similar methods and with similar anchoring devices include neurostimulators, muscular stimulators, sensors, and pharmaceutical delivery devices.

Figure 16:
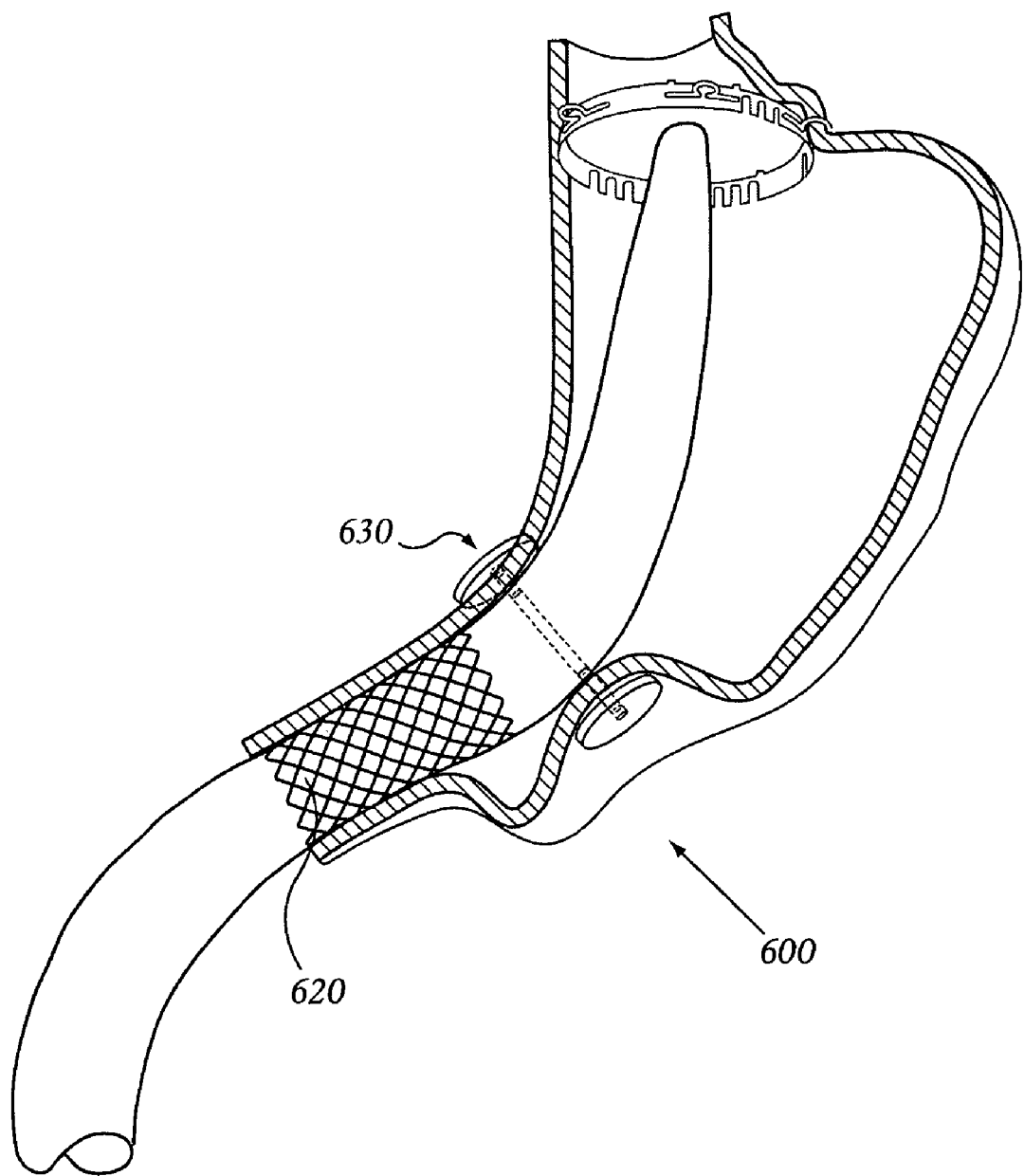
FIG. 16 depicts anchors of the present invention being used to secure an endoscopically placed gastric implant.

FIG. 16 embodies another use for the current invention. The sleeve device 620 is disclosed in US patent application publication US2004/02206882. A major difficulty with this sleeve device is that it is not easily fixtured for stability inside the stomach. Fastening system 610 is used to assist in fixation of the device 620 to the stomach wall; fastening system 610 is any of the devices discussed above and is implanted by any of the methods discussed above.

In another embodiment, a surgical anastomosis is surrounded with the organ spanning anchors and anchor assemblies of the current invention. In this embodiment, the anchors can buttress the anastomosis to protect the integrity of the anastomosis. The buttresses can support both hand-sewn and stapler anastomotic techniques. To prevent or the anchors are placed around or through the anastomosis. In a similar embodiment, a transgastric anchor system (or constricting band) can be used at a gastrojejunostomy in a Roux-n-Y bypass procedure. Both the transgastric anchor system and constricting band can further have associated electrically activateable elements through which flow through the anastomosis can be controlled.

The anchors (and bands), as described above, can also be used to control the flow of material through an anastomosis. Flow control is attainable when an anchoring assembly is applied across an anastomosis and are linked by means of a connector through the anastomosis. The distance between the anchors determines the amount of flow through the anastomosis and therefore, the flow rate can be adjusted quite readily with the device of the current invention. The flow rate is adjustable at anytime during or after the operation. Luminal devices to control the flow rate through an anastomosis can be found in US patent application number 20050022827. The devices of the current invention can be used to accomplish the goal of controlling flow through an anastomosis by placing anchors on either side of the anastomosis with a connector that traverses the anastomosis. Furthermore, the anastomotic flow control device can further have automated control using the materials, methods, and control systems described above in order to automatically adjust flow control or tension on the anastomosis.

In another embodiment, the anchor assemblies are applied to the lung to treat chronic obstructive pulmonary disease (COPD) via functional lung reduction. Rather than removing a portion of the lung (the surgical procedure), the anchors of the current invention are placed through the diseased portion of the lung to close off or at least create a large resistance in one portion of the lung and broncheoalveolar tree so that inspired air does not reach a malfunctioning portion of the lung.

In other embodiments of the current invention, the fastening systems and tools to implant the fastening systems are used to secure closure or repair of blood vessels. The blood vessels can be named vessels such as the aorta, vena cava, pulmonary veins, pulmonary arteries, renal vein, renal artery, inferior mesenteric vein and/or artery, splenic vein and/or artery, portal vein and/or hepatic artery, or the saphenous and/or deep veins. Alternatively, the vessels are unnamed such as in the case of the mesentery of the colon or small bowel. Vessel closure with the current system is possibly more efficient than current laparoscopic means of vessel closure which involve staple or clip occlusion of the vessels; staples and clips do not penetrate the vessel and therefore are often inadequate, or at least do not replicate what a surgeon would do in an open procedure which is place a suture through the vessel to "suture ligate" it as is well-known in the art.

It is also possible that a part of, or any or all of the devices and methods described above are performed with an alternative imaging means; for example, fluoroscope, MRI, ultrasound, and CAT scan.

Although the present invention has been described in the context of certain preferred or illustrative embodiments, it should be understood that the scope of the exclusive right granted by this patent is not limited to those embodiments, but instead is the full lawful scope of the appended claims.

Furthermore, any of the devices, methods, surgical instruments, and features can be used singly or together in order to treat any of the disorders or diseases mentioned above.

What is claimed is:

1. A method of quantifying the effectiveness of a gastric restriction in a patient undergoing treatment for obesity comprising:
    Sensing a parameter associated with the stress on a gastric restriction with an implantable parameter sensing device wherein the gastric restriction is created through a surgical bypass procedure.
2. The method of claim 1 further comprising;
    Interpreting the parameter in relation to the patient's treatment plan.
3. The method of claim 1 further comprising:
    Changing the treatment plan of the patient based on the parameter to improve upon weight loss for the patient.
4. The method of claim 1 wherein the gastric restriction further comprises an adjustable restriction device.
5. The method of claim 4 wherein the adjustable restriction device is a band which encircles the fundus of the stomach.
6. The method of claim 1 wherein the gastric restriction further comprises a transgastric anchoring assembly.
7. The method of claim 1 further comprising: generating an output signal.
8. The method of claim 7 further comprising: storing the output signal.

9. The method of claim 7 wherein the output signal is a wireless signal.

10. The method of claim 1 further comprising an electrical stimulator, coupled to the parameter to modulate the treat of obesity.

11. A method of quantifying the effectiveness of a stomach restriction device in a patient undergoing treatment for obesity comprising:
Sensing a parameter associated with the stress on the stomach restriction device;
Sensing a signal generated by a body structure in relation to the parameter wherein the structure generating the signal is an enteric nervous structure or a visceral nervous structure.

12. The method of claim 11 further comprising: delivering the signal related to the parameter to a communicator.

13. The method of claim 11 wherein the parameter is sensed on a port in fluid communication with the gastric restriction device.

14. The method of claim 13 wherein the parameter is pressure.

15. The method of claim 11 wherein the enteric nervous structure is in the wall of the stomach and wherein the method further comprises the step of delivering a physiologic electrical sensor to the wall of the stomach.

16. The method of claim 11 wherein the visceral nervous structure is a vagus nerve.

17. The method of claim 11 wherein the visceral nervous structure is a sympathetic nervous structure.

18. The method of claim 11 wherein the gastric restriction device is a circumferential band placed around the stomach.

19. The method of claim 11 wherein the gastric restriction device is an extragastric inflateable device which does not fully surround the stomach.

20. The method of claim 11 wherein the gastric restriction device is a transgastric anchor assembly.

* * * * *